US008541428B2

(12) United States Patent
Gavish et al.

(10) Patent No.: US 8,541,428 B2
(45) Date of Patent: Sep. 24, 2013

(54) HETEROCYCLIC DERIVATIVES, PHARMACEUTICAL COMPOSITIONS AND METHODS OF USE THEREOF

(75) Inventors: Moshe Gavish, Tel Aviv (IL); Jehuda Arieh Veenman, Nahariya (IL); Alex Shterenberg, Petah Tikva (IL); Ilan Marek, Haifa (IL)

(73) Assignee: Technion Research and Development Foundation Ltd., Technion, Haifa (IL)

( * ) Notice: Subject to any disclaimer, the term of this patent is extended or adjusted under 35 U.S.C. 154(b) by 688 days.

(21) Appl. No.: 12/438,291

(22) PCT Filed: Aug. 22, 2006

(86) PCT No.: PCT/IL2006/000979
§ 371 (c)(1),
(2), (4) Date: Sep. 24, 2009

(87) PCT Pub. No.: WO2008/023357
PCT Pub. Date: Feb. 28, 2008

(65) Prior Publication Data
US 2010/0029658 A1    Feb. 4, 2010

(51) Int. Cl.
*A01N 43/54*    (2006.01)
*A61K 31/517*    (2006.01)
*C07D 239/72*    (2006.01)

(52) U.S. Cl.
USPC ..................................... 514/266.1; 544/283

(58) Field of Classification Search
USPC ..................................... 544/283; 514/266.1
See application file for complete search history.

(56) References Cited

U.S. PATENT DOCUMENTS

| | | | |
|---|---|---|---|
| 4,499,094 A | 2/1985 | Dubroeucq et al. | 514/301 |
| 6,765,006 B2 | 7/2004 | Upasani et al. | 514/232.8 |

FOREIGN PATENT DOCUMENTS

| | | |
|---|---|---|
| WO | WO 96/40646 | 12/1996 |
| WO | WO 97/40020 | 10/1997 |

OTHER PUBLICATIONS

Ammar et al., Synthesis and effect of gamma irradiation on some new 6,8-dichloro-4-(3H)-quinazolinones of biological interest. Current Science (1989), 58(22), 1231-4 CODEN: CUSCAM; ISSN: 0011-3891; English.*
Khalifa el al., Synthesis of some quinazolone derivatives with tuberculostatic activity. Zagazig Journal of Pharmaceutical Sciences (1995), 4(1-B), 287-93 CODEN: ZJPSEV; ISSN: 1110-5089; English.*
Van Muijlwijk et al Desai et al Vippagunta et al.*
Reddy et al., Synthesis and spectral studies of iron(III) and iron(II) complexes with 2,3-disubstituted quinazolin-4(3H)-ones. Indian Journal of Chemistry, Section A: Inorganic, Bio-inorganic, Physical, Theoretical & Analytical Chemistry (2000), 39A(11), 1202-1206 CODEN: ICACEC; ISSN: 0376-4710; English.*
Khalifa et al., Zagzig J'nal of Pharmaceutical Sciences.*
International Search Report PCT/IL2006/000979 Dated Dec. 5, 2007.
Benavides J. et al., (1983) J Neurochem 41(6):1744-1750.
Berge S. M. et al., (1977) "Pharmaceutical Salts" J. Pharm. Sci., 66:1-19.
Bourguignon Jean-Jacques—XP001248799 (1996) "Identical and non-identical twin drugs" practice and medicinal chemistry 261-293.
Buchwald H. et al., (1980) Surgery 88(4):507-516.
Campiani Giuseppe et al., (1996) J Med Chem 39(18):3435-3450.
Deniau Eric et al., (2003) A New Synthetic Route to Highly Enantioenriched 3-Substituted 2,3-Dihydro-1 H-isoindol-1-ones. Tetrahedron: Asym. 14:2253-2258.
Gaetz Michael (2004) The neurophysiology of brain injury. Clin Neurophysio1.115(1 ):4-18.
Gaitner Michal, M.Sc. thesis, 2004 (abstract).
Galiegue Sylvaine et al.—XP009027200, (2003) The peripheral benzodiazepine receptor: a promising therapeutic drug target Cur Med Chem 10(16):1563-1572.
Hanefeld Wolfgang et al., (1996) 3-(2,5-Dioxopyrrolidin-1-y1), 3-(2,6-dioxopiperidin-1-yl), and 3-(1,3-10 dioxoisoindolin-2-yl)rhodanines. A novel type of rhodanine derivatives J Heterocyclic Chem. 33:1443-1146.
Kassab E. A.—XP009086292, (2005) Synthesis and behaviour of 4-(4'-chloro-3'methylphenyl)-1 (2H)-phthalazinone towards certain electrophiles and nucleophiles Egyp J Chem 48(2): 183-199.
Kluger Yoram et al., (2004) J Am Coli Surg.199(6):875-879.
Kugler W. et al., Abstracts of the 14th Annual Meeting of the Israel Society for Neuroscience, and the Joint Germany-Israel Meeting, Eilat, Israel, 2005 16:S38.
Kuznetsov V. et al., Abstract Viewer/Itinerary Planner. Washington, DC: Society for Neuroscience, Online: 2005; Program No. 673.4.
Langer S. Z. and Arbilla S. (1988) Pharmacologicol Biochem Behav 29(4):763-766.
Levin Evgeny et al., (2005) Biochemistry 44(29):9924-9935.
Maaser K. et al., (2001) Br J Cancer 85(11):1771-1780.
Mammen Mathai et al., Angew. Chem., Int. Ed. 1998,37:2755.
Ryu Jae K. et al., (2005) Peripheral benzodiazepine receptor ligand PK11195 reduces microglial activation and neuronal death in quinolinic acid-injected rat striatum. Neurobiol Dis 20(2):550-561.
Saito Yuko et al., (2001) Synthesis 2:221.
Saudek Christopher D. et al., (1989) N Engl J Med 321 (9):574-579.
Shternberg Alexander, M.Sc. thesis, 2006 (abstract).
Sullivan P. G. et al., (2005) J Neurosci Res. 79(1-2):231-239.
Veenman L. et al., (2002) J. Neurochem. 80(5):917-927.
Veenman L. and Gavish M. (2006) Pharmacol Ther. 110(3):503-524 (E published Dec. 2005).

(Continued)

*Primary Examiner* — Paul V. Ward
(74) *Attorney, Agent, or Firm* — Browdy and Neimark, PLLC.

(57) ABSTRACT

The present invention relates to novel quinoxaline, quinazoline and phthalazine derivatives as well as multimeric derivatives, methods for their preparation, pharmaceutical compositions including such compounds, and methods of using these compounds for the treatment and prevention of brain damage resulting from brain injury, especially secondary brain damage due to traumatic brain injury (TBI). The compounds of the invention are also useful in treating and preventing neurodegenerative diseases.

13 Claims, 26 Drawing Sheets

(56) References Cited

OTHER PUBLICATIONS

Veiga Sergio et al., (2005) J Neurosci Res. 80(1):129-137.
Weisinger Gary et al., (2004) Biochemistry 43(38):12315-12321.
Database registry [online] XP-002441443 Chemical abstracts service, Columbus, Ohio, US;2004, retrieved from STN Database accession No. 684234-45-5.
Database registry [online] XP-002441444 Chemical abstracts service, Columbus, Ohio, US; 2002, retrieved from STN Database accession No. 397300-59-3.
Database registry [online] XP-002441445 Chemical abstracts service, Columbus, Ohio, US; 2002, retrieved from STN Database accession No. 392734-64-4.
Database registry [online] XP-002441446 Chemical abstracts service, Columbus, Ohio, US; 2001, retrieved from STN Database accession No. 374908-45-9.
Database registry [online] XP-002441447 Chemical abstracts service, Columbus, Ohio, US; 2001, retrieved from STN Database accession No. 374772-28-8.
Database registry [online] XP-002441448 Chemical abstracts service, Columbus, Ohio, US; 2001, retrieved from STN Database accession No. 364615-21-4.
Database registry [online] XP-002441449 Chemical abstracts service, Columbus, Ohio, US;2001, retrieved from STN Database accession No. 364610-67-3.
Database registry [online] XP-002441450 Chemical abstracts service, Columbus, Ohio, US; 2001, retrieved from STN Database accession No. 333742-07-7.

* cited by examiner

Synthesis of Phthalazine derivatives.

9a: $R^1$ = $CH_3$  Yield: 60%

10a: $R^1$ = $CH_3$  Yield: 75%

10b: $R^1$ = $i$-Pr  Yield: 70%

I:
1) KH, DME
2)

II:
Pyridine, heat $R^1$ = $CH_3$, $i$-Pr results for 10⁻⁵ M ligand solution
in EtOH + Buffer phosphate (in comparison to PK11195)

HETEROCYCLIC DERIVATIVES, PHARMACEUTICAL COMPOSITIONS AND METHODS OF USE THEREOF

This application is a 371 filing of International Patent Application PCT/IL2006/000979 filed on Aug. 22, 2006.

FIELD OF THE INVENTION

The present invention relates to the field of quinazoline, phthalazine and quinoxaline derivatives, as well as multimeric compounds, methods for their preparation, pharmaceutical compositions including such compounds, and methods of using these compounds, especially for treating and preventing brain damage due to traumatic brain injury (TBI) and in treating and preventing neurodegenerative diseases.

BACKGROUND OF THE INVENTION

Traumatic brain injury (TBI) is characterized by sudden physical damage to the brain. It is caused by many factors including warfare, automobile accidents, sports injuries, violent crimes, household accidents, child abuse or by an object passing through the skull, for example gun shot wounds. The physical, behavioral, or mental changes that may result from TBI depend on the areas of the brain that are injured. Most injuries cause focal brain damage, damage confined to a small area of the brain. The focal damage is most often at the point where the head hits an object or where an object, such as a bullet, enters the brain.

In warfare, TBI can be presented as penetrating wounds from high-velocity bullets and debris from explosions from improvised explosive devices (IEDs), including road side mines, or as diffuse brain injury due to blasts caused by IEDs. Similar injuries are suffered by civilians who are victims of terrorist bomb attacks, typically using IEDs. Due to the improved care at the frontline and speedy response to terrorist attacks, a larger proportion of victims suffering can be rescued. It was found, however, that despite continued efforts to hasten evacuation from the field and improve the management of explosion-related head trauma, the outcome of treatment is still far from satisfactory.

While treatment of head wounds immediately after injury has improved steadily in the past few decades, lingering effects such as disabilities are still likely after moderate and severe TBI [Kluger Y, et al. *J Am Coll Surg.* 2004;199:875-879]. It is now well understood that the primary injury of TBI is followed for hours and days by a process of secondary injury [Gaetz M. et al. *Clin Neurophysiol.* 2004;115:4-18; Sullivan PG, et al. *J Neurosci Res.* 2005;79:231-239]. Major factors contributing to this second wave of brain damage, include: excitatory amino acids such as glutamate, $Ca^{++}$ homeostasis, and reactive oxygen species (ROS) [Kluger et al., Gaetz et al]. Mitochondria are one of the cell organelles affected by secondary brain injury, and in particular the mitochondrial permeability transition pore (MPTP) appears to take a central role among the factors leading to neuronal cell death with secondary brain injury [Kluger et al., Gaetz et al]. This suggests that targeting the MPTP, immediately after sustained brain injury, would have significant therapeutic implications for TBI.

The MPTP consists of three components which are identical to those described for the peripheral-type benzodiazepine receptor (PBR). PBR are present in peripheral tissues, and also in brain cells. The MPTP/PBR-complex, which is located in the mitochondrial membrane, is composed of three protein components: the 18-kDa isoquinoline binding protein (IBP), the 32-kDa voltage dependent anion channel (VDAC), and the 30-kDa adenine nucleotide transporter (ANT) (FIG. 1). In situ, the PBR/MPTP-complex is composed of several 18-kDa IBP components for each VDAC molecule (see FIG. 1). Functions for this receptor complex include involvement in apoptosis, ischemia, regulation of the mitochondrial membrane potential, mitochondrial respiration, steroidogenesis, immune responses of the cardiovascular system, cell proliferation, and cancer.

The PBR-complex binds specifically with the benzodiazepine Ro5 4864 (4'-chlorodiazepam) and the isoquinoline carboxamide derivative PK 11195 (FIG. 2), but not the central benzodiazepine receptor ligand clonazepam [Veenman L et al. *Pharmacol. Ther.* 2005;[E-pub ahead of print]. Later, to these classical PBR ligands, a new class of compounds, the 2 aryl-3-indoleacetamides (FGIN-1), was found to potently (with nM affinity) and selectively bind to the PBR-complex [Veenman L et al 2005]. A representative example is FGIN-1-27 (with a $K_i$=4.4±0.1 nM, as measured by the displacement of [$^3$H]Ro5 4864 (FIG. 2).

Some of the applicants of the present invention and others have demonstrated that PBR levels increase in the brain after brain damage, including traumatic brain damage and epilepsy. It has also been shown that knockdown of PBR expression and PBR ligands can prevent cell death of glial cells, including apoptosis (FIG. 3A). Moreover, some of the applicants of the present invention have shown that classical PBR ligands can prevent neurodegeneration typically caused by excitatory amino acids [Veenman L et al. *J. Neurochem.* 2002; 80:917-927]. In particular, it was found that treatment with the PBR ligand, PK 11195, prevented the effects of kainic acid injections, including modulation of PBR composition and prevention of seizures [Veenman L et al. 2002]. This protective effect of PBR ligands against neurodegeneration was later confirmed in other studies [Ryu J. K et al. Neurobiol. Dis. 20:550-561, Veiga S et al. *J Neurosci Res. Apr.* 1, 2005; 80(1):129-37]. All of the above studies suggest that PBR may form prime targets to treat and prevent secondary brain injury following TBI, including their consequences such as disability and epilepsy. PBR ligands may modulate apoptosis by causing changes in mitochondrial membrane potential via opening of the MPTP i.e. the VDAC component of the PBR-complex. This precedes and initiates a cascade including cytochrome c and caspases 9 and 3 leading to apoptosis.

It has also been found using genetic manipulation studies, that knockdown of the IBP component of the PBR-complex in the C6 glial cell line completely prevented apoptosis induced by the PBR ligand, FGIN-1-27 (FIG. 3A), as well as by non-PBR ligands, such as the anticancer agent, ErPC (FIG. 3B). Furthermore, knockdown of the IBP component of the PBR-complex reduced basal levels of apoptosis. Moreover, knockdown of the IBP component of the PBR-complex in the C6 glial cell line completely prevented apoptosis caused by a major contributor of neuronal cell death, the excitatory amino acid glutamate, and by one of the causative agents for the neuronal cell death in the neurodegenerative disease of Alzheimer, Abeta(1-42). This indicates that the IBP component of the PBR-complex plays an essential role in the induction of apoptosis, which is one of cellular processes leading the neuronal cell death. Substantiating this finding, the applicants of the present invention have shown that opening of the MPTP component of the MPTP/PBR complex by the ErPC requires IBP (FIG. 4). This indicates that IBP can serve to modulate the activity of VDAC and ANT i.e. the MPTP, and consequently modulate the mitochondrial apoptosis pathway.

Additional data resulting from knockdown of the ANT2 component of the MPTP/PBR-complex showed that this component also is required to induce apoptosis by ErPC. Furthermore, it was found that overexpression of the VDAC component of the MPTP/PBR-complex reduced the mitochondrial membrane potential. Overall, the data show that the major components to the MPTP/PBR-complex appear to play important roles in the induction of apoptosis.

It has also been shown by the applicants of the present invention, that the classical PBR ligands, PK 11195 and Ro5 4864, can prevent apoptotic cell death induced by strong pro-apoptotic agents [Kugler W et al. Abstracts of the 14th Annual Meeting of the Israel Society for Neuroscience, and the Joint Germany-Israel Meeting, Eilat, Israel, 2005;16: S38]. Thus, their effects are similar to those of knockdown of PBR components. Therefore, these PBR ligands can be considered weak or strong antagonists to PBR. In contrast, FGIN-1-27 can be considered to be an agonist [Veenman L et al. 2005]. However, pro-apoptotic effects of PK 11195 and Ro5 4864 are also reported, in particular at high concentrations, which are not due to their interaction with PBR, but may be caused by their effects on plasma membrane calcium channels [Veenman L et al. 2005]. Given the important effects on the life essential functions of PBR, several new PBR ligands have been developed [Veenman L et al. 2005]. Extensive structure-activity relationship studies of known PBR ligands revealed that their effects are affected by very slight structural modifications [Veenman L et al. 2005]. Based on the results of these structure-activity relationship studies, several different structures were elaborated such as 2-aryl substituted benzofuran-3-acetamide derivatives and also several isoquinolines [Benavides J et al. *J Neurochem* 1983;41:1744-1750], imidazopyridines [Langer S Z et al. *Pharmacologicol Biochein Behav* 1988;29:763-766], and pyrrolobenzoxazepine (1 in FIG. 5) [Campiani G, et al. *J Med Chem* 1996; 39:3435-3450]. According to these models, the receptor binding site provides a hydrogen bond-donating function ($H_1$) and two lipophilic pockets (L1 and L2) for all these ligands. The presence of an additional lipophilic region (L3) within the receptor has been deduced from these analyses (FIG. 4).

Although the molecules mentioned above (Ro5 4864, PK 11195, FGIN-1-27 and pyrrolobenzoxazepine) seem to be structurally very different, closer inspection reveals a number of common structural features which may be necessary for the efficacy of these ligands. These common features are listed below and presented in FIGS. 5 and 6:

1) The central core, designated to $L_1$ in FIG. 5, (central carbocycle, $C_2$ to $C_6$) always has an additional aromatic ring ($C_7$ to $C_{10}$ or $C_{11}$) attached to it.
2) An aryl ring, designated to $L_2$ in FIG. 5, which may sometimes have a halogen or a second aromatic ring (naphtyl) attached in $C_4'$ or $C_2'$ (see $C_1'$ to $C_6'$ in FIG. 6 for all the compounds).
3) This aryl ring is always linked to a double bond designated to L1 (FIG. 5) ($C_5$-$C_4$ for Ro5 4864 and PK 11195 and $C_5$-$C_3$ for FGIN-1-27 and pyrrolobenzoxazepine) (FIG. 6), while $C_4$ in this aryl ring is always substituted by a heteroatom (nitrogen in Ro5 4864, PK 11195 and FGIN-1-27, and oxygen in pyrrolobenzoxazepine).
4) All carbocycles are planar (FIG. 6) and therefore no stereogenic centers are needed for the recognition.
5) An amide link (designated to $L_3$ in FIG. 5) is always present in the carbon skeleton either included in the carbocycle, as in Ro5 4864, or outside the carbocycle in PK 11195, FGIN-1-27 and pyrrolobenzoxazepine (FIG. 6).

6) The same amide link also provides for the hydrogen bond-donating function ($H_1$, in FIG. 5), responsible for the hydrogen bond formation inside the IBP binding site.

U.S. Pat. No. 6,765,006 discloses quinazolines and other heterocycles which are antagonists or positive modulators of AMPA receptors, and the use thereof for treating, preventing or ameliorating neuronal loss or treating or ameliorating neurodegenerative diseases.

A need in the art exists to develop novel agents which bind more selectively to PBR than current PBR ligands and which prevent brain cell death, including apoptosis, as it occurs due to TBI and/or neurodegenerative diseases.

SUMMARY OF THE INVENTION

The present invention relates to novel phthalazine derivatives of formula I, quinazoline derivatives of formula II, quinoxaline derivatives of formula III, and dimers and multimers of any of formula IV-XI, pharmaceutical compositions containing the compounds, and their therapeutic use in treating and preventing brain damage resulting from traumatic brain injuries (TBI), and in treating and preventing neurodegenerative diseases. The compounds of the invention, especially the compounds of formula 19b, 12b and 24d, as defined herein, bind to peripheral-type benzodiazepine receptor (PBR), reduce basal apoptotic levels in neuronal cells, as well as reduce apoptosis induced by glutamate, which is known to be an important agent causing secondary brain damage after traumatic brain damages, and also takes part in neurodegenerative diseases. As such, the compounds of the invention are useful in the treatment and prevention of brain damage resulting from brain injury, especially secondary brain injury due to traumatic brain injury associated with, e.g., warfare, automobile accidents, sports injuries, violent crimes, household accidents, child abuse, gun shot wounds, etc. The compounds of the invention are also useful in treating and preventing neurodegenerative diseases such as Alzheimer Disease, Parkinson's Disease, Huntington's disease, and others.

In a preferred embodiment, the compounds of the invention bind more selectively to PBR than current PBR ligands do and prevent brain cell death, including apoptosis, as it occurs due to TBI and/or neurodegenerative diseases. In another preferred embodiment, the novel compounds easily cross the blood brain barrier, an advantageous property for the prevention of brain cell death.

In one embodiment pertaining to the treatment of secondary brain damage resulting from TBI, pharmaceutical compositions comprising the compounds of the invention can be carried by soldiers and paramedics and used in the battle field and/or on the site of terrorist attacks to prevent secondary injury resulting from TBI.

Thus, in one embodiment, the present invention provides a compound represented by the structure of formula I:

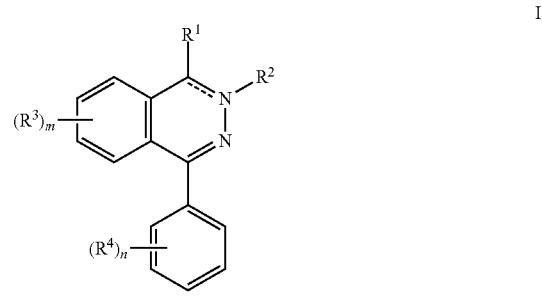

wherein

R¹ is oxo, R² is a group of the formula A and ⁓ is a single bond; or

R¹ is a group of the formula A, R² is absent and ⁓ is a double bond

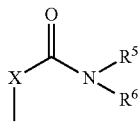

R³ and R⁴ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

R⁵ and R⁶ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, NR⁷ and —CR⁸R⁹, wherein R⁷, R⁸ and R⁹ are independently selected from the group consisting of hydrogen and a linear or branched $C_1$-$C_6$ alkyl;

m is 0, 1, 2, 3 or 4; and n is 0, 1, 2, 3, 4 or 5;

including salts, hydrates, solvates, polymorphs, optical isomers, geometrical isomers, enantiomers, diastereomers, and mixtures thereof.

In one currently preferred embodiment, the compound is represented by the structure of formula I, wherein R⁵ and R⁶ are each independently selected from the group consisting of methyl, ethyl, propyl, isopropyl, n-butyl, sec-butyl, isobutyl and tert-butyl. In another currently preferred embodiment, the compound is represented by the structure of formula I, wherein m and n are each 0. In another currently preferred embodiment, the compound is represented by the structure of formula I, wherein X is a bond. In another currently preferred embodiment, the compound is represented by the structure of formula I, wherein X is O. In another currently preferred embodiment, the compound is represented by the structure of formula I, wherein X is CH₂.

One embodiment of the compound of formula I is represented by the structure of formula IA.

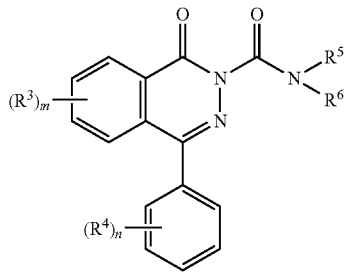

Specific examples of the compound of formula IA include, but are not limited to:

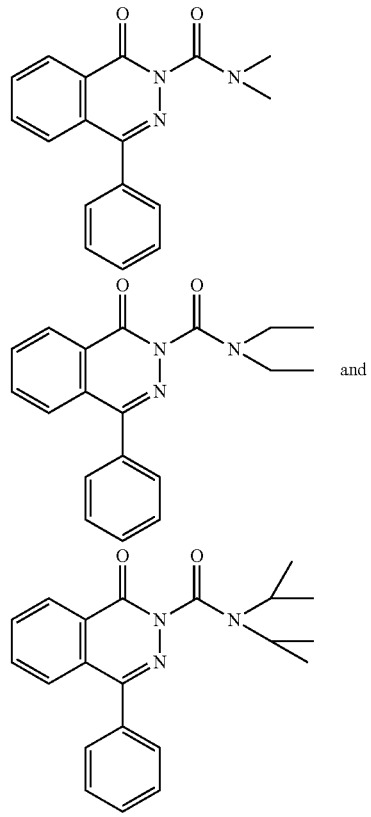

A currently preferred compound is a compound of 19b:

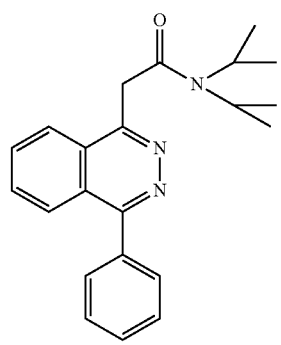

Another embodiment of the compound of formula I is represented by the structure of formula IB.

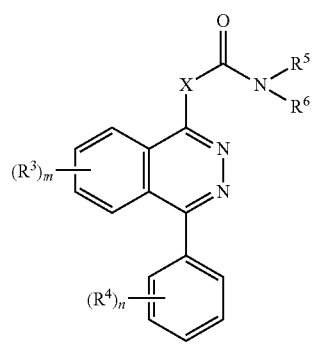

In one currently preferred embodiment, the compound is represented by the structure of formula IB, wherein X is a bond. In another currently preferred embodiment, the compound is represented by the structure of formula IB, wherein X is O. In another currently preferred embodiment, the compound is represented by the structure of formula IB, wherein X is CH$_2$.

Specific examples of the compound of formula IB include, but are not limited to:

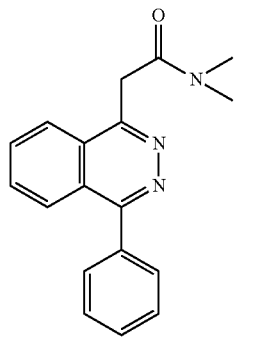

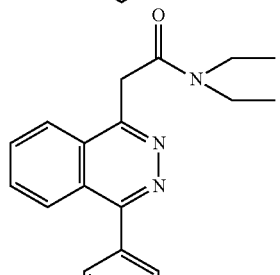

and

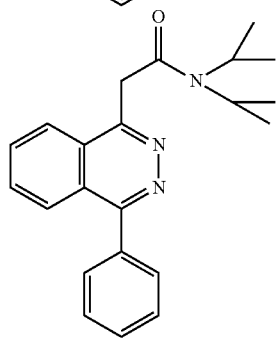

In another embodiment, the present invention provides a compound represented by the structure of formula II:

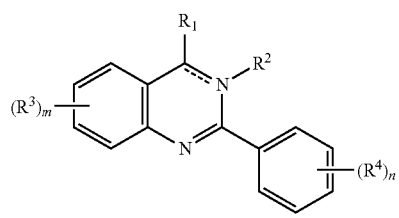

II wherein
R$^1$ is oxo, R$^2$ is a group of the formula A and $\doublebond$ is a single bond; or R$^1$ is a group of the formula A, R$^2$ is absent and $\doublebond$ is a double bond

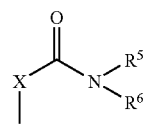

A

R$^3$ and R$^4$ are each independently selected from the group consisting of a linear or branched C$_1$-C$_6$ alkyl, a linear or branched C$_2$-C$_6$ alkenyl, a C$_3$-C$_8$ cycloalkyl, heterocyclyl, aryl, heteroaryl, halo, hydroxy, alkoxy, aryloxy, amino, cyano and nitro;

R$^5$ and R$^6$ are each independently selected from the group consisting of hydrogen, a linear or branched C$_1$-C$_6$ alkyl, a linear or branched C$_2$-C$_6$ alkenyl, a C$_3$-C$_8$ cycloalkyl, heterocyclyl, aryl and heteroaryl;

X is selected from the group consisting of a bond, —O—, —S—, —NR$^7$ and —CR$^8$R$^9$, wherein R$^7$, R$^8$ and R$^9$ are independently selected from the group consisting of hydrogen and a linear or branched C$_1$-C$_6$ alkyl;

m is 0, 1, 2, 3 or 4; and
n is 0, 1, 2, 3, 4 or 5;
including salts, hydrates, solvates, polymorphs, optical isomers, geometrical isomers, enantiomers, diastereomers, and mixtures thereof.

In one currently preferred embodiment, the compound is represented by the structure of formula II, wherein R$^5$ and R$^6$ are each independently selected from the group consisting of methyl, ethyl, propyl, isopropyl, n-butyl, sec-butyl, isobutyl and tert-butyl. In another currently preferred embodiment, the compound is represented by the structure of formula II, wherein m and n are each 0. In another currently preferred embodiment, the compound is represented by the structure of formula II, wherein X is CH$_2$. In another currently preferred embodiment, the compound is represented by the structure of formula II, wherein X is a bond. In another currently preferred embodiment, the compound is represented by the structure of formula II, wherein X is O.

One embodiment of the compound of formula II is represented by the structure of formula IIA.

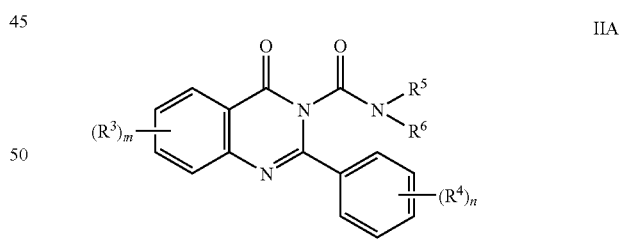

IIA

Specific examples of the compound of formula IIA include, but are not limited to:

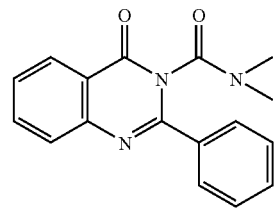

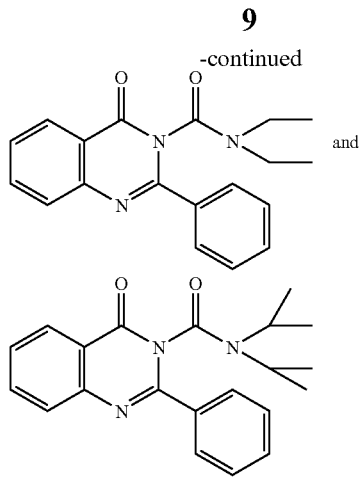

and

Another embodiment of the compound of formula II is represented by the structure of formula IIB.

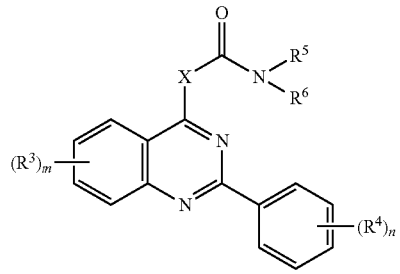

IIB

In one currently preferred embodiment, the compound is represented by the structure of formula IIB, wherein X is a bond. In another currently preferred embodiment, the compound is represented by the structure of formula IIB, wherein X is O. In another currently preferred embodiment, the compound is represented by the structure of formula IIB, wherein X is $CH_2$.

Specific examples of the compound of formula IIB include, but are not limited to:

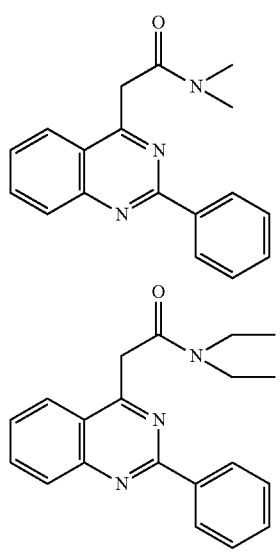

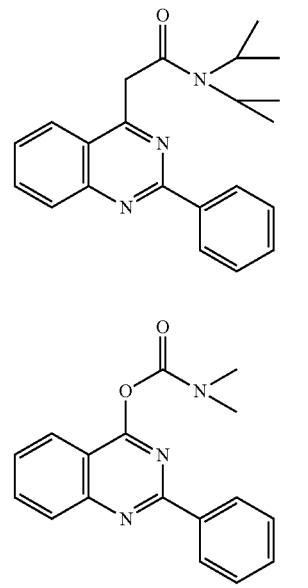

and

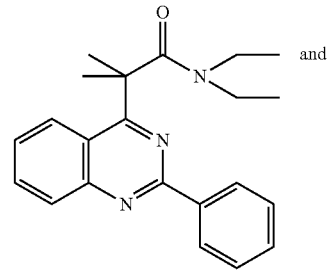

A currently preferred compound of formula IIB is represented by the structure of compound 12b:

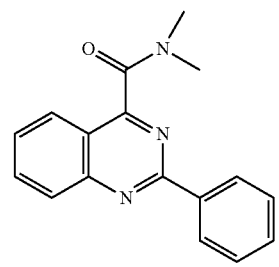

12b

In another embodiment, the present invention provides a compound represented by the structure of formula III:

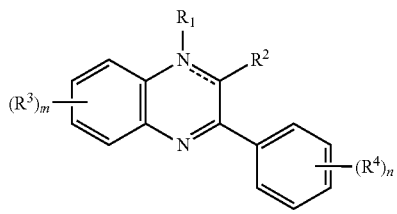

III wherein

R¹ is absent, R² is a group of the formula A and ═ is a double bond; or

R¹ is a group of the formula A, R² oxo and ═ is a single bond;

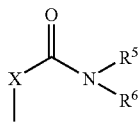

A

R³ and R⁴ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

R⁵ and R⁶ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, —NR⁷ and —CR⁸R⁹, wherein R⁷, R⁸ and R⁹ are independently selected from the group consisting of hydrogen and a linear or branched $C_1$-$C_6$ alkyl;

m is 0, 1, 2, 3 or 4; and n is 0, 1, 2, 3, 4 or 5;

including salts, hydrates, solvates, polymorphs, optical isomers, geometrical isomers, enantiomers, diastereomers, and mixtures thereof.

In one currently preferred embodiment, the compound is represented by the structure of formula III, wherein R⁵ and R⁶ are each independently selected from the group consisting of methyl, ethyl, propyl, isopropyl, n-butyl, sec-butyl, isobutyl and tert-butyl. In another currently preferred embodiment, the compound is represented by the structure of formula III, wherein m and n are each 0. In one currently preferred embodiment, the compound is represented by the structure of formula III, wherein X is a bond. In another currently preferred embodiment, the compound is represented by the structure of formula III, wherein X is O. In another currently preferred embodiment, the compound is represented by the structure of formula III, wherein X is $CH_2$.

One embodiment of the compound of formula III is represented by the structure of formula IIIA.

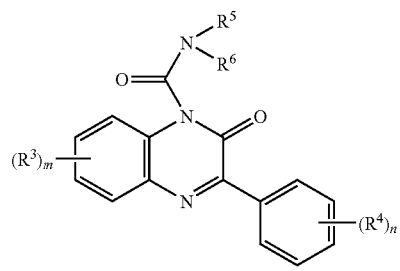

IIIA

Specific examples of the compound of formula IIIA include, but are not limited to:

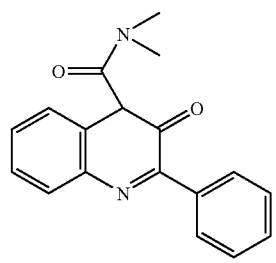

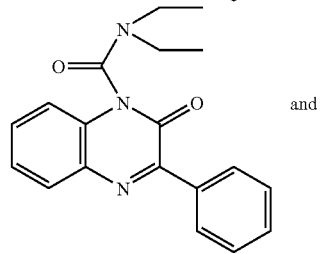

and

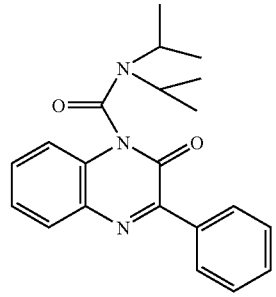

Another embodiment of the compound of formula III is represented by the structure of formula IIIB.

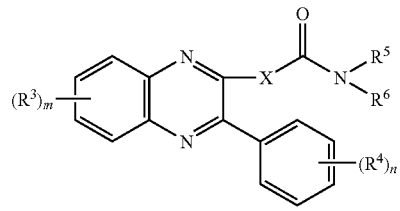

IIIB

In one currently preferred embodiment, the compound is represented by the structure of formula IIIB, wherein X is a bond. In another currently preferred embodiment, the compound is represented by the structure of formula IIIB, wherein X is O. In another currently preferred embodiment, the compound is represented by the structure of formula IIIB, wherein X is $CH_2$.

Specific examples of the compound of formula IIIB include, but are not limited to:

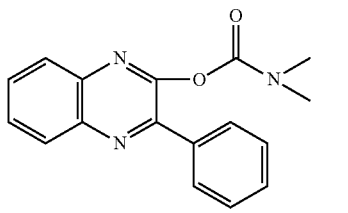

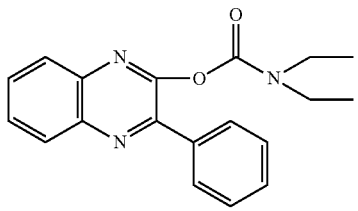

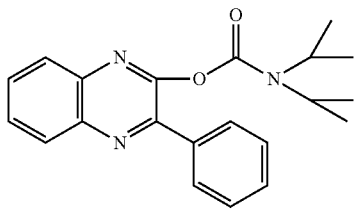

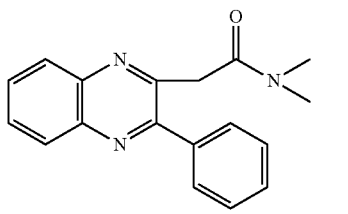

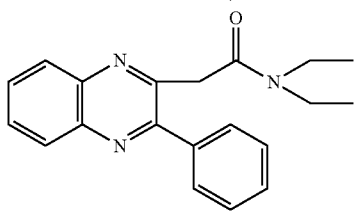

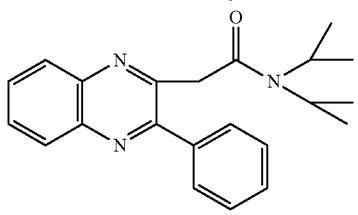

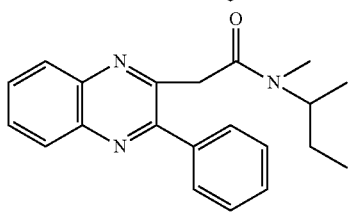

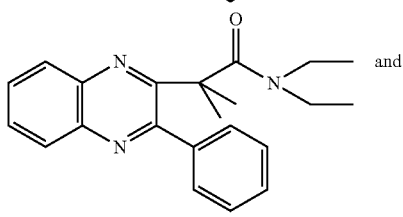

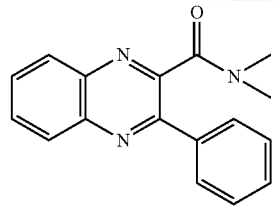 [SMILES: CN(C)C(=O)c1nc2ccccc2nc1-c1ccccc1]

In another aspect, the present invention contemplates dimeric, oligomeric or polymeric derivatives comprising a plurality of covalently linked PBR ligands, separated by a linker. Without wishing to be bound by any particular mechanism or theory, it is believed that the presence of more than one PBR binding moiety in the same molecule may increase the local concentration of the active moiety at the target site, thereby increasing potency of the compound.

Thus, in one embodiment, the present invention provides polyvalent compounds comprising two or more PBR binding molecules (PBR ligands), represented by the structure of formula IV:

$$(A)_p\text{-}Y \qquad \qquad IV$$

wherein each A is independently of the other a moiety which binds to the PBR, p is an integer of 2-6 and Y is a linker. The number of PBR ligand units in formula IV (represented by the integer p) depends on the valency of the linker, and is generally selected from the group consisting of 2, 3, 4, 5 and 6.

The PBR ligand can be a classical ligand such as PK 11195, Ro5 4864, pyrrolobenzoxazepine, FGIN 1-27, 3 Alpidem, SSR 180575, or any other known PBR ligand. Alternatively, the PBR ligand can be any one or more of the compounds of the present invention, i.e., a compound of formula I, II or III, or any combination thereof.

The linker can be, for example, unsubstituted or substituted $C_1$-$C_{12}$ alkylene, polyoxy $C_1$-$C_{12}$ alkylene, polyamino $C_1$-$C_{12}$ alkylene, polythio $C_1$-$C_{12}$ alkylene, polyamide, polyester, a sugar moiety, —NH—, —S—, —OR$^{10}$—, —NHR$^{11}$— and —SR$^{12}$—, wherein R$^{10}$, R$^{11}$ and R$^{12}$ are each independently unsubstituted or substituted $C_1$-$C_{12}$ alkylene Representative and non limiting examples include:

A. Phthalazines

A compound of any of formula V, VA and VB

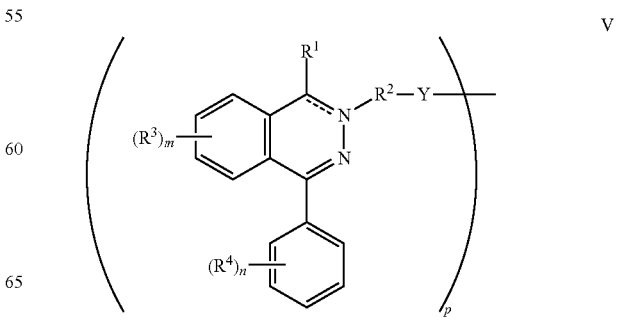

-continued

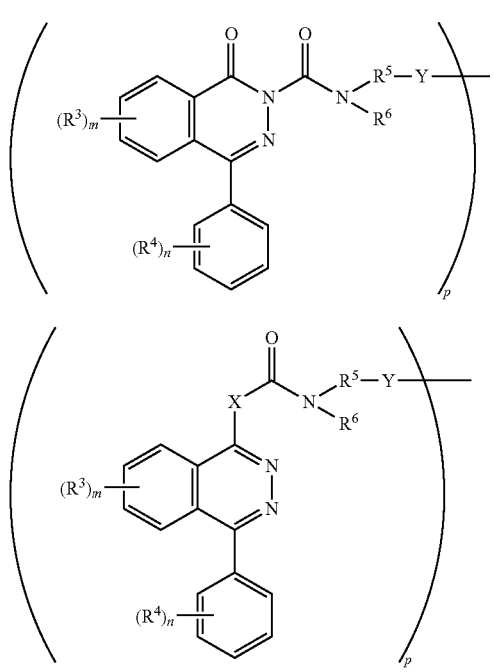

VA

VB wherein
R[1] is oxo, R[2] is a group of the formula A and ⎓ is a single bond; or
R[1] is a group of the formula A, R[2] is absent and ⎓ is a double bond

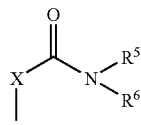

A

R[3] and R[4] are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;
R[5] is selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;
R[6] is selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;
X is selected from the group consisting of a bond, —O—, —S—, —NR[7] and —CR[8]R[9], wherein R[7], R[8] and R[9] are independently selected from the group consisting of hydrogen and a linear or branched $C_1$-$C_6$ alkyl;
Y is a linker moiety;
m is 0, 1, 2, 3 or 4;
n is 0, 1, 2, 3, 4 or 5; and
p is 2, 3, 4, 5 or 6;
including salts, hydrates, solvates, polymorphs, optical isomers, geometrical isomers, enantiomers, diastereomers, and mixtures thereof.

B. Quinazolines
A compound of any of formula VI, VIA and VIB

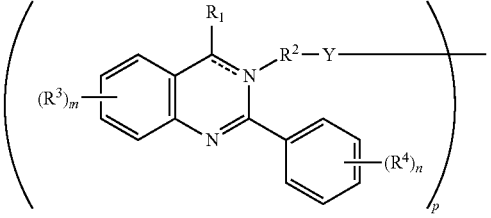

VI

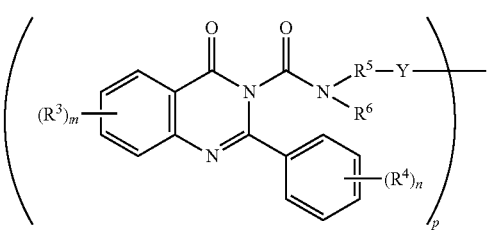

VIA

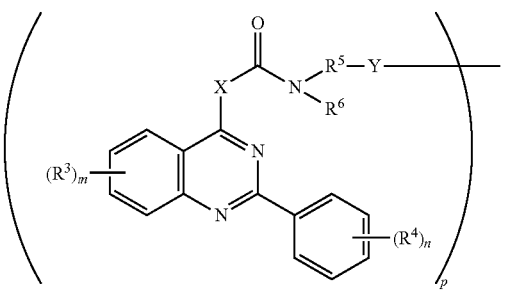

VIB wherein
R[1] is oxo, R2 is a group of the formula A and ⎓ is a single bond; or
R[1] is a group of the formula A, R[2] is absent and ⎓ is a double bond

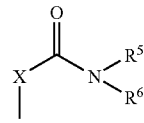

A

R[3] and R[4] are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;
R[5] is selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;
R[6] is selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;
X is selected from the group consisting of a bond, —O—, —S—, —NR[7] and —CR[8]R[9], wherein R[7], R[8] and R[9] are independently selected from the group consisting of hydrogen and a linear or branched $C_1$-$C_6$ alkyl;

Y is a linker moiety;
m is 0, 1, 2, 3 or 4;
n is 0, 1, 2, 3, 4 or 5; and
p is 2, 3, 4, 5 or 6;
including salts, hydrates, solvates, polymorphs, optical isomers, geometrical isomers, enantiomers, diastereomers, and mixtures thereof.

C. Quinoxalines

A compound of any of formula VII, VIIA and VIIB

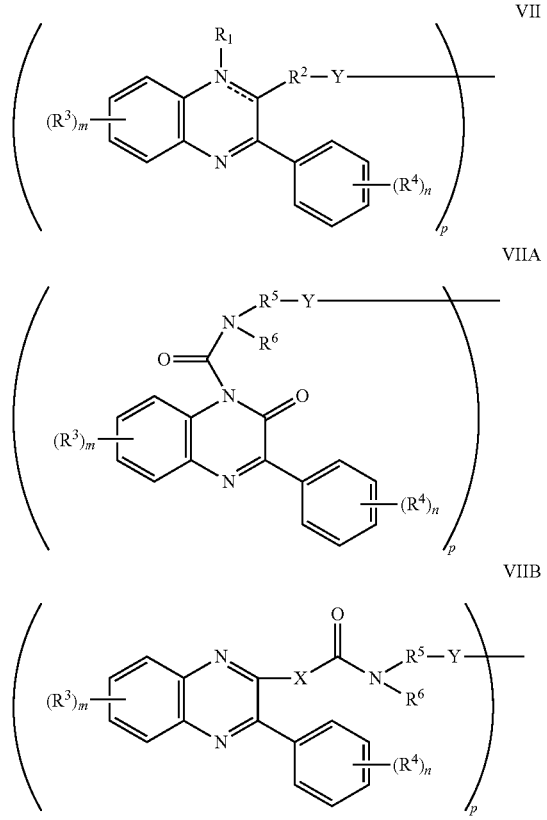

wherein
$R^1$ is absent, $R^2$ is a group of the formula A and ═ is a double bond; or
$R^1$ is a group of the formula A, $R^2$ oxo and ═ is a single bond;

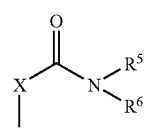

$R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;
$R^5$ is selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;
$R^6$ is selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;
X is selected from the group consisting of a bond, —O—, —S—, —$NR^7$ and —$CR^8R^9$, wherein $R^7$, $R^8$ and $R^9$ are independently selected from the group consisting of hydrogen and a linear or branched $C_1$-$C_6$ alkyl;
Y is a linker moiety;
m is 0, 1, 2, 3 or 4;
n is 0, 1, 2, 3, 4 or 5; and
p is 2, 3, 4, 5 or 6;
including salts, hydrates, solvates, polymorphs, optical isomers, geometrical isomers, enantiomers, diastereomers, and mixtures thereof.

It is apparent to a person of skill in the art that the multimeric compounds of the present invention should not be limited to the symmetric compounds described above. Asymmetric compounds including any combination of PBR ligands are also encompassed by the broad scope of the invention. For example, the multimeric compound can include any combination of phthalazine, quinazoline and quinoxaline moiety, as well as moieties of known PBR ligands. A person of skill in the art is capable of designing the appropriate combination of ligands, as desired.

In one currently preferred embodiment, the present invention provides dimeric compounds comprising two PBR binding molecules (PBR ligands) separated by a linker, wherein the dimer is represented by the structure of formula VIII:

A-Y—B  VII wherein A and B are independently of each other a moiety which binds to the PBR (PBR ligand) and Y is a linker, wherein the PBR ligand and linkers are as described above for the compounds of formula IV, V, VI and VII.

A currently preferred dimer is a dimer of PK 11195, designated compound 24;

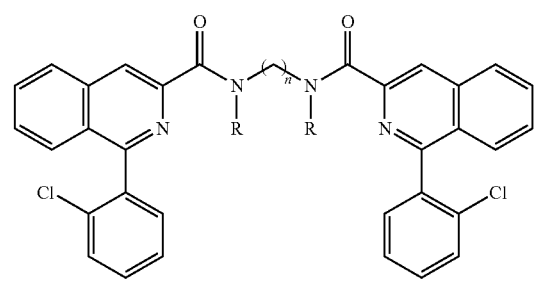

wherein n is an integer of from 1 to 12 and each R is independently selected from the group consisting of a hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl.

Specific embodiments of the compound of formula 24 include, but are not limited to: n is 2 and R is H (24a); n is 4 and R is H (24b); n is 2 and R is methyl (24c); n is 3 and R is methyl (24d); and n is 6 and R is methyl (24e). Currently preferred compounds are 24d and 24e.

Other currently preferred compounds are symmetric or asymmetric dimers of the quinazoline, quinoxaline and phthalazine derivatives of the present invention, and/or of known PBR ligands such as PK 11195, Ro5 4864, pyrrolobenzoxazepine, FGIN 1-27, 3 Alpidem and SSR 180575. Representative and non limiting examples include:

D. Phthalazines

A compound of any of formula IX, IXA and IXB:

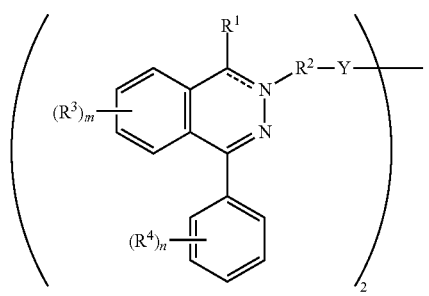

IX

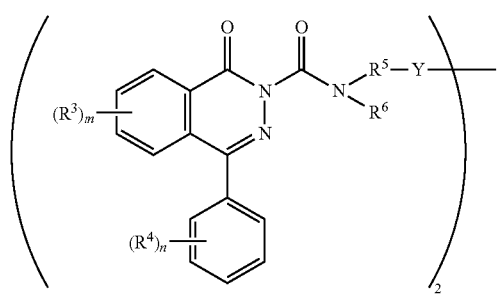

IXA

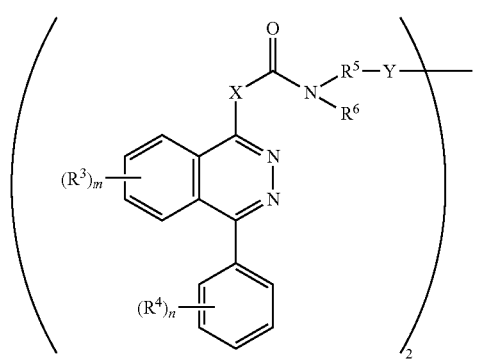

IXB wherein
$R^1$ is oxo, $R^2$ is a group of the formula A and ═ is a single bond; or
$R^1$ is a group of the formula A, $R^2$ is absent and ═ is a double bond

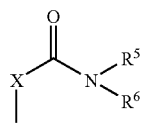

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;
$R^5$ is independently selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;

$R^6$ is independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;
X is selected from the group consisting of a bond, —O—, —S—, —NR$^7$ and —CR$^8$R$^9$, wherein R$^7$, R$^8$ and R$^9$ are independently selected from the group consisting of hydrogen and a linear or branched $C_1$-$C_6$ alkyl;
Y is a linker moiety;
m is 0, 1, 2, 3 or 4; and
n is 0, 1, 2, 3, 4 or 5;
including salts, hydrates, solvates, polymorphs, optical isomers, geometrical isomers, enantiomers, diastereomers, and mixtures thereof.

E. Quinazolines

A compound of any of formula X, XA and XB:

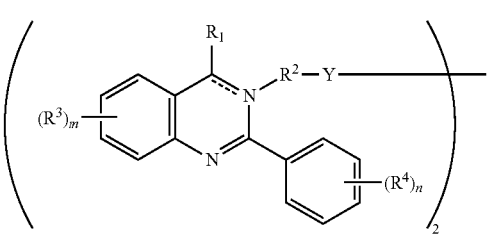

X

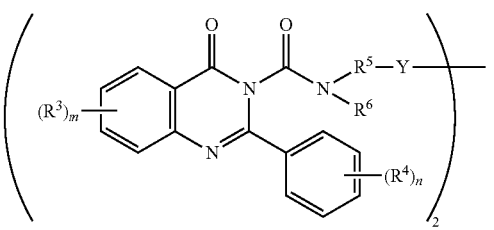

XA

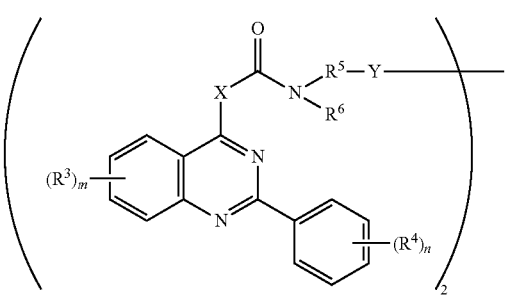

XB wherein
$R^1$ is oxo, $R^2$ is a group of the formula A and ═ is a single bond; or
$R^1$ is a group of the formula A, $R^2$ is absent and ═ is a double bond

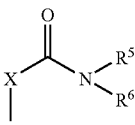

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

$R^5$ is independently selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;

$R^6$ is independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, —$NR^7$— and —$CR^8R^9$—, wherein $R^7$, $R^8$ and $R^9$ are independently selected from the group consisting of hydrogen and a linear or branched $C_1$-$C_6$ alkyl;

Y is a linker moiety;

m is 0, 1, 2, 3 or 4; and n is 0, 1, 2, 3, 4 or 5;

including salts, hydrates, solvates, polymorphs, optical isomers, geometrical isomers, enantiomers, diastereomers, and mixtures thereof.

F. Quinoxalines

A compound of any of formula XI, XIA and XIB:

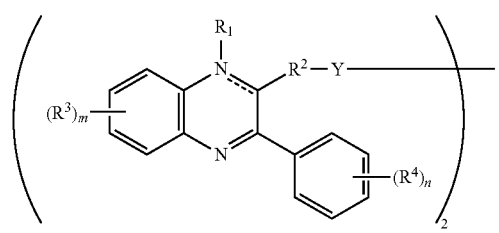

XI

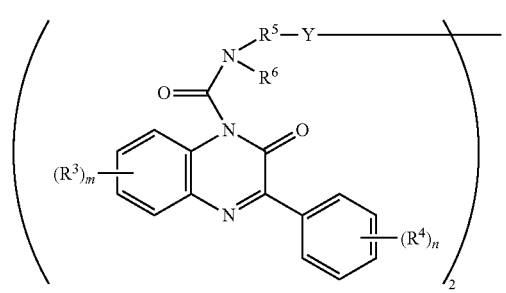

XIA

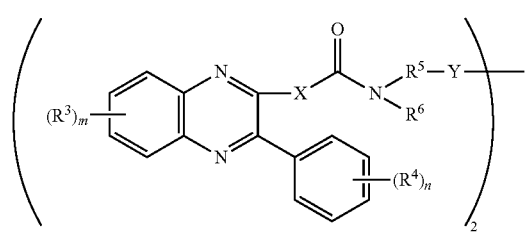

XIB wherein $R^1$ is absent, $R^2$ is a group of the formula A and ═ is a double bond; or $R^1$ is a group of the formula A, $R^2$ oxo and ─ is a single bond;

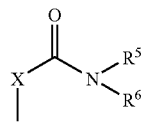

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

$R^5$ is independently selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;

$R^6$ is independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, —$NR^7$— and —$CR^8R^9$—, wherein $R^7$, $R^8$ and $R^9$ are independently selected from the group consisting of hydrogen and a linear or branched $C_1$-$C_6$ alkyl;

Y is a linker moiety;

m is 0, 1, 2, 3 or 4; and n is 0, 1, 2, 3, 4 or 5;

including salts, hydrates, solvates, polymorphs, optical isomers, geometrical isomers, enantiomers, diastereomers, and mixtures thereof.

It is apparent to a person of skill in the art that the dimeric compounds of the present invention should not be limited to the symmetric compounds described above. Asymmetric compounds including any combination of PBR ligands are also encompassed by the broad scope of the invention. For example, the dimeric compound can include any combination of phthalazine, quinazoline and quinoxaline moiety, as well as moieties of known PBR ligands. A person of skill in the art is capable of designing the appropriate combination of ligands, as desired.

The present invention also contemplates pharmaceutical compositions that include a pharmaceutically acceptable carrier and, as an active ingredient, one or more of the compounds of the invention, represented by any of formulas I-XI, as described above. Preferred compositions have as an active ingredient any one or more of the compounds represented by the structure IA, IB, IIA, IIB, IIIA, IIIB, VA, VB, VIA, VIB, VIIA, VIIB, IXA, IXB, XA, XB, XIA and XIB, or any of the structures recited hereinabove. A particularly preferred composition comprises a pharmaceutically acceptable carrier and, as an active ingredient, a compound of formula 19b. Another particularly preferred composition comprises a pharmaceutically acceptable carrier and, as an active ingredient, a compound of formula 12b. Another particularly preferred composition comprises a pharmaceutically acceptable carrier and, as an active ingredient, a compound of formula 24d. Another particularly preferred composition comprises a pharmaceutically acceptable carrier and, as an active ingredient, a compound of formula 24e.

The pharmaceutical compositions of the present invention can be provided in any form known in the art, for example in a form suitable for oral administration (e.g., a solution, a suspension, a syrup, an emulsion, a dispersion, a tablet, a pill, a capsule, a pellet, granules and a powder), for parenteral administration (e.g., intravenous, intramuscular, intraarterial, transdermal, subcutaneous or intraperitoneal), for topical administration (e.g., an ointment, a gel, a cream), for administration by inhalation, for rectal administration (e.g., administration via suppository) or for administration via dialysis.

The present invention additionally provides, in another embodiment, a method for treating or preventing brain damage resulting from brain injury, comprising the step of administering to a subject in need thereof an effective amount of a compound of formula I-XI, as described herein. Preferably, the compound is one or more of the compounds represented by the structure IA, IB, IIA, IIB, IIIA, IIIB, VA, VB, VIA, VIB, VIIA, VIIB, IXA, IXB, XA, XB, XIA and XIB, or any of the structures recited hereinabove. In some embodiments, the compound is administered in a pharmaceutical composition. Preferably, the compound is represented by the structure of formula 19b, formula 12b, and 24d.

In one embodiment, the brain injury is traumatic brain injury (TBI). As contemplated herein, the compounds of the invention are particularly useful for preventing and treating secondary brain damage resulting from TBI. Thus, the compounds of the invention are useful, e.g., for soldiers in the battlefield, especially soldiers who have suffered TBI. As such, secondary brain damage due to TBI can be treated or prevented by administering the compounds of the invention to soldiers, or by supplying paramedics in the battlefield with the compounds of the invention, so that the compounds can be administered on site as soon as possible after the soldier has suffered TBI. The compounds of the invention are also useful for civilians who are victims of violent crimes, including but not limited to, terrorist attacks. This may reduce the incidence of disability presently occurring in the aftermath of TBI suffered due to hostilities, including terrorist attacks.

The utility of the compounds of the invention is not limited to violent crimes such as warfare and terrorist attacks. The compounds of the invention are also useful for individuals suffering from brain injury due to domestic occurrences, such as automobile accidents, sports injuries, household accidents, child abuse, gun shot wounds, etc, including their consequences such as disability and epilepsy.

As mentioned above, the compounds of the invention reduce basal apoptotic levels in neuronal cells, as well as reduce apoptosis induced by glutamate, which is known to be an important agent in neurodegenerative pathways. As such, the compounds of the invention are also useful in treating and preventing neurodegenerative diseases. Examples of neurodegenerative diseases include, but are not limited to, Alzheimer Disease, Pick's disease, diffuse Lewy body disease, progressive supranuclear palsy (Steel-Richardson syndrome), multisystem degeneration (Shy-Drager syndrome), motor neuron diseases, amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases, Creutzfeldt-Jakob, Gerstmann-Straussler-Scheinker disease, Kuru and fatal familial insomnia.

The present invention also relates to the use of a compound of Formula I-XI in the manufacture of a medicament for treating or preventing brain damage resulting from brain injury: In a currently preferred embodiment, the present invention relates to the use of compound 19b in the manufacture of a medicament for treating or preventing brain damage resulting from brain injury. In another currently preferred embodiment, the present invention relates to the use of compound 12b in the manufacture of a medicament for treating or preventing brain damage resulting from brain injury. In another currently preferred embodiment, the present invention relates to the use of compound 24d in the manufacture of a medicament for treating or preventing brain damage resulting from brain injury.

The present invention also relates to the use of a compound of Formula I-XI in the manufacture of a medicament to for treating or preventing neurodegenerative diseases. In a currently preferred embodiment, the present invention relates to the use of compound of 19b in the manufacture of a medicament to for treating or preventing neurodegenerative diseases. In a currently preferred embodiment, the present invention relates to the use of compound of 12b in the manufacture of a medicament to for treating or preventing neurodegenerative diseases. In a currently preferred embodiment, the present invention relates to the use of compound of 24d in the manufacture of a medicament to for treating or preventing neurodegenerative diseases.

In contrast to problems seen with classical PBR ligands, the compounds of the invention are not as toxic at high concentrations. Furthermore, the compounds of the invention do not enhance apoptotic levels of apoptosis inducers such as glutamate, as classical PBR ligands may do. As such, the compounds of the invention are particularly advantageous as compared with classical PBR ligands. These characteristics suggest that the compounds may have neuroprotective properties and can be used to treat and prevent secondary brain damage after brain surgery, and neurodegenerative diseases.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PRESENT INVENTION

Figure 1:
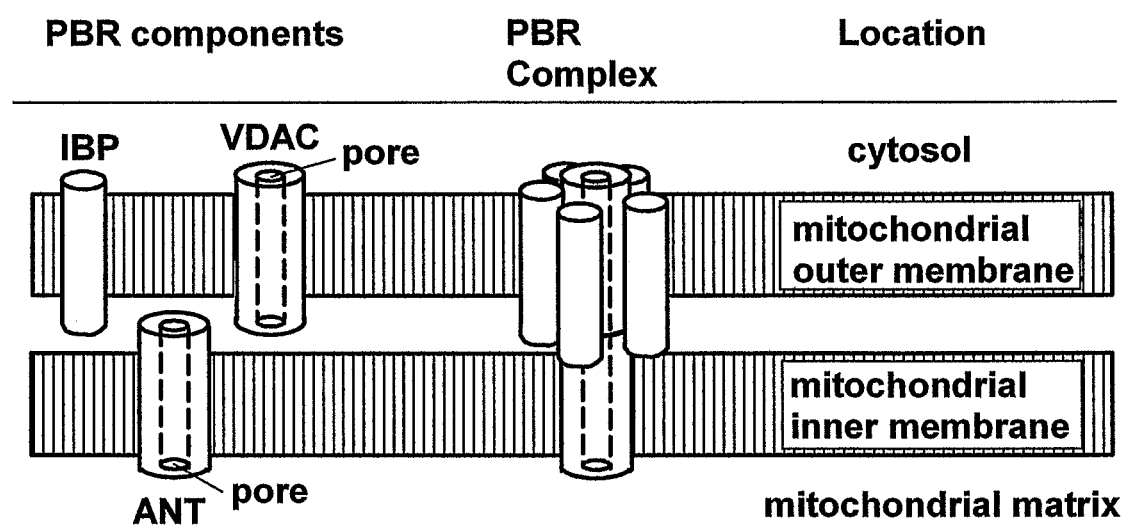
FIG. 1: Location of the PBR complex and its protein components in the mitochondrial membrane.
Figure 2:
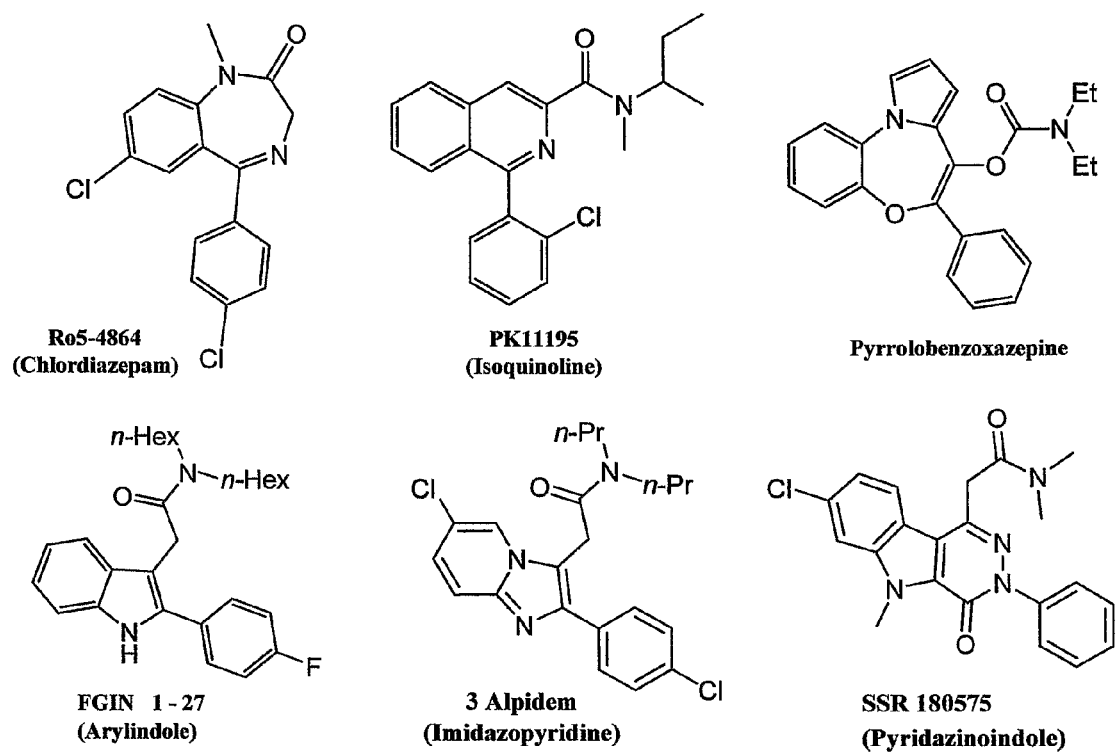
FIG. 2: Three commonly used PBR ligands.
Figure 3B:
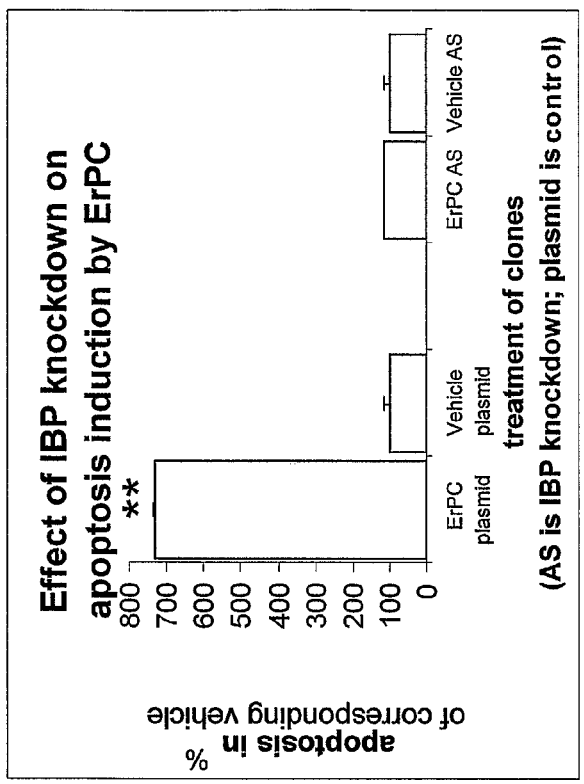
FIG. 3: A) Treatment with the PBR ligand, FGIN-1-27 ($10^{-5}$M), increased apoptotic levels in the C6 glioma cell line 2 fold in control cells (columns on the left side). B) Treatment with the antineoplastic agent, ErPC ($10^{-4}$M), increased apoptotic levels in the C6 glioma cell line 7-8 fold in control cells (columns on the left side). In the IBP knockdown cell line these apoptotic effects of FGIN-1-27 and ErPC were completely abolished.
Figure 3A:
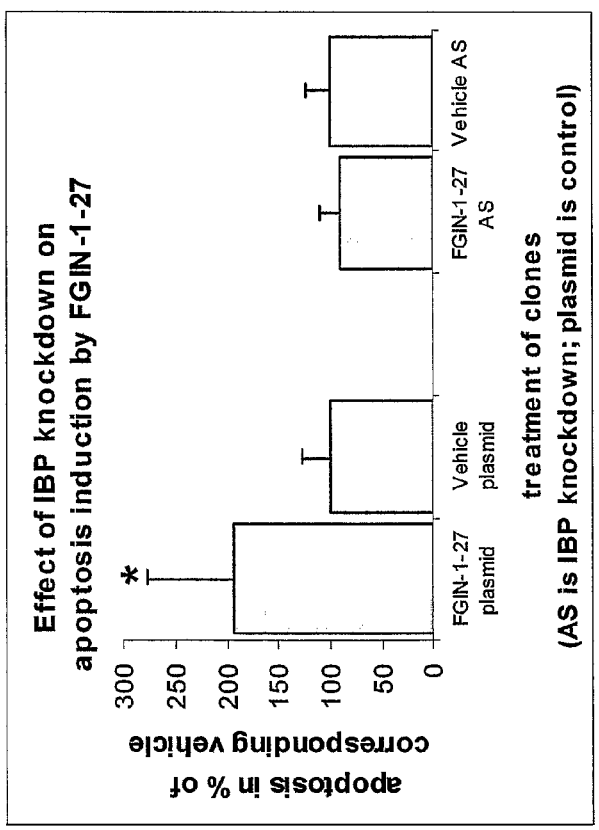
Figure 4:
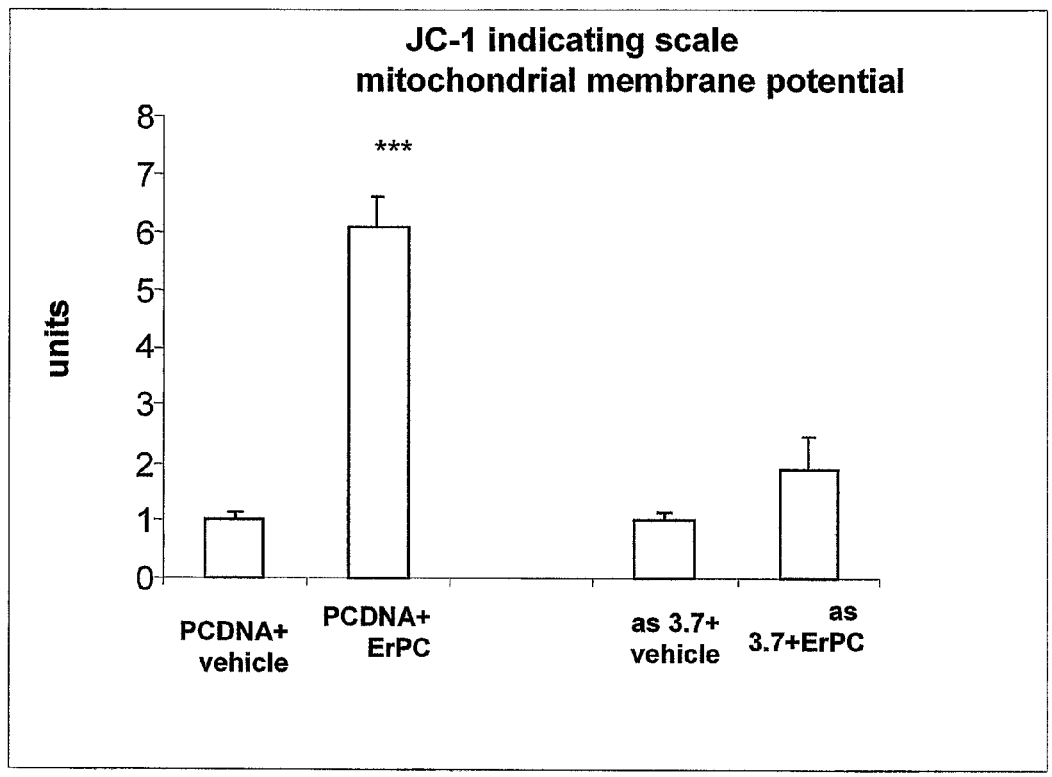
FIG. 4: Treatment with the antineoplastic agent, ErPC ($10^{-4}$M), enhanced mitochondrial membrane potential decrease in the C6 glioma cell line 6 fold in control cells, as compared to vehicle treated control cells. In the IBP knockdown cell line (as 3.7) these effects of ErPC on the mitochondrial potential were completely abolished. This indicates that the IBP component of the PBR/MPTP complex may serve to modulate the capacity of the pore formed by VDAC to open. This correlates well with prevention in IBP knockdown cells of apoptosis normally caused by ErPC (compare with FIG. 3B).
Figure 5:
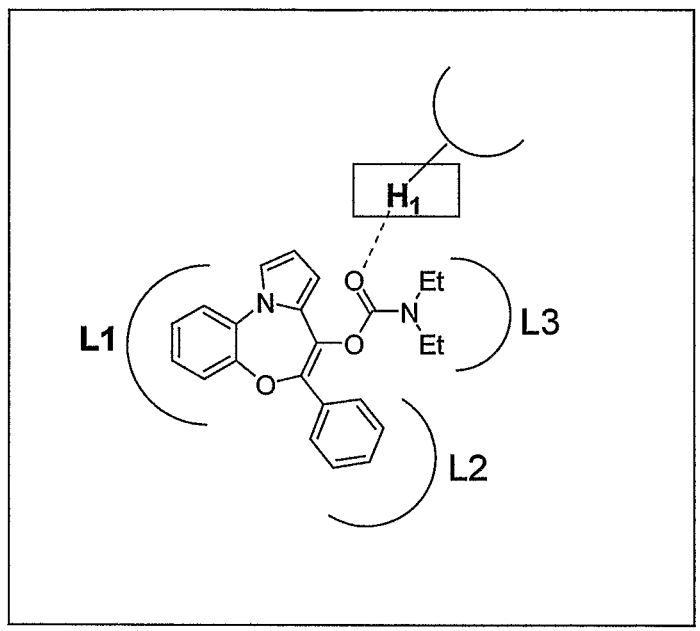
FIG. 5: Common features of PBR ligands: $H_1$ — a hydrogen bond-donating function, responsible for the hydrogen bond formation inside the IBP binding site; $L_1$-$L_3$-lipophilic pockets.
Figure 6:
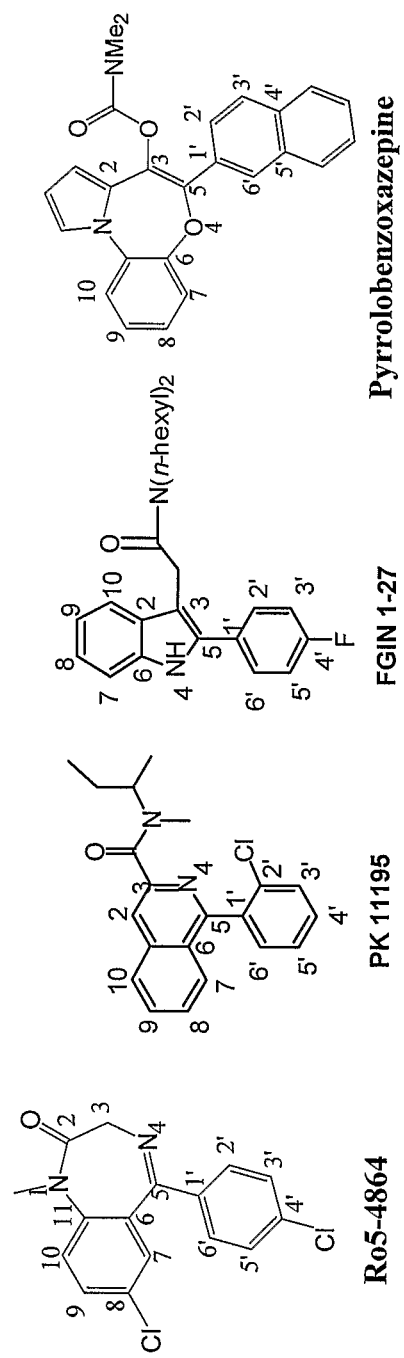
FIG. 6: Common features of Ro5 4864, PK 11195, FGIN-1-27 and pyrrolobenzoxazepine.

The present invention relates to novel phthalazine derivatives of formula I, quinazoline derivatives of formula II, quinoxaline derivatives of formula III, and dimeric and polymeric compounds of formula IV-XI, pharmaceutical compositions containing the compounds, and their therapeutic use in treating and preventing brain damage resulting from traumatic brain injuries (TBI), and in treating and preventing neurodegenerative diseases.

Compounds

In one embodiment, the present invention provides a compound represented by the structure of formula I:

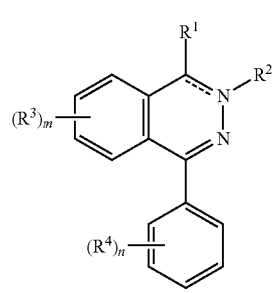

I wherein $R^1$ is oxo, $R^2$ is a group of the formula A and ⚌ is a single bond; or $R^1$ is a group of the formula A, $R^2$ is absent and ⚌ is a double bond

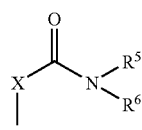

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

$R^5$ and $R^6$ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, $NR^7$ and —$CR^8R^9$, wherein $R^7$, $R^8$ and $R^9$ are independently selected from the group consisting of hydrogen and a linear or branched $C_1$-$C_6$ alkyl;

m is 0, 1, 2, 3 or 4; and n is 0, 1, 2, 3, 4 or 5;

including salts, hydrates, solvates, polymorphs, optical isomers, geometrical isomers, enantiomers, diastereomers, and mixtures thereof.

In one currently preferred embodiment, the compound is represented by the structure of formula I, wherein $R^5$ and $R^6$ are each independently selected from the group consisting of methyl, ethyl, propyl, isopropyl, n-butyl, sec-butyl, isobutyl and tert-butyl. In a particularly preferred embodiment, $R^5$ and $R^6$ are each isopropyl. In another currently preferred embodiment, the compound is represented by the structure of formula I, wherein m and n are each 0. In a particularly preferred embodiment, $R^5$ and $R^6$ are each isopropyl and m and n are each 0.

In another currently preferred embodiment, the compound is represented by the structure of formula I, wherein X is a bond. In another currently preferred embodiment, the compound is represented by the structure of formula I, wherein X is O. In another currently preferred embodiment, the compound is represented by the structure of formula 1, wherein X is $CH_2$.

One embodiment of the compound of formula I is represented by the structure of formula IA.

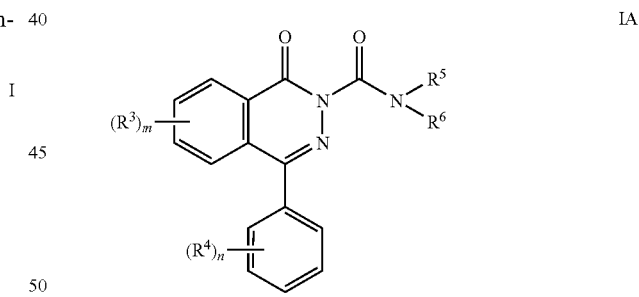

IA

Specific examples of the compound of formula IA include, but are not limited to:

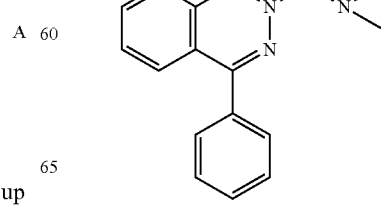

-continued

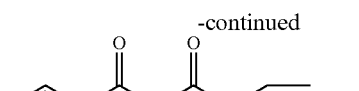
and

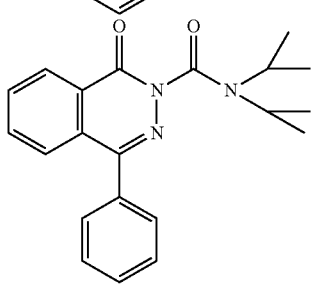

A currently preferred compound is a compound of formula (designated herein: compound 19b):

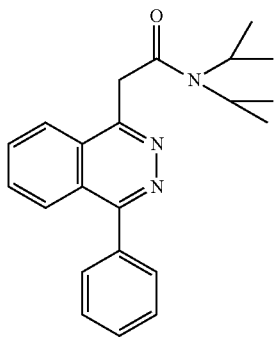 [SMILES: CC(C)N(C(=O)Cc1nnc(-c2ccccc2)c2ccccc12)C(C)C]

Another embodiment of the compound of formula I is represented by the structure of formula IB.

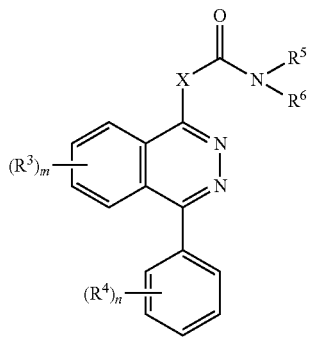

IB

In one currently preferred embodiment, the compound is represented by the structure of formula IB, wherein X is a bond. In another currently preferred embodiment, the compound is represented by the structure of formula IB, wherein X is O. In another currently preferred embodiment, the compound is represented by the structure of formula IB, wherein X is $CH_2$.

Specific examples of the compound of formula IB include, but are not limited to:

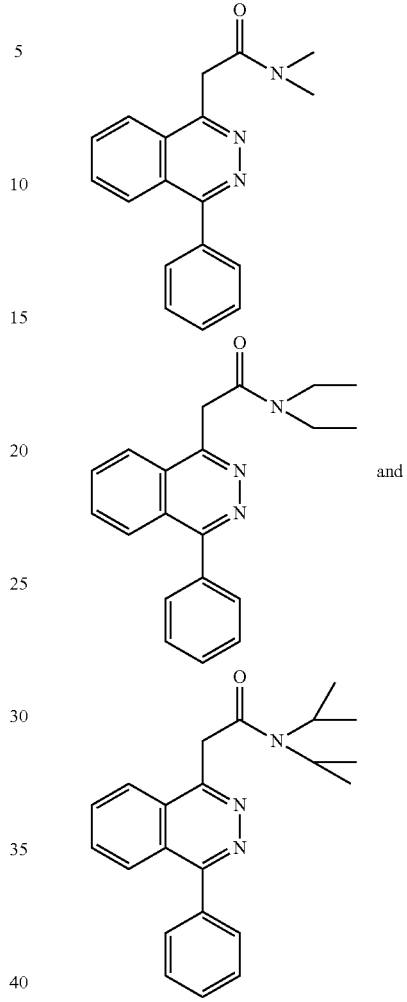

and

In another embodiment, the present invention provides a compound represented by the structure of formula II:

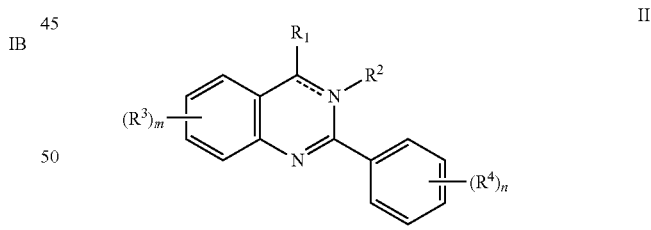

II wherein
$R^1$ is oxo, $R^2$ is a group of the formula A and ═ is a single bond; or
$R^1$ is a group of the formula A, $R^2$ is absent and ═ is a double bond

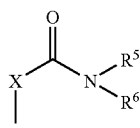

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

$R^5$ and $R^6$ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, —$NR^7$ and —$CR^8R^9$, wherein $R^7$, $R^8$ and $R^9$ are independently selected from the group consisting of hydrogen and a linear or branched $C_1$-$C_6$ alkyl;

m is 0, 1, 2, 3 or 4; and n is 0, 1, 2, 3, 4 or 5;

including salts, hydrates, solvates, polymorphs, optical isomers, geometrical isomers, enantiomers, diastereomers, and mixtures thereof.

In one currently preferred embodiment, the compound is represented by the structure of formula II, wherein $R^5$ and $R^6$ are each independently selected from the group consisting of methyl, ethyl, propyl, isopropyl, n-butyl, sec-butyl, isobutyl and tert-butyl. In another currently preferred embodiment, the compound is represented by the structure of formula II, wherein m and n are each 0. In another currently preferred embodiment, the compound is represented by the structure of formula II, wherein X is $CH_2$. In another currently preferred embodiment, the compound is represented by the structure of formula II, wherein X is a bond. In another currently preferred embodiment, the compound is represented by the structure of formula II, wherein X is O.

One embodiment of the compound of formula II is represented by the structure of formula IIA.

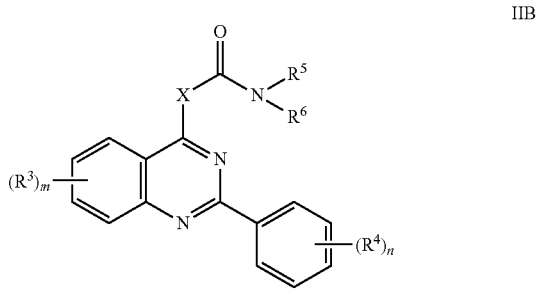

IIA

Specific examples of the compound of formula IIA include, but are not limited to:

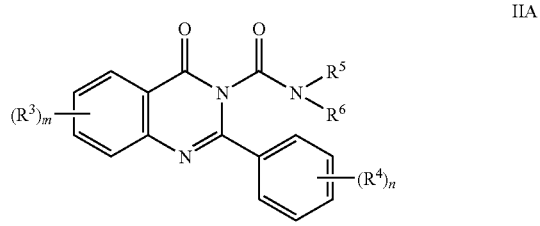

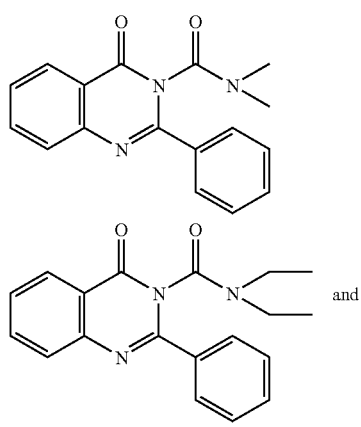

and

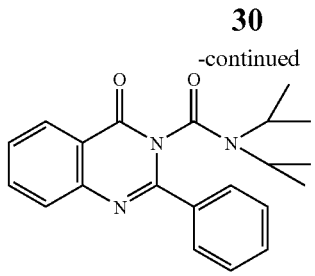

Another embodiment of the compound of formula II is represented by the structure of formula IIB.

IIB

In one currently preferred embodiment, the compound is represented by the structure of formula IIB, wherein X is a bond. In another currently preferred embodiment, the compound is represented by the structure of formula IIB, wherein X is O. In another currently preferred embodiment, the compound is represented by the structure of formula IIB, wherein X is $CH_2$.

Specific examples of the compound of formula IIB include, but are not limited to:

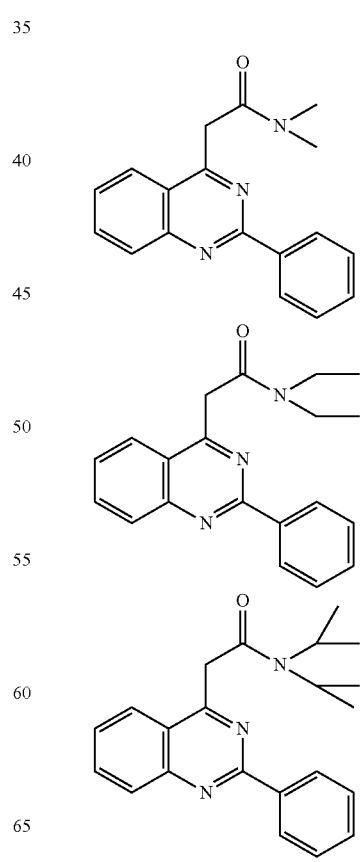

-continued

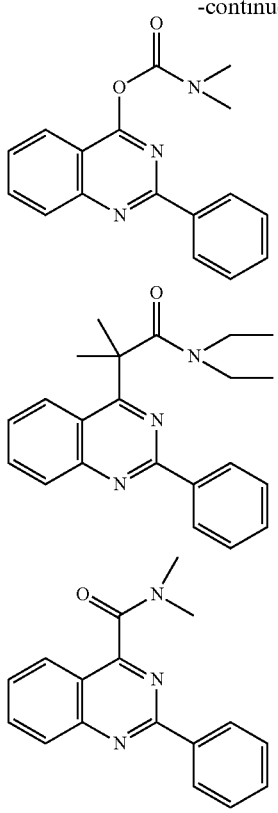

and

A particularly preferred compound is represented by the structure of compound 12b, as defined herein.

In another embodiment, the present invention provides a compound represented by the structure of formula III:

III

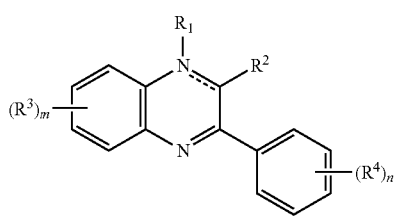

wherein
R$^1$ is absent, R$^2$ is a group of the formula A and ═ is a double bond; or
R$^1$ is a group of the formula A, R$^2$ oxo and ═ is a single bond;

A

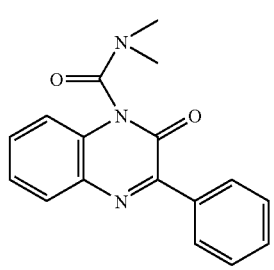

R$^3$ and R$^4$ are each independently selected from the group consisting of a linear or branched C$_1$-C$_6$ alkyl, a linear or branched C$_2$-C$_6$ alkenyl, a C$_3$-C$_8$ cycloalkyl, heterocyclyl, aryl, heteroaryl, halo, hydroxy, alkoxy, aryloxy, amino, cyano and nitro;

R$^5$ and R$^6$ are each independently selected from the group consisting of hydrogen, a linear or branched C$_1$-C$_6$ alkyl, a linear or branched C$_2$-C$_6$ alkenyl, a C$_3$-C$_8$ cycloalkyl, heterocyclyl, aryl and heteroaryl;
X is selected from the group consisting of a bond, —O—, —S—, —NR$^7$ and —CR$^8$R$^9$, wherein R$^7$, R$^8$ and R$^9$ are independently selected from the group consisting of hydrogen and a linear or branched C$_1$-C$_6$ alkyl;
m is 0, 1, 2, 3 or 4; and
n is 0, 1, 2, 3, 4 or 5;
including salts, hydrates, solvates, polymorphs, optical isomers, geometrical isomers, enantiomers, diastereomers, and mixtures thereof.

In one currently preferred embodiment, the compound is represented by the structure of formula III, wherein R$^5$ and R$^6$ are each independently selected from the group consisting of methyl, ethyl, propyl, isopropyl, n-butyl, sec-butyl, isobutyl and tert-butyl. In another currently preferred embodiment, the compound is represented by the structure of formula III, wherein m and n are each 0. In one currently preferred embodiment, the compound is represented by the structure of formula III, wherein X is a bond. In another currently preferred embodiment, the compound is represented by the structure of formula III, wherein X is O. In another currently preferred embodiment, the compound is represented by the structure of formula III, wherein X is CH$_2$.

One embodiment of the compound of formula III is represented by the structure of formula IIIA.

IIIA

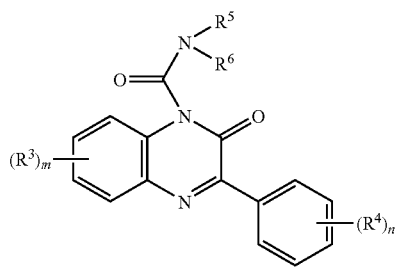

Specific examples of the compound of formula IIIA include, but are not limited to:

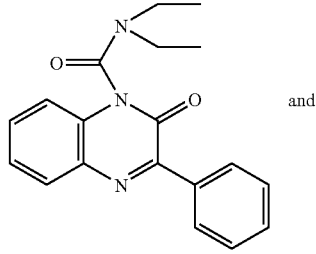

and

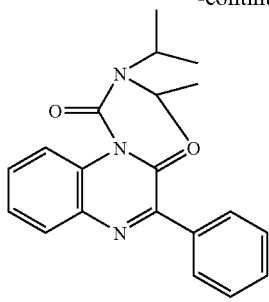

Another embodiment of the compound of formula III is represented by the structure of formula IIIB.

IIIB

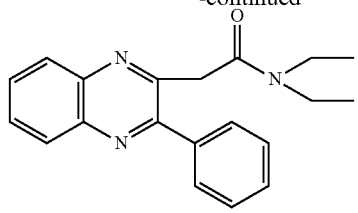

In one currently preferred embodiment, the compound is represented by the structure of formula IIIB, wherein X is a bond. In another currently preferred embodiment, the compound is represented by the structure of formula IIIB, wherein X is O. In another currently preferred embodiment, the compound is represented by the structure of formula IIIB, wherein X is $CH_2$.

Specific examples of the compound of formula IIB include, but are not limited to:

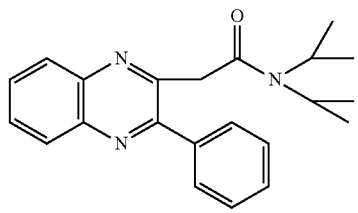

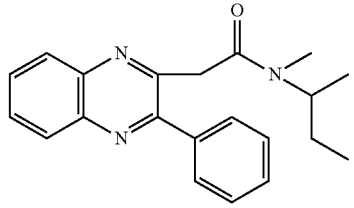

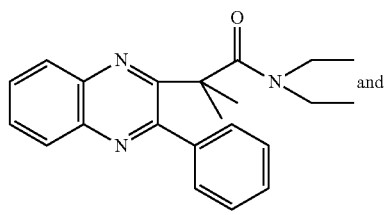

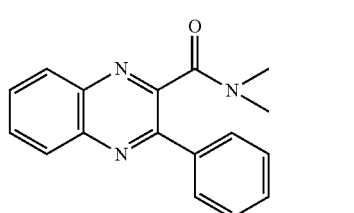

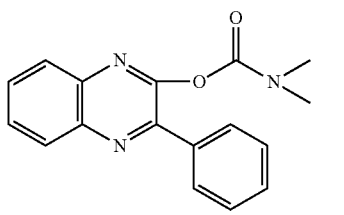

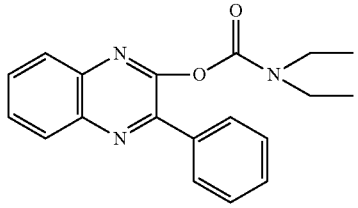

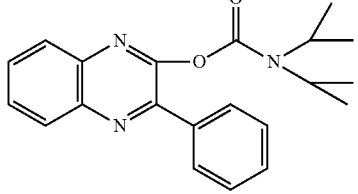

and

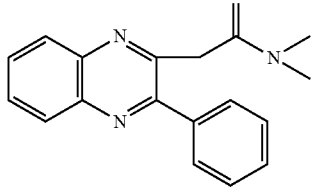

Multimeric Compounds

Polyvalency is a very common phenomenon in biochemical systems. Many important interactions in biology involve simultaneous interactions of multiple ligands and multiple receptors (polyvalency) (Mammen M.; Choi S. K.; Whitesides G. M., *Angew. Chem., Int. Ed.* 1998, 37, 2755). Polyvalent interactions are different from monovalent interactions; in particular, they can be collectively much stronger than corresponding monovalent interactions. A comparison of the binding of a monomeric ligand to a monomeric receptor with the binding of a dimeric ligand to a dimeric receptor establishes that in the later case, the system is energetically more favourable. Indeed, entropy is earned in the binding process. The same concept is applicable to the binding of polyvalent ligands to receptors with many binding sites. Indeed, polyvalent presentation of a ligand, which is itself weakly bound as a monomer, can often lead to very strong biological effects. In this context, polyvalency can often amplify weak biological interactions.

Thus, in another aspect, the present invention contemplates dimeric, oligomeric or polymeric derivatives comprising a plurality of covalently linked PBR ligands. Without wishing to be bound by any particular mechanism or theory, it is believed that the presence of more than one PBR binding moiety in the same molecule may increase the local concentration of the active moiety at the target site, thereby increasing potency of the compound.

Thus, in one embodiment, the present invention provides polyvalent compounds comprising two or more PBR binding molecules (PBR ligands), represented by the structure of formula IV:

(A)$_p$-Y    IV wherein A is independently of the other a moiety which binds to the PBR, p is an integer of 2-6 and Y is a linker. The number of PBR ligand units in formula IV (represented by the integer p) depends on the valency of the linker, and is generally selected from the group consisting of 2, 3, 4, 5 and 6.

The PBR ligand can be a classical ligand such as PK 11195, Ro5 4864, pyrrolobenzoxazepine, FGIN 1-27, 3 Alpidem, SSR 180575, or any other known PBR ligand. Alternatively, the PBR ligand can be any one or more of the compounds of the present invention, i.e., a compound of formula I, II or III, or any combination thereof.

The linker can be, for example, unsubstituted or substituted $C_1$-$C_{12}$ alkylene, polyoxy $C_1$-$C_{12}$ alkylene, polyamino $C_1$-$C_{12}$ alkylene, polythio $C_1$-$C_{12}$ alkylene, polyamide, polyester, a sugar moiety, —NH—, —S—, —OR$^{10}$—, —NHR$^{11}$— and —SR$^{12}$—, wherein R$^{10}$, R$^{11}$ and R$^{12}$ are each independently unsubstituted or substituted $C_1$-$C_{12}$ alkylene Currently preferred compounds are symmetric or asymmetric derivatives of the quinazoline, quinoxaline and phthalazine derivatives of the present invention, and/or of known PBR ligands such as PK 11195, Ro5 4864, pyrrolobenzoxazepine, FGIN 1-27, 3 Alpidem and SSR 180575. Representative and non limiting examples include:

A. Phthalazines
A compound of any of formula V, VA and VB

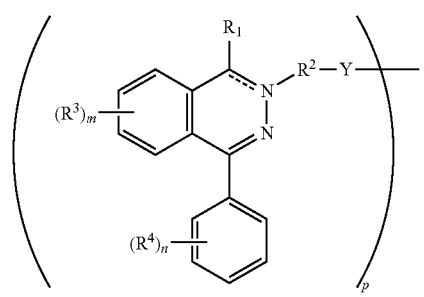

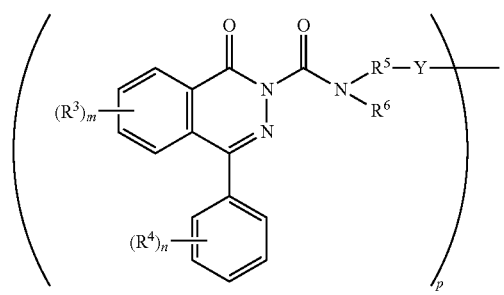

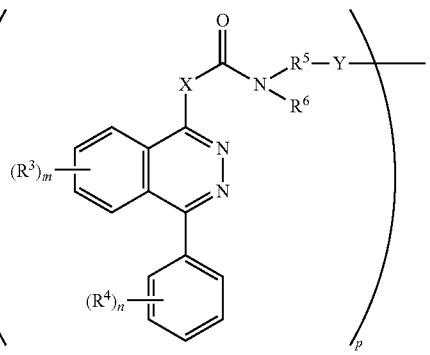

wherein

R$^1$ is oxo, R$^2$ is a group of the formula A and ═ is a single bond; or

R$^1$ is a group of the formula A, R$^2$ is absent and ═ is a double bond

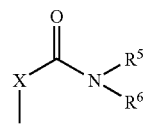

R$^3$ and R$^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

R$^5$ is selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;

R$^6$ is selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, —NR$^7$ and —CR$^8$R$^9$, wherein R$^7$, R$^8$ and R$^9$ are independently selected from the group consisting of hydrogen and a linear or branched $C_1$-$C_6$ alkyl;

Y is a linker moiety;

m is 0, 1, 2, 3 or 4;

n is 0, 1, 2, 3, 4 or 5; and p is 2, 3, 4, 5 or 6;

including salts, hydrates, solvates, polymorphs, optical isomers, geometrical isomers, enantiomers, diastereomers, and mixtures thereof.

B. Quinazolines
A compound of any of formula VI, VIA and VIB

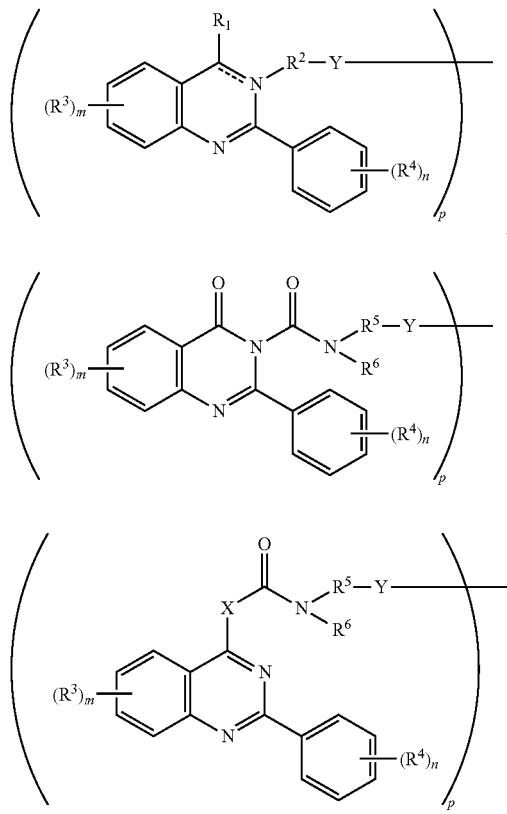

wherein
R¹ is oxo, R² is a group of the formula A and ══ is a single bond; or
R¹ is a group of the formula A, R² is absent and ══ is a double bond

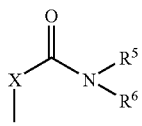

R³ and R⁴ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

R⁵ is selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;

R⁶ is selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, —NR⁷ and —CR⁸R⁹, wherein R⁷, R⁸ and R⁹ are independently selected from the group consisting of hydrogen and a linear or branched $C_1$-$C_6$ alkyl;

Y is a linker moiety;
m is 0, 1, 2, 3 or 4;
n is 0, 1, 2, 3, 4 or 5; and
p is 2, 3, 4, 5 or 6;
including salts, hydrates, solvates, polymorphs, optical isomers, geometrical isomers, enantiomers, diastereomers, and mixtures thereof.

C. Quinoxalines
A compound of any of formula VII, VIIA and VIIB

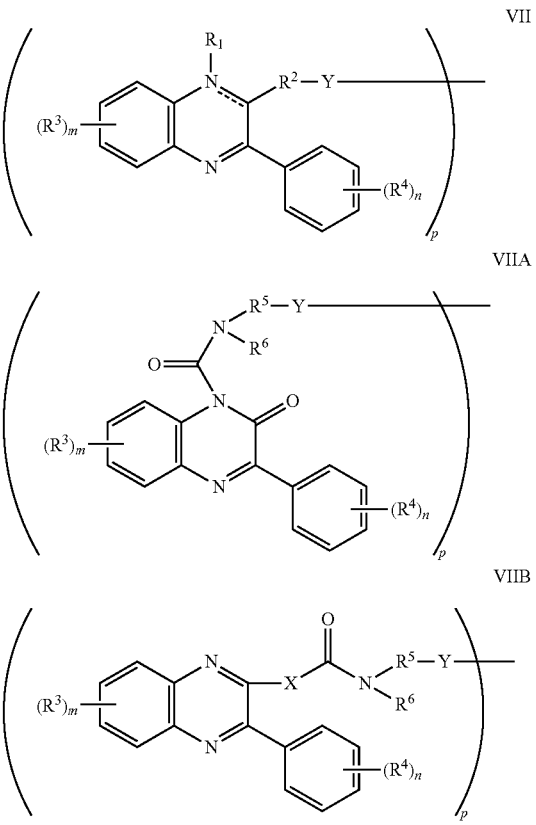

wherein
R¹ is absent, R² is a group of the formula A and ══ is a double bond; or
R¹ is a group of the formula A, R² oxo and ══ is a single bond;

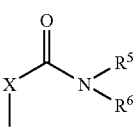

R³ and R⁴ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

R⁵ is selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;

$R^6$ is selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, —$NR^7$ and —$CR^8R^9$, wherein $R^7$, $R^8$ and $R^9$ are independently selected from the group consisting of hydrogen and a linear or branched $C_1$-$C_6$ alkyl;

Y is a linker moiety;

m is 0, 1, 2, 3 or 4;

n is 0, 1, 2, 3, 4 or 5; and p is 2, 3, 4, 5 or 6;

including salts, hydrates, solvates, polymorphs, optical isomers, geometrical isomers, enantiomers, diastereomers, and mixtures thereof.

It is apparent to a person of skill in the art that the multimeric compounds of the present invention should not be limited to the symmetric compounds described above. Asymmetric compounds including any combination of PBR ligands are also encompassed by the broad scope of the invention. For example, the multimeric compound can include any combination of phthalazine, quinazoline and quinoxaline moiety, as well as moieties of known PBR ligands. Illustrative examples include, but are not limited to: a heteromultimer comprising at least one phthalazine of formula I and at least one quinazoline of formula II; a heteromultimer comprising at least one phthalazine of formula I and at least one quinoxaline of formula III; a heteromultimer comprising at least one quinazoline of formula II and at least one quinoxaline of formula III; a heteromultimer comprising at least one phthalazine of formula I and at least one classical PBR ligand, e.g., PK 11195, Ro5 4864, pyrrolobenzoxazepine, FGIN 1-27, 3 Alpidem, SSR 180575, or any other known PBR ligand; a heteromultimer comprising at least one quinazoline of formula II and at least one classical PBR ligand, e.g., PK 11195, Ro5 4864, pyrrolobenzoxazepine, FGIN 1-27, 3 Alpidem, SSR 180575, or any other known PBR ligand; and a heteromultimer comprising at least one quinoxaline of formula III and at least one classical PBR ligand, e.g., PK 11195, Ro5 4864, pyrrolobenzoxazepine, FGIN 1-27, 3 Alpidem, SSR 180575, or any other known PBR ligand. A person of skill in the art is capable of designing the appropriate combination of ligands, as desired.

Dimeric Compounds

In one currently preferred embodiment, the present invention provides dimeric compounds comprising two PBR binding molecules (PBR ligands) separated by a linker, wherein the dimer is represented by the structure of formula VIII:

A-Y—B  VIII wherein A and B are independently of each other a moiety which binds to the PBR (PBR ligand) and Y is a linker, wherein the PBR ligand and linkers are as described above for the compounds of formula IV, V, VI and VII.

A currently preferred dimer is a dimer of PK 11195, designated compound 24:

24

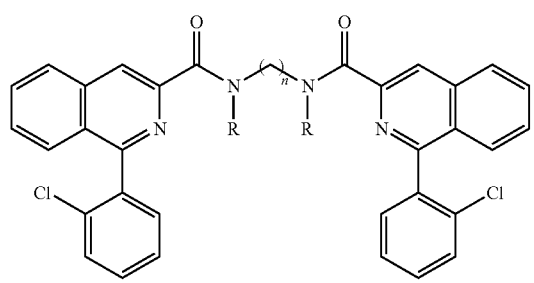

wherein n is an integer of from 1 to 12 and each R is independently selected from the group consisting of a hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl.

Specific embodiments of the compound of formula 24 included, but are not limited to: n is 2 and R is H (24a); n is 4 and R is H (24b); n is 2 and R is methyl (24c); n is 3 and R is methyl (24d); and n is 6 and R is methyl (24e). Currently preferred compounds are 24d and 24e.

Other currently preferred compounds are symmetric or asymmetric dimers of the quinazoline, quinoxaline and phthalazine derivatives of the present invention, and/or of known PBR ligands such as PK 11195, Ro5 4864, pyrrolobenzoxazepine, FGIN 1-27, 3 Alpidem and SSR 180575. Representative and non limiting examples include:

D. Phthalazines

A compound of any of formula IX, IXA and IXB:

IX

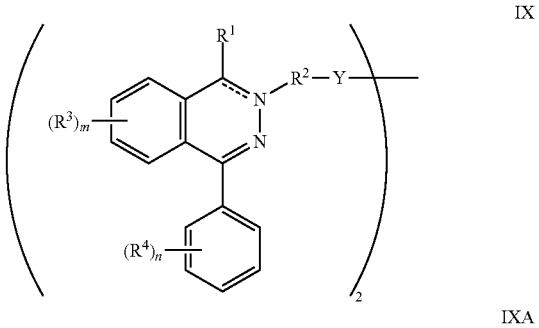

IXA

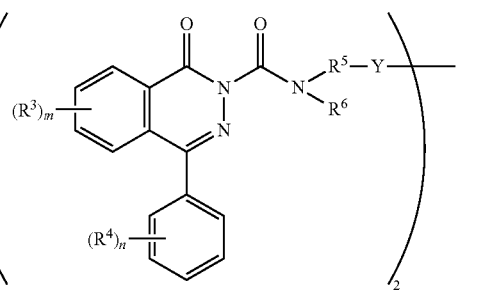

IXB

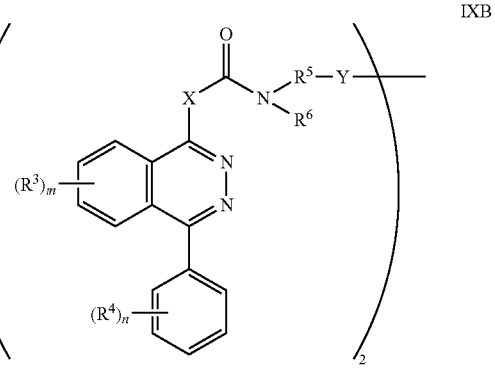

wherein $R^1$ is oxo, $R^2$ is a group of the formula A and ═ is a single bond; or $R^1$ is a group of the formula A, $R^2$ is absent and ═ is a double bond

A

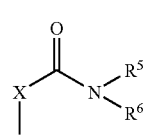

$R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

$R^5$ is independently selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;

$R^6$ is independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, —$NR^7$ and —$CR^8R^9$, wherein $R^7$, $R^8$ and $R^9$ are independently selected from the group consisting of hydrogen and a linear or branched $C_1$-$C_6$ alkyl;

Y is a linker moiety;

m is 0, 1, 2, 3 or 4; and n is 0, 1, 2, 3, 4 or 5;

including salts, hydrates, solvates, polymorphs, optical isomers, geometrical isomers, enantiomers, diastereomers, and mixtures thereof.

E. Quinazolines

A compound of any of formula X, XA and XB:

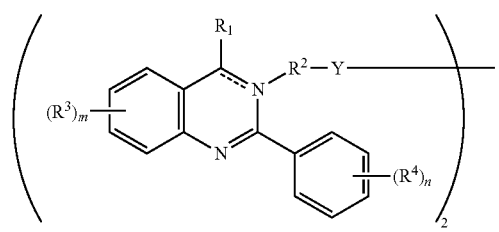

X

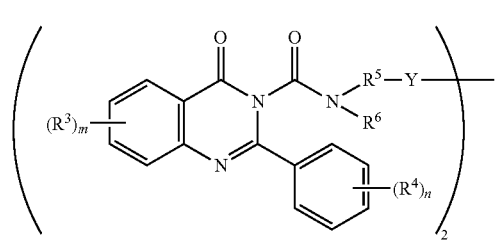

XA

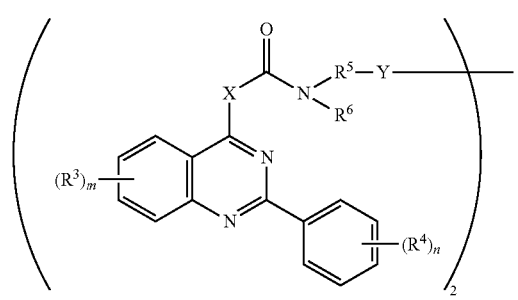

XB wherein
$R^1$ is oxo, $R^2$ is a group of the formula A and ═ is a single bond; or
$R^1$ is a group of the formula A, $R^2$ is absent and ═ is a double bond

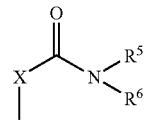

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

$R^5$ is independently selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;

$R^6$ is independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, —$NR^7$ and —$CR^8R^9$, wherein $R^7$, $R^8$ and $R^9$ are independently selected from the group consisting of hydrogen and a linear or branched $C_1$-$C_6$ alkyl;

Y is a linker moiety;

m is 0, 1, 2, 3 or 4; and n is 0, 1, 2, 3, 4 or 5;

including salts, hydrates, solvates, polymorphs, optical isomers, geometrical isomers, enantiomers, diastereomers, and mixtures thereof.

F. Quinoxalines

A compound of any of formula XI, XIA and XIB:

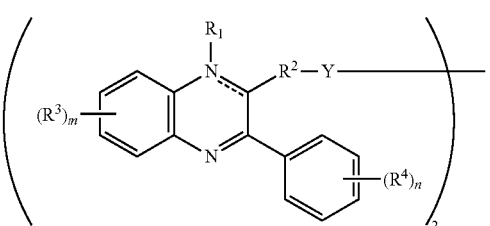

XI

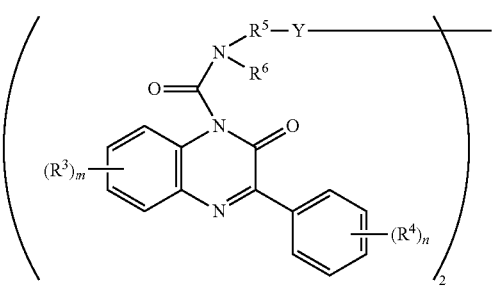

XIA

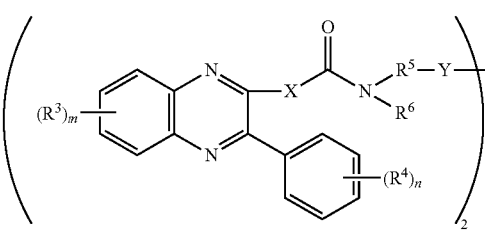

XIB wherein
$R^1$ is absent, $R^2$ is a group of the formula A and ═ is a double bond; or
$R^1$ is a group of the formula A, $R^2$ oxo and ═ is a single bond;

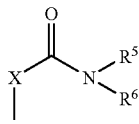

A $R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;

$R^5$ is independently selected from the group consisting of a linear or branched $C_1$-$C_6$ alkylene, a linear or branched $C_2$-$C_6$ alkenylene, a $C_3$-$C_8$ cycloalkylene, heterocyclylene, arylene and heteroarylene;

$R^6$ is independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;

X is selected from the group consisting of a bond, —O—, —S—, —NR$^7$ and —CR$^8$R$^9$, wherein R$^7$, R$^8$ and R$^9$ are independently selected from the group consisting of hydrogen and a linear or branched $C_1$-$C_6$ alkyl;

Y is a linker moiety;

m is 0, 1, 2, 3 or 4; and n is 1, 2, 3, 4 or 5;

including salts, hydrates, solvates, polymorphs, optical isomers, geometrical isomers, enantiomers, diastereomers, and mixtures thereof.

It is apparent to a person of skill in the art that the dimeric compounds of the present invention should not be limited to the symmetric compounds described above. Asymmetric compounds (heterodimers) including any combination of PBR ligands are also encompassed by the broad scope of the invention. For example, the dimeric compound can include any combination of phthalazine, quinazoline and quinoxaline moiety, as well as moieties of known PBR ligands. Illustrative examples include, but are not limited to: a heterodimer of a phthalazine of formula I and a quinazoline of formula II; a heterodimer of a phthalazine of formula I and a quinoxaline of formula III; a heterodimer of a quinazoline of formula II and a quinoxaline of formula III; a heterodimer of a phthalazine of formula I and a classical PBR ligand, e.g., PK 11195, Ro5 4864, pyrrolobenzoxazepine, FGIN 1-27, 3 Alpidem, SSR 180575, or any other known PBR ligand; a heterodimer of a quinazoline of formula II and a classical PBR ligand, e.g., PK 11195, Ro5 4864, pyrrolobenzoxazepine, FGIN 1-27, 3 Alpidem, SSR 180575, or any other known PBR ligand; and a heterodimer of a quinoxaline of formula III and a classical PBR ligand, e.g., PK 11195, Ro5 4864, pyrrolobenzoxazepine, FGIN 1-27, 3 Alpidem, SSR 180575, or any other known PBR ligand. A person of skill in the art is capable of designing the appropriate combination of ligands, as desired.

Chemical Definitions

The term "$C_1$ to $C_6$ alkyl" used herein alone or as part of another group denotes linear and branched, saturated alkyl groups. Preferred are alkyl groups containing from 1 to 4 carbon atoms ($C_1$ to $C_4$ alkyls). Examples of saturated alkyl groups include, but are not limited to, methyl, ethyl, n-propyl, isopropyl, n-butyl, iso-butyl, sec-butyl, tert-butyl, amyl, tert-amyl, hexyl, and the like. Similarly, the term "$C_1$ to $C_6$ alkylene" denotes a bivalent radicals of 1 to 6 carbons, where the alkyl radical is bonded at two positions connecting together two separate additional groups (e.g., CH$_2$).

The $C_1$ to $C_6$ allyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$ to $C_{10}$ alkylthio arylthio, or $C_1$ to $C_{10}$ alkylsulfonyl groups. Any substituent can be unsubstituted or further substituted with any one of these aforementioned substituents.

The term "$C_2$ to $C_6$ alkenyl" used herein alone or as part of another group denotes linear and branched, mono or polyunsaturated alkenyl groups containing at least one carbon-carbon double bond. Examples of alkenyl groups include, but are not limited to, vinyl, allyl, butenyl and the like. Similarly, the term "$C_2$ to $C_6$ alkenylene" denotes a bivalent radicals of 2 to 6 carbons where the alkenyl radical is bonded at two positions connecting together two separate additional groups (e.g., —CH═CH—). The $C_2$ to $C_6$ alkenyl can be unsubstituted or it can be substituted by any one or more of the substituents defined above for alkyl.

The term "$C_3$ to $C_8$ cycloalkyl" used herein alone or as part of another group denotes any unsaturated or unsaturated (e.g., cycloalkenyl) monocyclic or polycyclic group. Nonlimiting examples of cycloalkyl groups are cyclopropyl, cyclobutyl, cyclopentyl, cyclohexyl or cycloheptyl. Examples or cycloalkenyl groups include, but are not limited to, cyclopentenyl, cyclohexenyl and the like. Similarly, the term "cycloalkylene" means a bivalent cycloalkyl, as defined above, where the cycloalkyl radical is bonded at two positions connecting together two separate additional groups. The cycloalkyl group can be unsubstituted or substituted with any one or more of the substituents defined above for alkyl.

The term "aryl" used herein alone or as part of another group denotes an aromatic ring system containing from 6-14 ring carbon atoms. Similarly, the term "arylene" means a bivalent cycloalkyl, as defined above, where the aryl radical is bonded at two positions connecting together two separate additional groups. The aryl ring can be a monocyclic, bicyclic, tricyclic and the like. Non-limiting examples of aryl groups are phenyl, naphthyl including 1-naphthyl and 2-naphthyl, and the like. The aryl group can be unsubtituted or substituted through available carbon atoms with one or more groups defined hereinabove for alkyl.

The term "heteroaryl" used herein alone or as part of another group denotes a heteroaromatic system containing at least one heteroatom ring atom selected from nitrogen, sulfur and oxygen. Similarly, the term "heteroarylene" means a bivalent cycloalkyl, as defined above, where the heteroaryl radical is bonded at two positions connecting together two separate additional groups. The heteroaryl contains 5 or more ring atoms. The heteroaryl group can be monocyclic, bicyclic, tricyclic and the like. Also included in this expression are the benzoheterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can optionally be substituted through available atoms with one or more groups defined hereinabove for alkyl. The heteroaryl group can be unsubtituted or substituted through available atoms with one or more groups defined hereinabove for alkyl.

The term "heterocyclic ring" or "heterocyclyl" used herein alone or as part of another group denotes a five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings can be saturated, fully unsaturated or partially unsaturated, with fully saturated rings being preferred. Preferred heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The term "halogen" or "halo" as used herein alone or as part of another group refers to chlorine, bromine, fluorine, and iodine.

The term "amino" as used herein alone or as part of another group refers to an $NH_2$ group. The terms "alkyl amino, dialkylamino, arylamino, diaryl amino, heteroarylamino, diheteroarylamino" and variants thereof as used herein refer to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl and the like.

The term "hydroxy" refers to an OH group. The term "oxo" refers to an oxygen doubly bonded to the adjacent atom (=O). When the adjacent atom is a carbon, the carbon and the oxo together define a carbonyl group (C=O). The terms "alkoxy", "aryloxy" "arylalkyloxy" or "heteroaryloxy" as used herein alone or as part of another group includes any of the above alkyl, aryl or heteroaryl groups linked to an oxygen atom. Nonlimiting examples of an alkoxy group is methoxy, ethoxy, n-propoxy, isopropoxy, n-butoxy, t-butoxy and like groups. An example of an aryloxy group is phenyloxy. The alkoxy, aryloxy, arylalkyloxy or heteroaryloxy groups can be unsubstituted or substituted with any one or more of the substituents defined above for alkyl.

The term "cyano" as used herein alone or as part of another group refers to a CN group. The term "nitro" as used herein alone or as part of another group refers to an $NO_2$ group.

All stereoisomers of the compounds of the instant invention are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. In addition, several of the compounds of the invention contain one or more double bonds. The present invention intends to encompass all structural and geometrical isomers including cis, trans, E and Z isomers, independently at each occurrence.

One or more of the compounds of the invention, may be present as a salt. The term "salt" encompasses both basic and acid addition salts, including but not limited to carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., J. Pharm. Sci., 66:1-19 (1977), which is incorporated herein by reference. Furthermore, any zwitterionic form of the instant compounds is also contemplated.

The present invention also includes solvates of compounds I and II and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of compounds II and II and salts thereof. The term "polymorph" refers to a particular crystalline state of a substance, which can be characterized by particular physical properties such as X-ray diffraction, IR spectra, melting point, and the like.

Therapeutic Use

The compounds of the invention bind to peripheral-type benzodiazepine receptor (PBR), reduce basal apoptotic levels in neuronal cells, as well as reduce apoptosis induced by glutamate, which is known to be an important agent causing secondary brain damage after traumatic brain damages, and also takes part in neurodegenerative diseases. As such, the compounds of the invention are useful in the treatment and prevention of brain damage resulting from brain injury, especially secondary brain injury due to traumatic brain injury associated with, e.g., warfare, automobile accidents, sports injuries, violent crimes, household accidents, child abuse, gun shot wounds, etc. The compounds of the invention are also useful in treating and preventing neurodegenerative diseases such as Alzheimer Disease, Parkinson's Disease, Huntington's disease, and others.

In a preferred embodiment, the compounds of the invention bind more selectively to PBR than current PBR ligands do and prevent brain cell death, including apoptosis, as it occurs due to TBI. In another preferred embodiment, the novel compounds easily cross the blood brain barrier, an advantageous property for the prevention of brain cell death.

Thus, in one aspect, the present invention provides a method for treating or preventing brain damage resulting from brain injury, comprising the step of administering to a subject in need thereof an effective amount of a compound of formula I-XI, as described herein. Preferably, the compound is one or more of the compounds represented by the structure IA, IB, IIA, IIB, IIIA, IIIB, VA, VB, VIA, VIB, VIIA, VIIB, IXA, IXB, XA, XB, XIA and XIB. In some embodiments, the compound is administered in a pharmaceutical composition. Preferably, the compound is represented by the structure of formula 19b, compound 12b, or compound 24d.

In one embodiment, the brain injury is traumatic brain injury (TBI). As contemplated herein, the compounds of the invention are particularly useful for preventing and treating secondary brain damage resulting from TBI. Thus, the compounds of the invention are useful, e.g., for treating soldiers in the battlefield, especially soldiers who have suffered TBI. For example, secondary brain damage due to TBI can be treated or prevented by administering the compounds of the invention to soldiers, or by supplying paramedics in the battlefield or at the site of terrorist attack with the compounds of the invention, so that the compounds can be administered on site as soon as possible after the soldier has suffered TBI. The compounds of the invention are also useful for civilians who are victims of violent crimes, including but not limited to, terrorist attacks. This may reduce the incidence of disability presently occurring in the aftermath of TBI suffered due to hostilities, including terrorist attacks.

The utility of the compounds of the invention is not limited to violent crimes such as warfare and terrorist attacks. The compounds of the invention are also useful for individuals suffering from brain injury due to domestic occurrences, such as automobile accidents, sports injuries, household accidents, child abuse, gun shot wounds, etc, including their consequences such events such as disability and epilepsy.

The present invention also relates to the use of a compound of Formula I-XI in the manufacture of a medicament for treating or preventing brain damage resulting from brain injury: In a currently preferred embodiment, the present invention relates to the use compound 19b in the manufacture of a medicament for treating or preventing brain damage resulting from brain injury. In another currently preferred embodiment, the present invention relates to the use compound 12b in the manufacture of a medicament for treating or preventing brain damage resulting from brain injury. In another currently preferred embodiment, the present invention relates to the use of compound 24d in the manufacture of a medicament for treating or preventing brain damage resulting from brain injury.

The present invention also relates to the use of a compound of Formula I-XI in the manufacture of a medicament to for treating or preventing neurodegenerative diseases. In a currently preferred embodiment, the present invention relates to the use of compound 19b in the manufacture of a medicament to for treating or preventing neurodegenerative diseases. In another currently preferred embodiment, the present invention relates to the use of compound 12b in the manufacture of a medicament to for treating or preventing neurodegenerative diseases. In another currently preferred embodiment, the present invention relates to the use of compound 24d in the manufacture of a medicament to for treating or preventing neurodegenerative diseases.

As mentioned above, the compounds of the invention reduce basal apoptotic levels in neuronal cells, as well as reduce apoptosis induced by glutamate, which is known to be an important agent in neurodegenerative pathways. As such, the compounds of the invention are also useful in treating and preventing neurodegenerative diseases.

Generally, diseases of the central nervous system, are referred to as neurodegenerative, indicating that they are characterized by gradually evolving, relentlessly progressive neuronal death occurring for reasons that are still largely unknown. The identification of these diseases depends upon exclusion of such possible causative factors as infections, metabolic derangements, and intoxications. A considerable proportion of the disorders classed as neurogenerative are genetic, with either dominant or recessive inheritance. Others, however, occur only sporadically as isolated instances in a given family. Classification of the degenerative diseases cannot be based upon any exact knowledge of cause or pathogenesis; their subdivision into individual syndromes rests on descriptive criteria based largely upon neuropathologic and clinical aspects. This group of diseases presents as several distinct clinical syndromes, the recognition of which can assist the clinician in arriving at a diagnosis. Examples of "neurodegenerative diseases" in the context of the present invention include, but are not limited to, Alzheimer Disease, Pick's disease, diffuse Lewy body disease, progressive supranuclear palsy (Steel-Richardson syndrome), multisystem degeneration (Shy-Drager syndrome), motor neuron diseases, amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases, Creutzfeldt-Jakob, Gerstmann-Straussler-Scheinker disease, Kuru and fatal familial insomnia.

As used herein, the term "administering" refers to bringing in contact with a compound of the present invention. Administration can be accomplished to cells or tissue cultures, or to living organisms, for example humans. In one embodiment, the present invention encompasses administering the compounds of the present invention to a human subject.

A "therapeutic" or "effective" treatment is a treatment administered to a subject who exhibits signs of pathology for the purpose of diminishing or eliminating those signs. A "therapeutically effective amount" or an "effective amount" of a compound of the invention is that amount of compound which is sufficient to provide a beneficial effect to the subject to which the compound is administered.

Pharmaceutical Compositions

Although the compounds of the present invention can be administered alone, it is contemplated that these compounds will be administered in a pharmaceutical composition containing the compound of the invention together with a pharmaceutically acceptable carrier or excipient.

The pharmaceutical compositions of the present invention can be formulated for administration by a variety of routes including oral, rectal, transdermal, parenteral (subcutaneous, intraperitoneal, intravenous, intraarterial, transdermal and intramuscular), topical, intranasal, rectally via a suppository or via dialysis. Such compositions are prepared in a manner well known in the pharmaceutical art and comprise as an active ingredient at least one compound of the present invention as described hereinabove, and a pharmaceutically acceptable excipient or a carrier. The term "pharmaceutically acceptable" means approved by a regulatory agency of the Federal or a state government or listed in the U. S. Pharmacopeia or other generally recognized pharmacopeia for use in animals and, more particularly, in humans.

During the preparation of the pharmaceutical compositions according to the present invention the active ingredient is usually mixed with a carrier or excipient, which may be a solid, semi-solid, or liquid material. The compositions can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The carriers may be any of those conventionally used and are limited only by chemical-physical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. Other pharmaceutical carriers can be sterile liquids, such as water, alcohols (e.g., ethanol) and lipid carriers such as oils, (including those of petroleum, animal, vegetable or synthetic origin, such as peanut oil, soybean oil, mineral oil, sesame oil and the like), phospholipids (e.g. lecithin), polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions.

The formulations can additionally include lubricating agents such as talc, magnesium stearate, and mineral oil; wetting agents, anti-oxidants, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride. Fatty acids can also be included.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

Any method can be used to prepare the pharmaceutical compositions. Solid dosage forms can be prepared by wet granulation, dry granulation, direct compression and the like.

The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention may be incorporated, for administration orally or by injection, include aqueous solutions, alcoholic solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices that deliver the formulation in an appropriate manner.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. The present invention may be used topically or transdermally to treat cancer, for example, melanoma. Adjuvants for topical or gel base forms may include, for example, sodium carboxymethylcellulose, polyacrylates, polyoxyethylene-polyoxypropylene-block polymers, polyethylene glycol and wood wax alcohols.

Alternative formulations include nasal sprays, liposomal formulations, slow-release formulations, controlled-release formulations and the like, as are known in the art.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

It may be desirable to administer the pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. According to some preferred embodiments, administration can be by direct injection e.g., via a syringe, at the site of a tumor or neoplastic or pre-neoplastic tissue.

The compounds may also be administered by any convenient route, for example by infusion or bolus injection, by absorption through epithelial linings (e.g., oral mucosa, rectal and intestinal mucosa, etc.), and may be administered together with other therapeutically active agents. It is preferred that administration is localized, but it may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

A compound of the present invention can be delivered in an immediate release or in a controlled release system. In one embodiment, an infusion pump may be used to administer a compound of the invention, such as one that is used for delivering chemotherapy to specific organs or tumors (see Buchwald et al., 1980, Surgery 88: 507; Saudek et al., 1989, N. Engl. J. Med. 321: 574). In a preferred form, a compound of the invention is administered in combination with a biodegradable, biocompatible polymeric implant, which releases the compound over a controlled period of time at a selected site. Examples of preferred polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

Furthermore, at times, the pharmaceutical compositions may be formulated for parenteral administration (subcutaneous, intravenous, intraarterial, transdermal, intraperitoneal or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

The amount of a compound of the invention that will be effective in the treatment of a particular disorder or condition, including cancer, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. A preferred dosage will be within the range of 0.01-1000 mg/kg of body weight, more preferably, 0.1mg/kg to 100 mg/kg and even more preferably 1 mg/kg to 10 mg/kg. Effective doses may be extrapolated from dose-response curves derived from in vitro or animal model test bioassays or systems.

All references cited in the present application are expressly incorporated by reference in their entirety, as if fully set forth herein.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXPERIMENTAL DETAILS SECTION

EXAMPLE 1

Materials And Methods

Cell culture of neural cell lines Various human glial cell lines (T98G, U87MG, A172, U118), as well as human neuronal cell lines SH-SY 5Y and Be(2)-C were used to test the new compounds. The applicants also have produced modified rat C6 glial cell lines under-expressing and over-expressing various components of the PBR complex, which allows to study PBR specific effects. Human glial and neuronal cell lines under- and over-expressing components of the PBR complex, can also be used, according to methods described previously [Levin E et al. *Biochemistry* 2005;44:9924-9935; Kuznetsov V et al. Abstract Viewer/Itinerary Planner. Washington, D.C.: Society for Neuroscience, Online: 2005; Program No. 673.4; Weisinger G et al. *Biochemistry* 2004;43: 12315-12321].

PBR binding and Western blot protein analysis PBR binding assays were utilized to determine whether the compounds of the invention, are able to compete with standard PBR ligands, according to methods described previously [Veenman L et al. *Biochemistry* 2005;44:9924-9935; Levin E et al. *Biochemistry* 2005;44:9924-9935]. Briefly, the assay utilizes radioactive standard ligand [$^3$H] PK 11195 (1-(2-chlorophenyl)-N-methyl-N-(1-methyl-propyl)-3-isoquinolinecarboxamide), and measures the ability of the compounds of the invention to compete with standard ligand in binding to PBR. Total radioactive binding was determined by measuring the radioactivity of the radioactive ligand-receptor complex, obtained in the reaction of radioactive standard with the PBR. Radioactive standard and the examined ligand were added to the PBR and after some incubation time the radioactivity of the resulting ligand-receptor complexes was measured with the help of γ-counter. This radioactivity indicates the binding of the radioactive standard to PBR. When the examined ligand binds better to PBR, consequently, less radioactive standard binds to PBR, therefore the measured radioactivity is lower. For an easier interpretation of our results, the binding was expressed in percentage of radioactive ligand binding. The lower the number, the better the binding of the examined ligand to PBR. Western blot analysis can be used to see which components of the PBR-complex may be important for the efficacy of the new PBR ligands, according to methods described previously [Levin E et al. 2005; Kuznetsov V et al. 2005; Weisinger G et al. *Biochemistiy* 2004].

Cell count. Cells counts using a microscope is a simple method to assay the effects of new drugs on cell number of cultured neural cell lines, according to methods described previously [Veenman L et al. 2005; Levin E et al. 2005].

Cell death, including apoptosis. The Cell Death Detection ELISA$^{PLUS}$ kit of Roche Molecular Biochemicals (Mannheim, Germany) was used to determine the effects on apoptosis by the new PBR ligands, in particular the one of the present description, according to methods described previously [Veenman L et al. 2005; Levin E et al. 2005]. Also, the Trypan blue method was applied in order to determine the cell viability after application of the new PBR ligands, according to methods described previously [Veenman L et al. 2005; Levin E et al. 2005]. Cell death including apoptosis of neural cells is induced by glutamate and Abeta, according to methods described previously [Michal Gaitner, M. Sc. thesis, 2004].

Flow cytometric analysis of the cells' life cycle. Cell cycle analysis using fluorescence assisted cell sorting (FACS) can be used to monitor the cell cycle profile of our cell cultures treated with our new PBR ligand, according to methods described previously [Veenman L et al. 2005; Levin E et al. 2005]. This provides additional information on the fractions of cells undergoing apoptosis, or other forms of cell death.

Mitochondrial membrane potential and mitochondrial volume measurement. To see whether the new PBR ligand is able to prevent opening of the mitochondrial permeability transition pore to prevent apoptosis changes in the mitochondrial volume and potential are measured, as described previously [Maaser K, *Br J Cancer* 2001;85:1771-1780].

Assays of cytochrome c, caspase 3, and caspase 9. Western blots are used to assay the essential components of the cascade leading from PBR ligand activity to apoptosis, according to methods described previously [Veenman L et al. 2005; Levin E et al. 2005].

Analysis of data. Results are expressed as means±SD. One-way or multiple analysis of variance, including post-hoc tests, as appropriate, are used to analyze the data. Bartlett's test for homogeneity of variance is used to determine the appropriate model i.e. parametric or non-parametric. Statistical significance are defined at $p<0.05$ [30].

EXAMPLE 2

Figure 8:
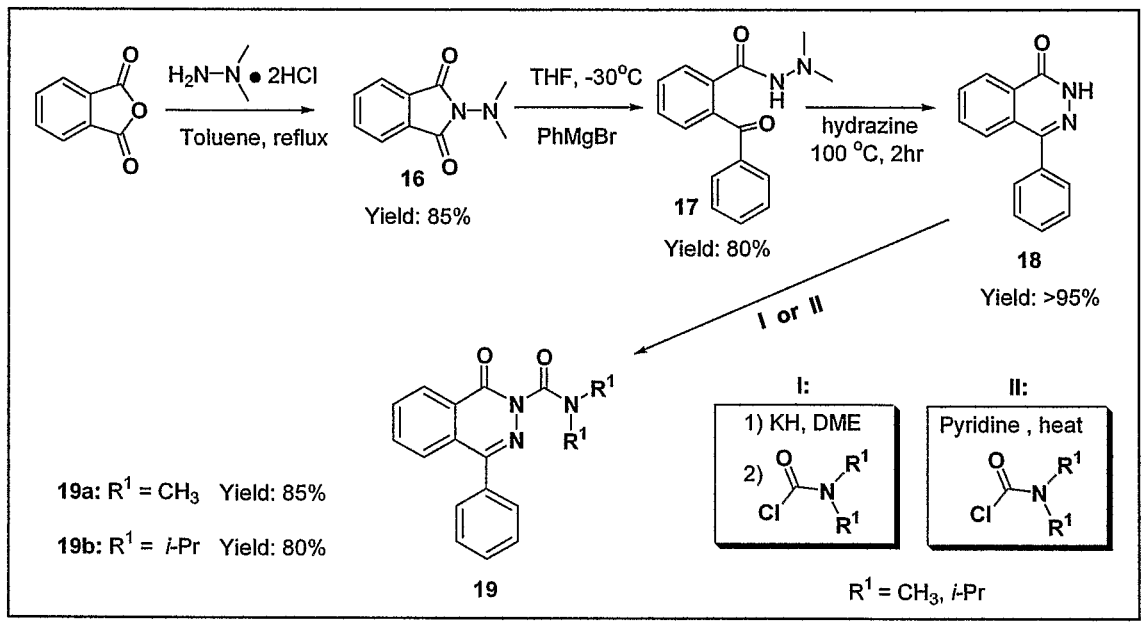
FIGS. 8-9: Synthesis of phthalazine derivatives.

Preparation of New Phthalazine, Quinazoline and Quinoxaline Derivatives a. Phthalazines:

Phthalazine derivatives of formula IA were prepared as described in FIG. 8 and as further detailed in Example 4. The commercially available phthalic anhydride was reacted with N,N-dimethyl hydrazine to give 2-(dimethylamino)isoindoline-1,3-dione 16 in good yield [Hanefeld W et al. *J Heterocyclic Chem.* 1996;33:1443]. Then, 16 was reacted with phenylmagnesium bromide, to lead to the intermediate 17 in good yield [Deniau E et al. *Tetrahedron: Asym.* 2003;14: 2253], which in turn was quantitatively converted by reaction with hydrazine to 4-phenylphthalazin-1(2H)-one 18 [Saito Y et al. *Synthesis* 2001;2:221]. Finally, the N-amidation product 19 (Compound I) was the major product obtained in good yield whatever the experimental conditions. Two different carbamoyl chlorides were used (R1=CH$_3$—compound 19a; and i-Pr—compound 19b) for the preparation of phthalazine derivatives. (FIG. 8).

Figure 9:
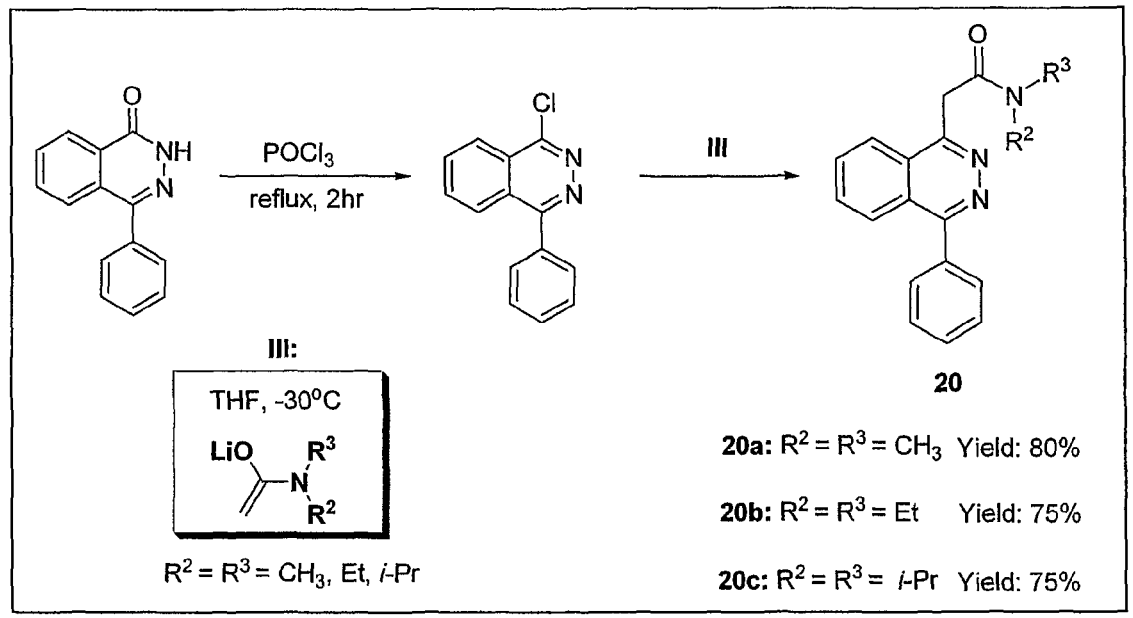

Phthalazine derivatives of formula IB were prepared by the synthetic route previously described (FIG. 9) and as further detailed in Example 4. Dimethyl 20a, diethyl 20b and diisopropyl-phenylphthalazine acetamide 20c were therefore synthesized, in good yields.

b. Quinazolines

Figure 10:
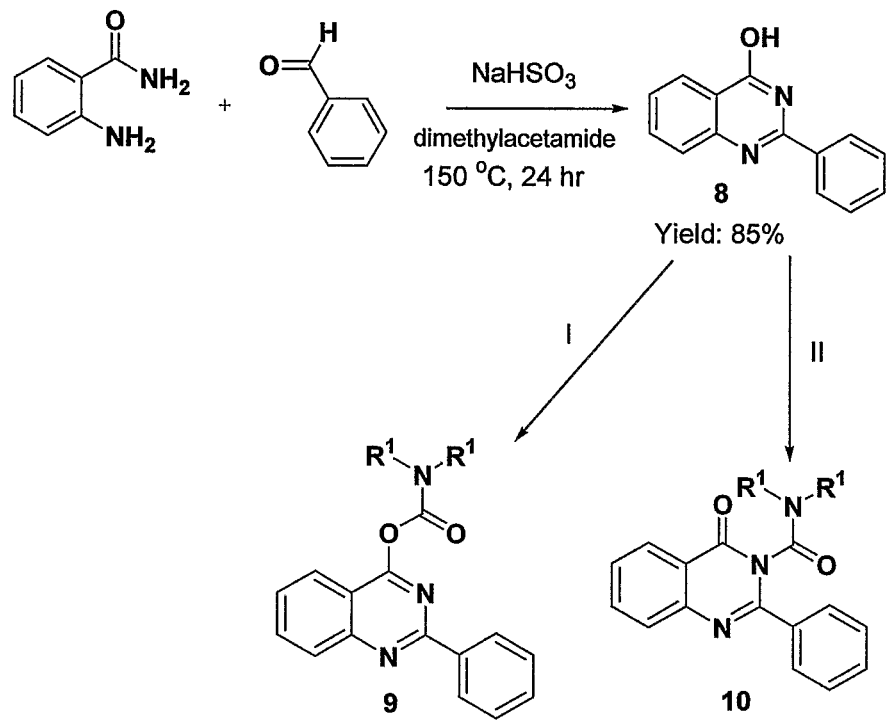
FIGS. 10-13: Synthesis of quinazoline derivatives.
Figure 10:
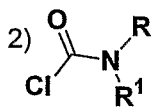
Figure 10:
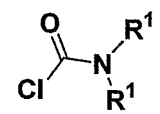

Quinazoline derivatives of formula IIA and IIB were prepared as described in FIG. 10 and as further detailed in Example 4. Commercially available anthranilamide reacts with benzaldehyde to give 2-phenylquinazolin-4-ol 8 in good yield. From 8, the potassium alcoholate is treated with carbamoyl chloride, the O-amidation product is obtained in moderate yield after purification. When 8 is heated in the presence of pyridine with the same carbamoyl chloride, the N-amidation product 10 was formed as the major product. Different alkyl groups on the nitrogen atom of carbamoyl chloride were tested. The structure of 10b has been determined by X-Ray analysis.

It should be noted that, following pathway I in FIG. 10 the opposite amidation product was also formed (i.e. the O-amidation 9a was isolated in 60% yield along with 15% of 10a). Here again, when isolated 9a was heated in reflux in pyridine, the N-amidation compound 10a was formed.

Figure 11:
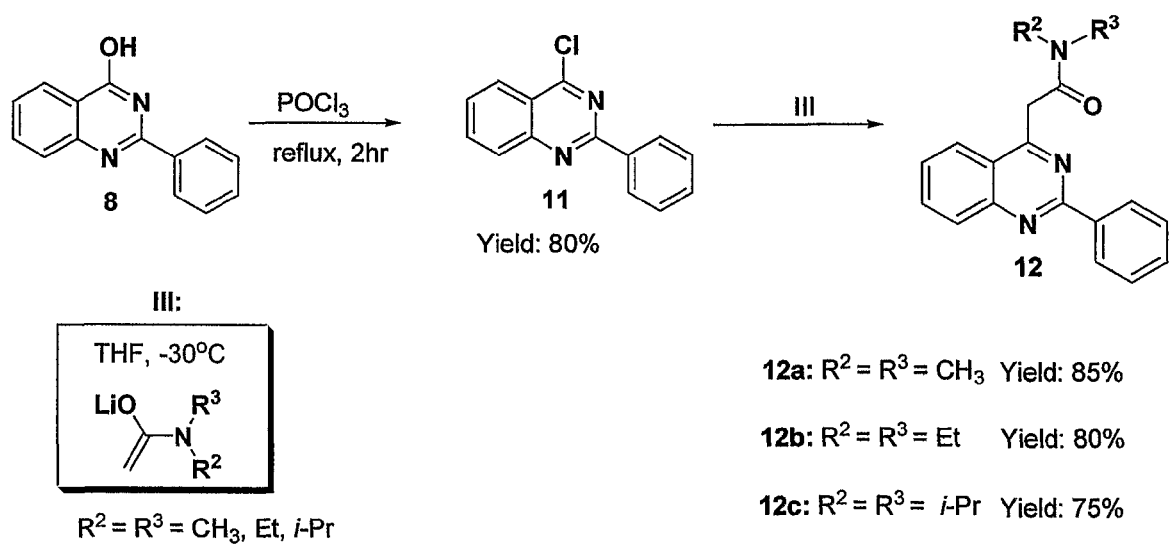

Other quinazoline derivatives of formula IIB were prepared as described in FIG. 11 and as further detailed in Example 4. The reaction involved (1) chlorination of the alcohol 8 and (2) nucleophilic substitution of the leaving group by lithium enolate.

Dimethyl 12a, diethyl 12b and diisopropyl-phenylquinazoline 12c acetamides were synthesized in good yields. The structure of 12b has been determined by X-Ray analysis.

Figure 12:
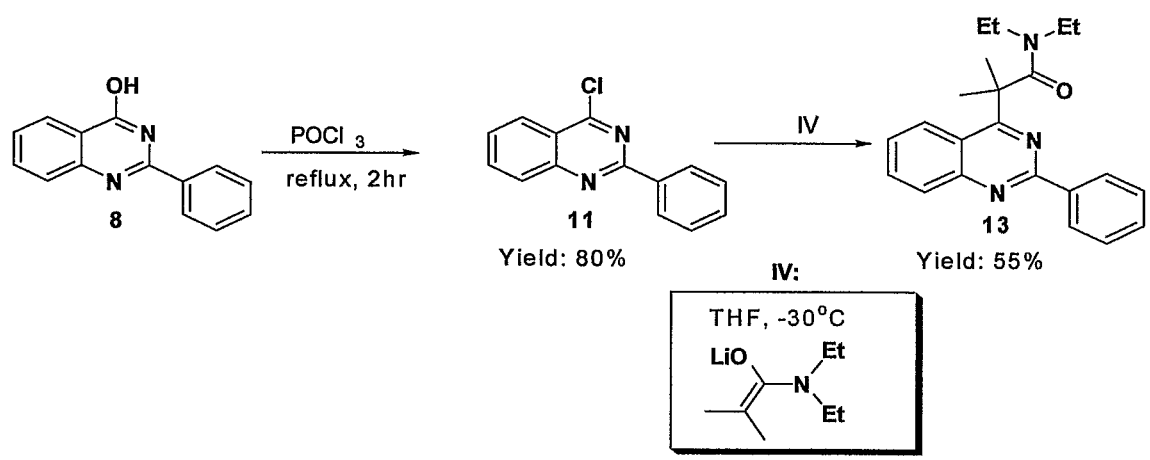
Figure 13:
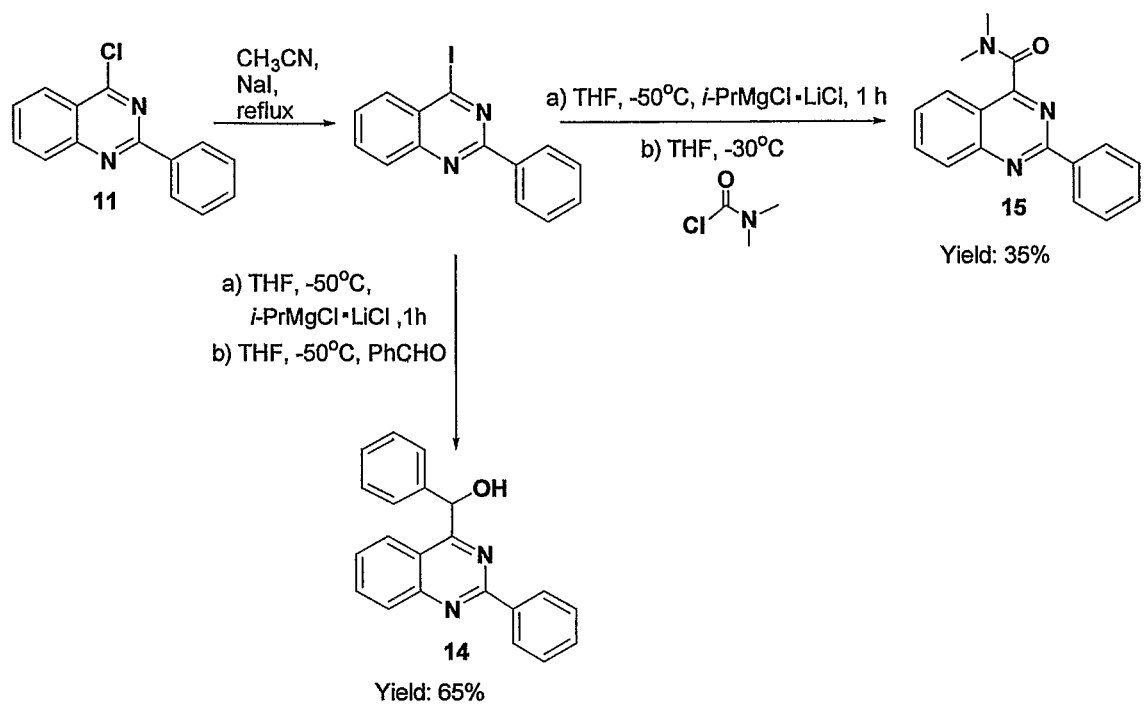
Figure 14:
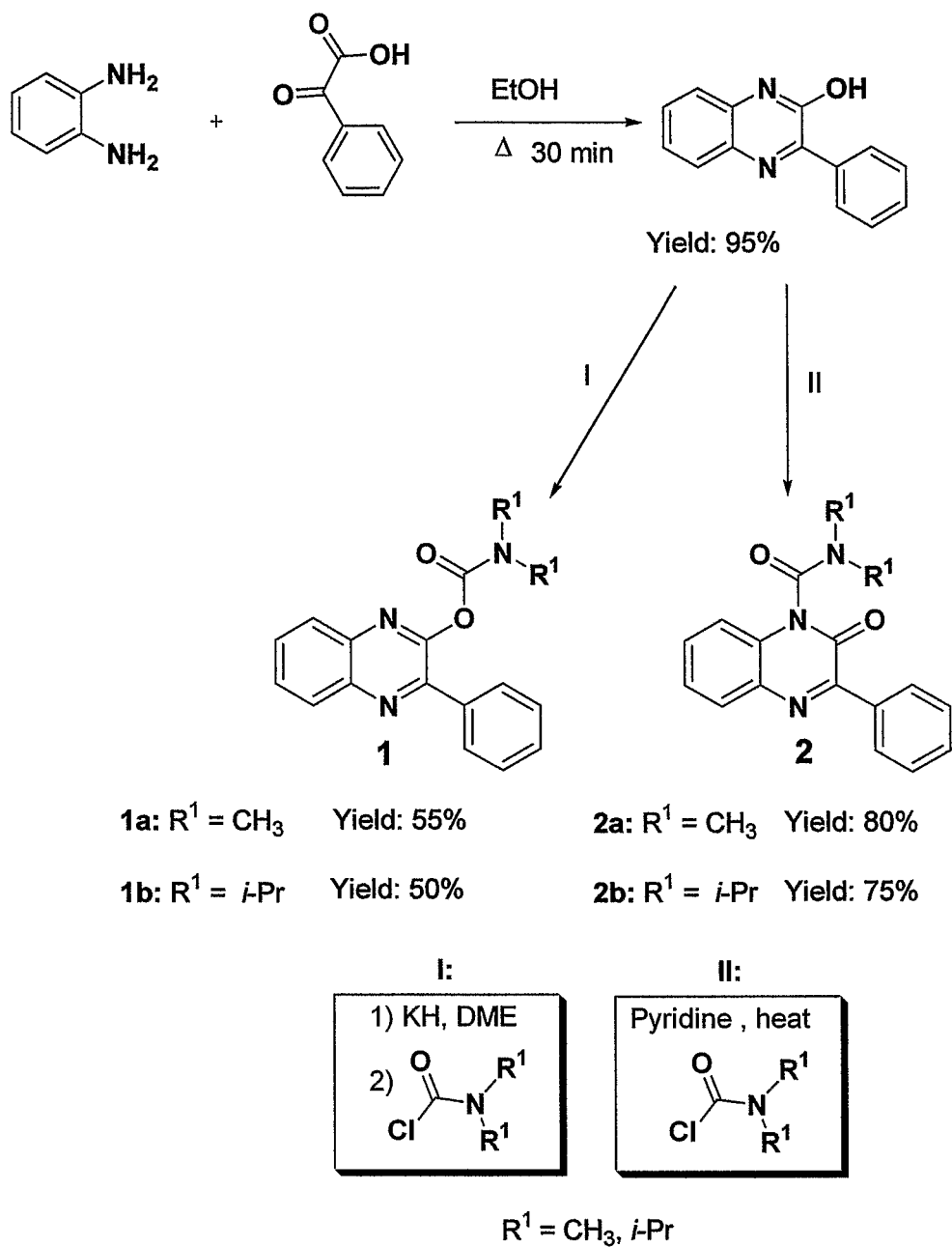
FIG. 14-18: Synthesis of quinoxaline derivatives.

Other quinazoline derivatives of formula IIB were prepared as described in FIGS. 12 and 13 and as further detailed in Example 4. For the preparation of compound 13, compound 8 was converted to compound 11, followed by reaction with reagent IV (FIG. 12). The synthesis of N,N-dimethyl-2-phenylquinazoline-4-carboxamide 15 was performed in two chemical steps (FIG. 13), starting from the previously described 4-chloro-2-phenylquinazoline 11.

c. Quinoxalines

Quinoxaline derivatives of formula IIIA and IIIB were prepared as described in FIGS. 14-18 and as further detailed in Example 4.

Commercially available o-phenylene diamine and hippuric acid were mixed in ethanol to gave 3-phenylquinoxalin-2-ol in excellent yield. The latter was then transformed into the corresponding potassium alcoholate and treated with two different carbamoyl chloride derivatives ($R^1$=CH$_3$, i-Pr). The expected products 1a and 1b (see FIG. 14) were easily obtained in moderate yields. The structures of 1b, 2a and 2b have been determined by X-Ray analysis.

Figure 15:
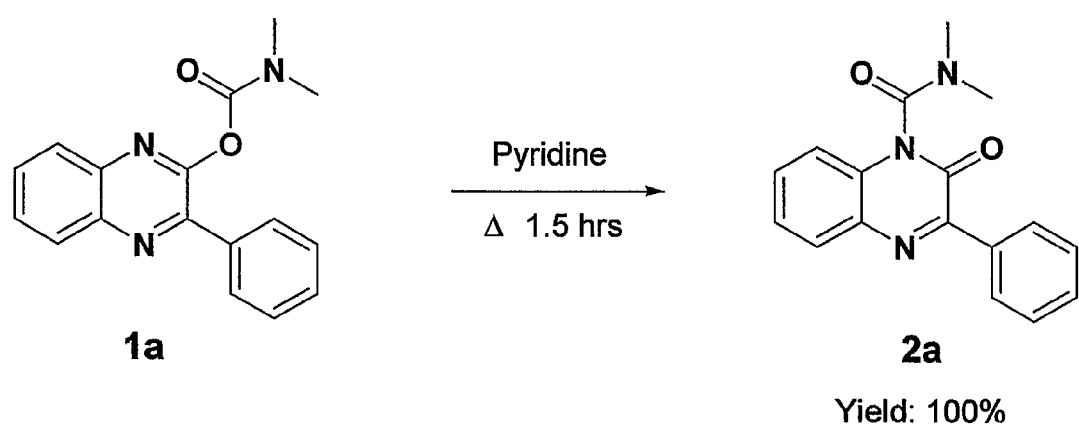

When the 3-phenylquinoxalin-2-ol was treated with the same carbamoyl chlorides but in the presence of a base (pyridine) at reflux, the N-amidation products 2 were obtained. Interestingly, when 1a was heated for 1.5 hours in pyridine, the corresponding rearranged product 2a was formed (FIG. 15).

It should be noted that both 1 and 2 were always obtained as a mixture of products. No deeper investigation was performed to obtain quantitatively only one of these two isomers.

Figure 16:
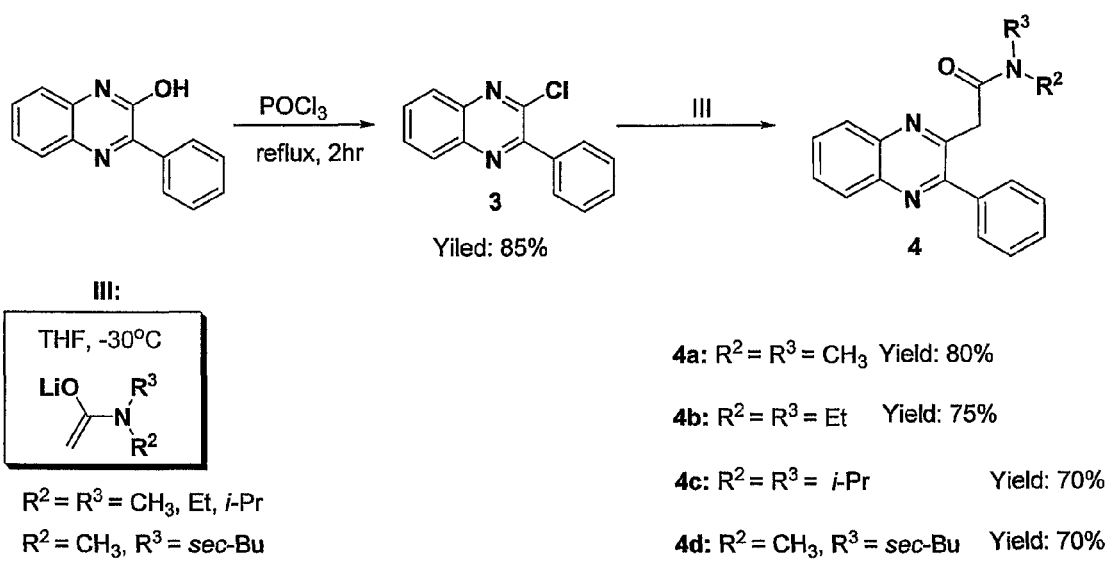

From the same common intermediate 3, new derivatives 4a, 4b, 4c, 4d were easily prepared as described in FIG. 16. First, the alcohol moiety of 3-phenylquinoxalin-2-ol was easily transformed into the corresponding chloride 3. Then, the 2-chloro-3-phenylquinoxaline was treated with a large variety of lithium enolates to give the expected products in good overall yields.

Dimethyl 4a, diethyl 4b, diisopropyl 4c and sec-butyl-methyl-phenylquinoxaline 4d acetamides were respectively prepared by this strategy. All of these derivatives were synthesized to examine the influence of substituents on the nitrogen atom of the amide on the ligand efficacy.

Figure 17:
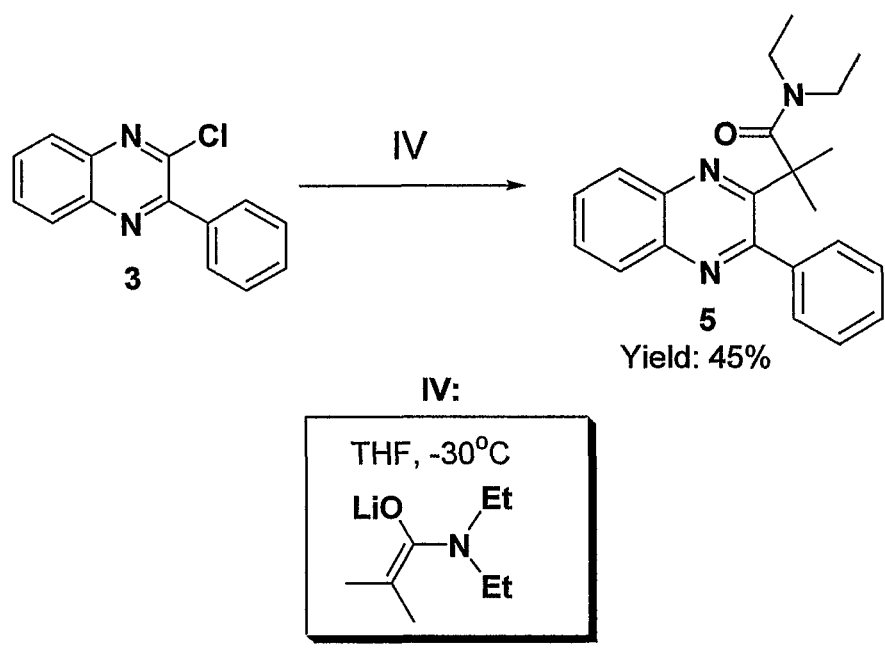
Figure 18:
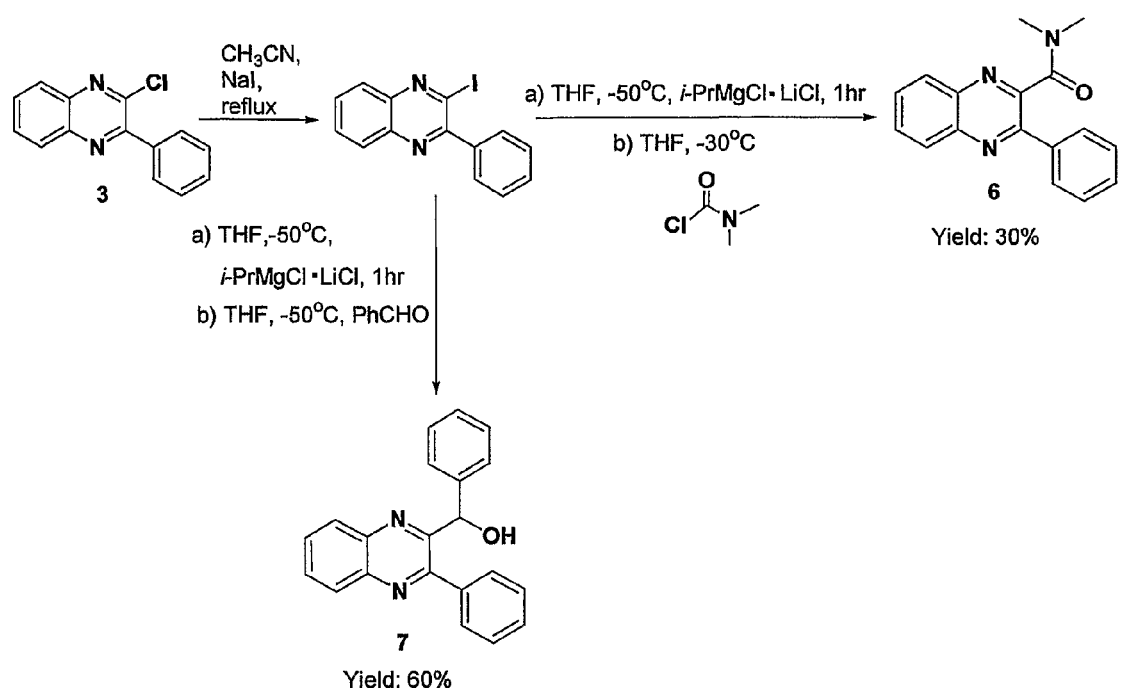

Moreover, an additional product 5 was prepared without any acidic hydrogens α to the carbonyl. Indeed, we found that compounds 4a-c could be present in different tautomeric forms and we thought that it may influence the binding affinity. Therefore, by reaction of the enolate of N,N-diethyl-isobutyramide with 3, the corresponding bisalkylated product 5 was formed in moderate yield (FIG. 17).

The synthesis of N,N-dimethyl-3-phenylquinoxaline-2-carboxamide 6 was performed in two distinct chemical steps (FIG. 18), starting from the previously described 2-chloro-3-phenylquinoxaline.

2-Chloro-3-phenylquinoxaline was quantitatively converted into 2-iodo-3-phenylquinoxaline by treatment with NaI in refluxing acetonitrile. Then, by a iodine-magnesium exchange reaction, the corresponding metallated species were obtained and treated with different electrophiles for further functionalizations. Then, the same reaction was performed again and N,N-dimethyl carbamoyl chloride was added. The functionalized quinoxaline 6 was obtained in low yield.

d. Dimers

Figure 19:
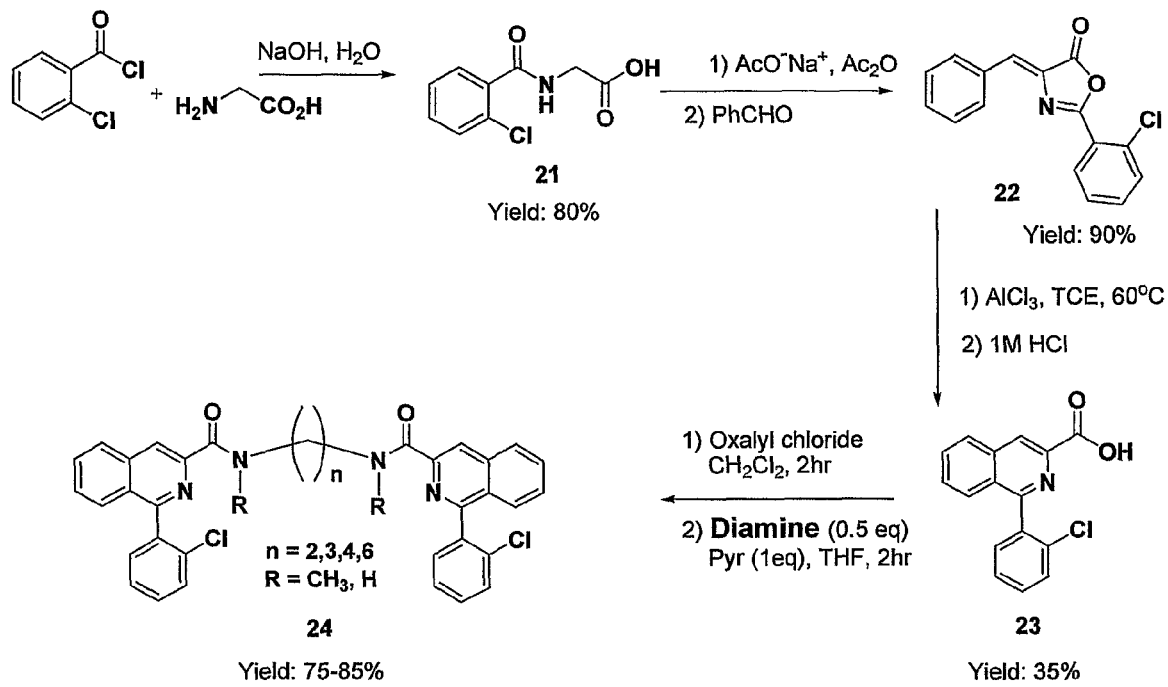
FIG. 19: Synthesis of dimers of PK 11195.

Dimers of formula 24a-e were prepared as described in FIG. 19 and as further detailed in Example 4.

Commercially available 2-chlorobenzoyl chloride was treated with glycine to give 2-(2-chlorobenzamido)acetic acid 21 in good yield. Then, 21 was reacted with acetic anhydride and benzaldehyde, in the presence of sodium acetate, to lead to the corresponding oxazolone in excellent yield. The resulting (4Z)-4-benzylidene-2-(2-chlorophenyl)oxazol-5(4H)-one 22 was converted via a Friedel-Crafts reaction to 1-(2-chlorophenyl)isoquinoline-3-carboxylic acid 23 in moderate yield[2]. Finally, the dimeric compounds 24 were easily obtained in good yields by transformation of the acid into acylchloride and further reactions with diamines.

EXAMPLE 3

Results

Figure 7:
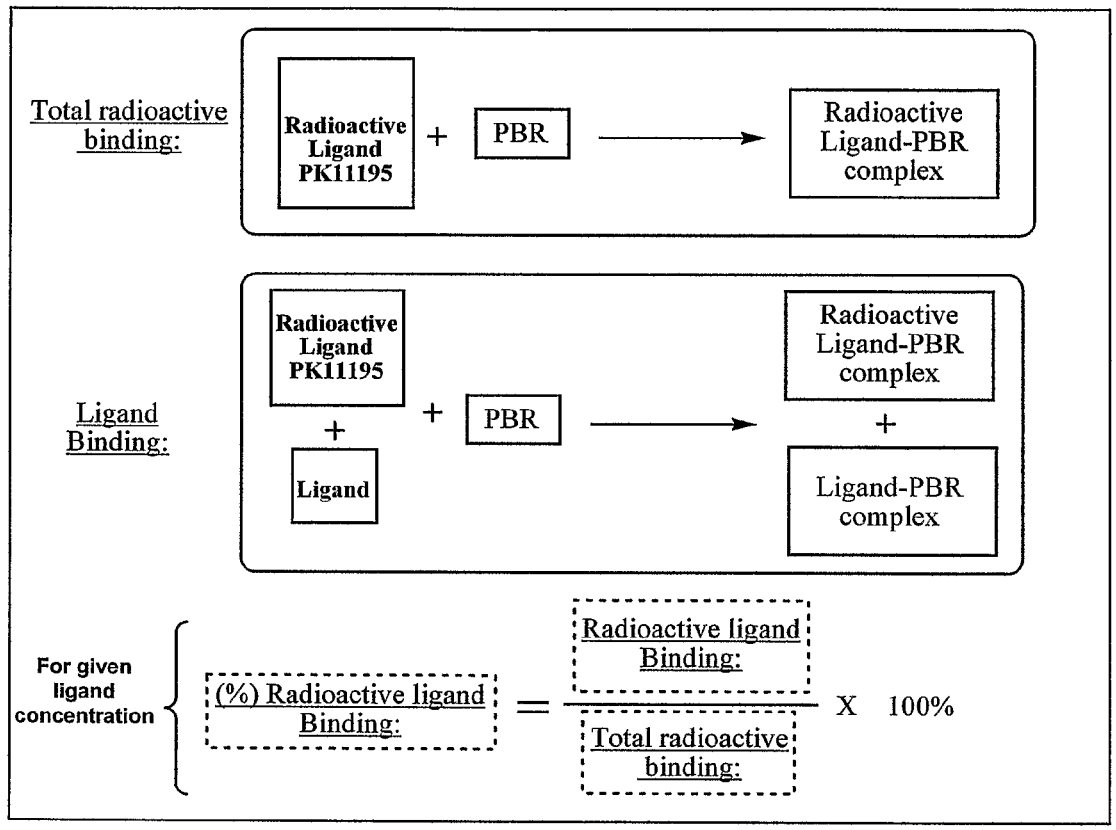
FIG. 7: PBR-binding assay: [3H] PK11195 radio-assay.

Binding to the PBR was evaluated for all the phthalazine, quinazoline and quinoxaline derivatives of the invention with the help of [$^3$H] PI(11195 radio-assay, as previously described (see FIG. 7).

a. Phthalazines

Figure 20:
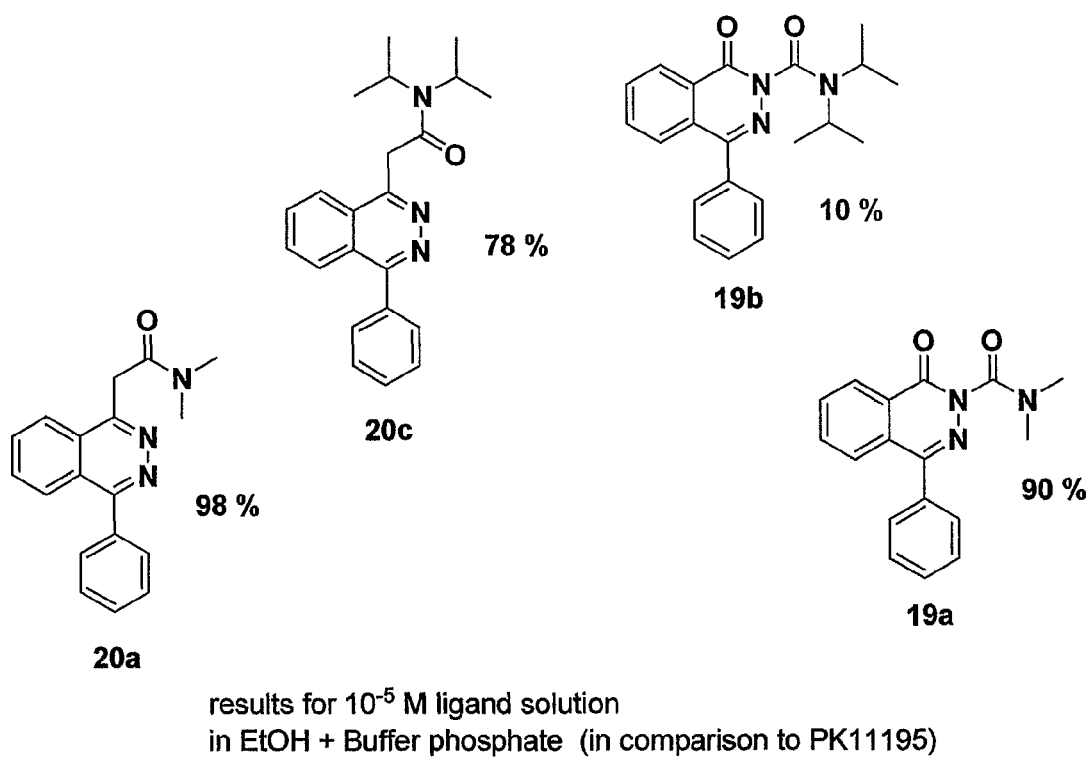
FIG. 20: Results of binding to PBR for phthalazine derivatives.

Results of binding to PBR for several exemplary phthalazine derivatives are presented in FIG. 20.

As can be seen from the results, one compound in particular—19b presented excellent binding to PBR: only 10% of the radioactive standard remained bound to PBR. Compound 19b, appeared to be able to displace [$^3$H]PK 11195 in binding assays in the same range as non-radioactive PK 11195 does [Alex Shterenberg, M. Sc. thesis, 2006]. Favorably, this compound also showed anti-apoptotic effects in glial and neuronal cell cultures. In particular, compound 19b shows anti-apoptotic effects in a concentration dependent manner. Moreover, compound 19b, lacks the toxic effects at high concentrations often displayed by classical PBR ligands.

Figure 24:
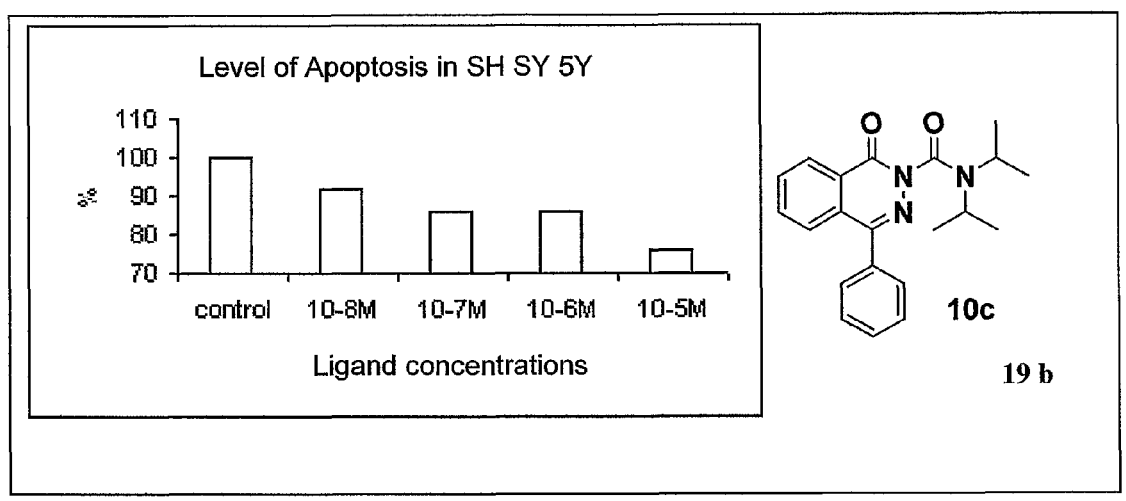
FIG. 24: Level of basal apoptosis vs. concentration of compound 19b.

As can be seen in FIG. 24, compound 19b showed anti-apoptotic properties in a concentration dependent manner. There is a decrease of the apoptosis level with increase in compound 19b concentration: down to 75% of basal apoptotic levels in the cells treated with $10^{-5}$M ligand solution.

Figure 25:
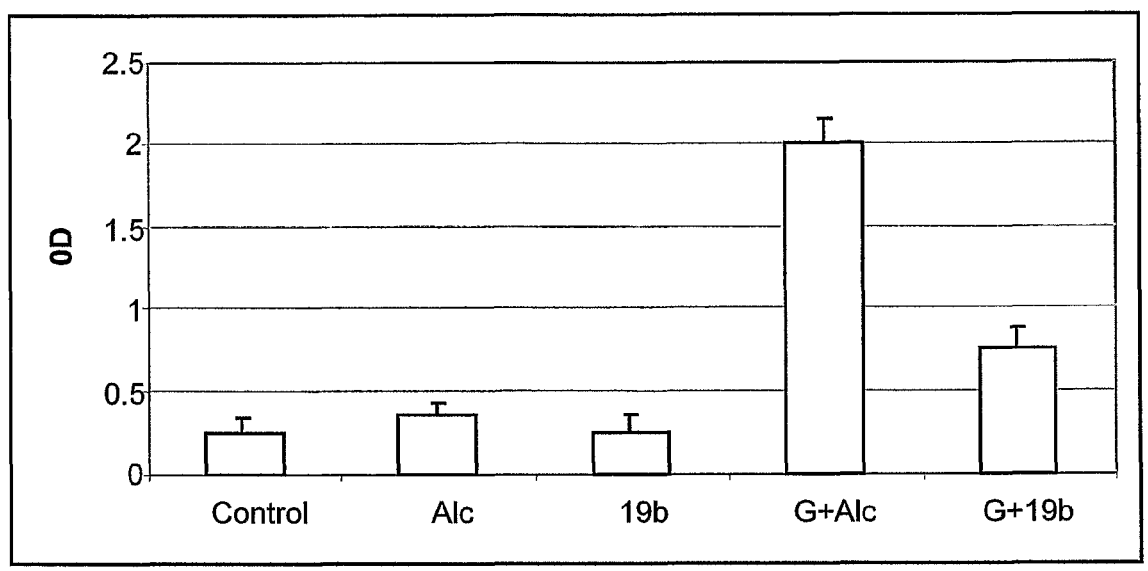
FIG. 25: Treatment with glutamate $10^{-4}$M (G) together with 0.1% alcohol (Alc), the vehicle of compound 19b, induces apoptosis in the neuronal cell line SH SY 5Y, in comparison to untreated SH SY 5Y cells (Control), cells treated with the vehicle (Alc), or treated with $10^{-5}$M compound 19b dissolved in its vehicle. Alcohol and compound 19b did not appear to have effects on apoptosis by themselves at these concentrations used in comparison to untreated cells. Adding compound 19b to cells treated with glutamate (IC+G) considerably and significantly reduced apoptotic levels in comparison to cells treated by glutamate alone (P<0.001). OD optical density indicative of apoptotic levels.

In addition, it has been found that compound 19b reduced neurotoxic effects of glutamate (FIG. 25). Glutamate is one of the agent responsible for propagating neuronal damage following injury and in neurodegenerative disease. In contrast to classical PBR ligand, compound 19b, does not show pro-apoptotic effects at high concentrations. Furthermore, classical PBR ligands often are pro-apoptotic in synergy with other, proaptotic drugs. This appears not to be the case with compound 19b. Thus, it is envisioned that compound 19b will be relatively safe to use.

In conclusion, compound 19b and related compounds may have potential to be used as a drug with neuroprotective capacities for the prevention of secondary brain damage after brain trauma. In addition, this drug type may be used to treat degenerative diseases, including but not restricted to, Alzheimer disease, Parkinson disease, etc.

b. Quinazolines

Figure 21:
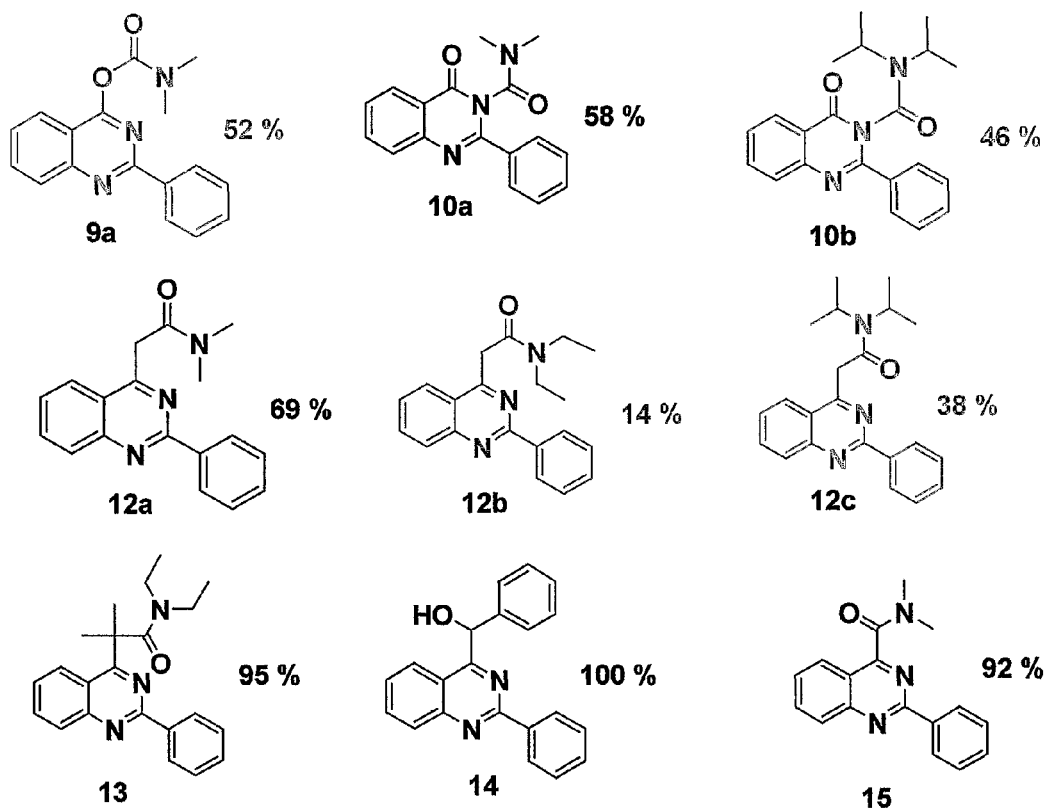
FIG. 21: Results for binding to PBR for quinazoline derivatives.

Results of binding to PBR for several exemplary quinazoline derivatives are presented in FIG. 21.

Without wishing to be bound by any particular mechanism or theory, a comparison of compounds 9a, 10a, and 12a suggests that the distance from the aryl ring attached to the central core to the amide moiety of the molecule affects binding: longer distance provides better binding. Upon comparison between molecules 12a, 12b, and 12c it can be hypothesized that the nature of the alkyl substituents on the amide moiety has a strong effect on the binding: while changing the methyl substituent to ethyl or i-propyl groups, the effect is notable. The same effect is observed when 10a is compared to 10b. Furthermore, it appears that the carbonyl group plays a role in binding.

In conclusion, four quinazoline derivatives 9a, 10b, 12c and 12b had good binding properties to PBR. The best candidate being the ligand 12b, where only 14% of the radioactive standard remained bound to PBR.

c. Quinoxalines

Figure 22:
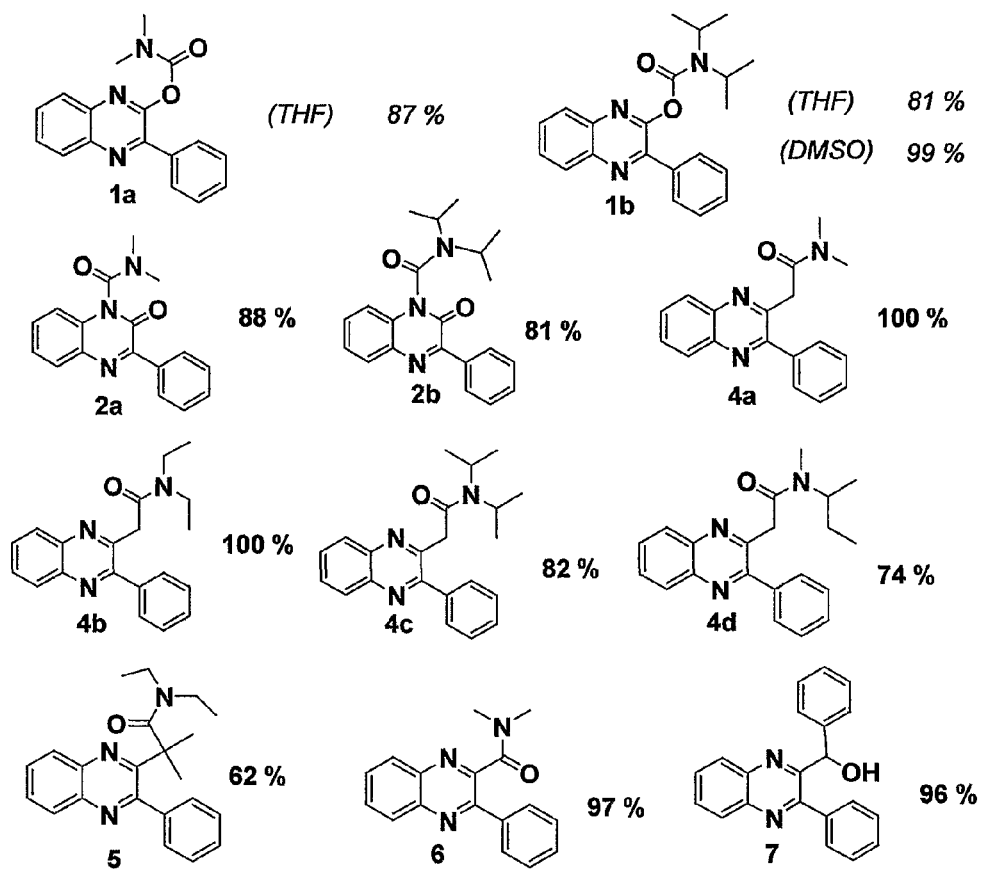
FIG. 22: Results for binding to PBR for quinoxaline derivatives.

Results of binding to PBR for several exemplary quinoxaline derivatives are presented in FIG. 22.

Without wishing to be bound by any particular mechanism or theory, it is believed that several structural features influence the binding affinity of new ligands to PBR. A comparison of compound 2a with the compound 6, suggests that a longer distance from the aryl ring attached to the central core to the amide moiety, enhances is the binding. A comparison between molecules 2a and 2b, 4a and 4c, 1a and 1b suggests that that bigger are the alkyl substituents on the amide moiety, enhance the binding. Compound 5 showed the best binding, suggesting that acidic hydrogens α to the carbonyl may also have an effect.

d. Dimers of PK 11195

Figure 23:
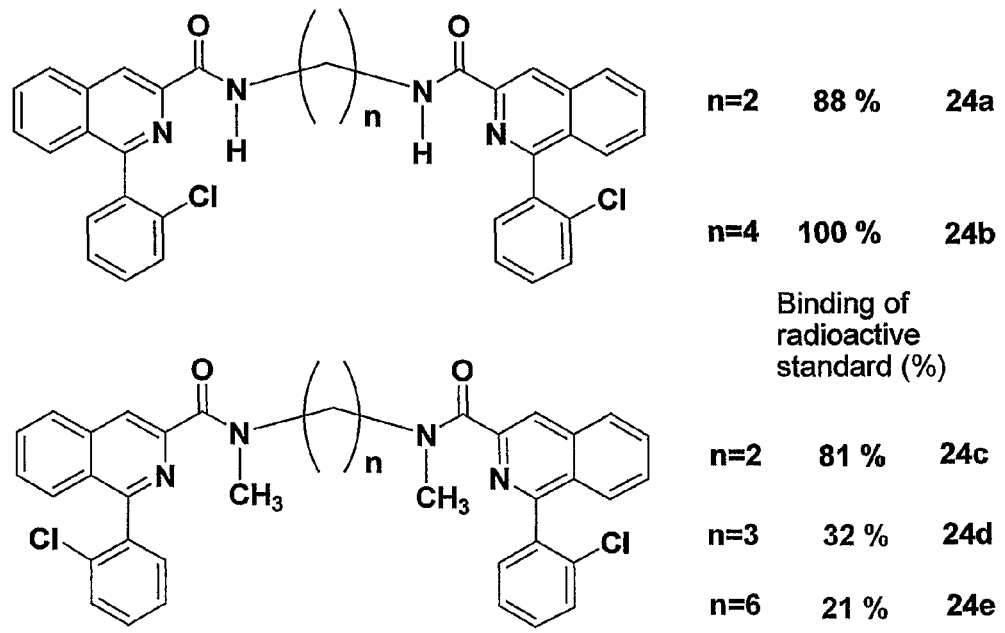
FIG. 23: Results for binding to PBR for dimers of PK 11195.

Results of binding to PBR for several exemplary dimers are presented in FIG. 23.

As can be seen from these results, two compounds from all the tested candidates (24d and 24e) showed good binding to PBR, with compounds 24d and 24e showing particularly good binding. Without wishing to be bound by any particular mechanism or theory, it is believed that there is an effect of alkyl substituent (methyl) at the nitrogen atom of the amide moiety on the binding affinity of the PK 11195 dimer, as can be seen from the results. In addition there is an increase in the binding of the PK 11195 dimer to PBR with a longer bridge between the two monomeric subunits of the molecule (FIG. 23).

Figure 26:
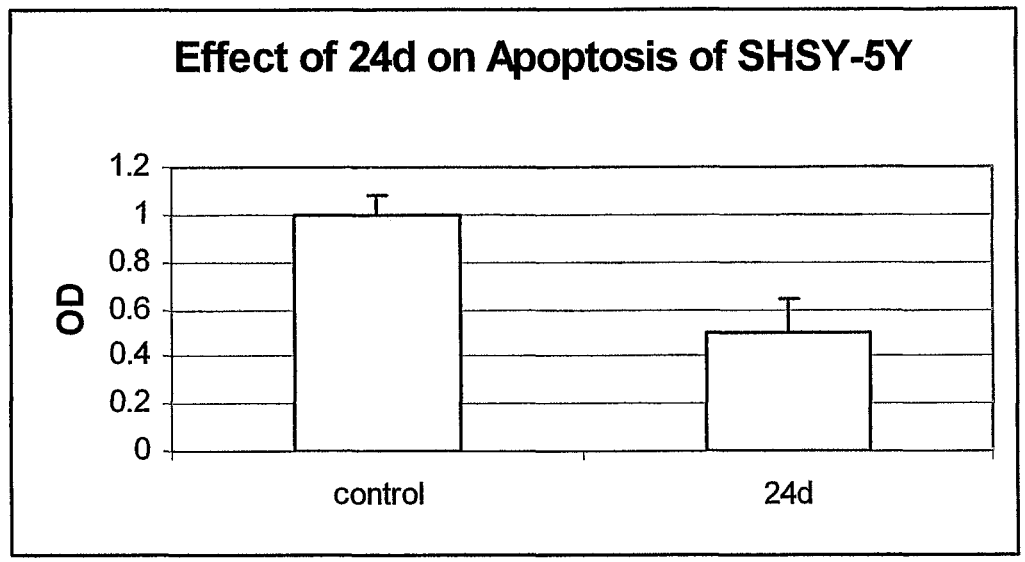
FIG. 26: Effect of compound 24d on apoptotic levels of SH SY 5Y cells, as compared to basal apoptotic levels of SH SY 5Y cells.

As shown in FIG. 26, a PK 11195 dimer 24d ($10^{-5}$M) causes a 50% decrease in apoptotic levels of SH SY 5Y cells, as compared to basal apoptotic levels of SH SY 5Y cells ($P<0.01$). Application of the dimer 24d therefore significantly reduced apoptotic levels in SHSY-5Y cells.

EXAMPLE 4

Synthesis Protocols

All the solvents were purified by distillation before use. THF and diethyl ether were distilled from sodium-benzophenone under argon. 1,2-Dimethoxyethane and acetonitrile were distilled from $CaH_2$. All the reactions were followed by TLC. All the synthesized compounds were characterized by $^1H$ and $^{13}C$ NMR, MS-measurements and X-ray analysis.

General Procedure I:

To the suspension of (6.75 mmol) potassium hydride under argon in 30 ml of 1,2-dimethoxyethane was added the alcohol (4.5 mmol) in one portion. The reaction mixture was stirred for 30 minutes, and the carbamoyl chloride (7 mmol) was added to the reaction mixture. Reaction mixture was brought to reflux for 2.5 hrs. The reaction was quenched with 30 ml of water, followed by extraction with dichloromethane. Combined organic phases were dried over $MgSO_4$ and the solvents were evaporated under reduced pressure. The resulting crude product was purified by silica gel chromatography.

General Procedure II

The mixture of alcohol (3.9 mmol) and carbamoyl chloride (5.1 mmol) in 15 ml of pyridine was heated to 110° C. overnight and then quenched with 35 ml of an aqueous solution of 1M HCl. Extraction with dichloromethane and drying over $MgSO_4$ was followed by evaporation of the solvents and azeotropic removal of pyridine (with hexane). The resulting crude product was purified by silica gel chromatography.

General procedure III:

A mixture of alcohol (7 mmol) and phosphorus oxychloride (25 ml) was heated at reflux for 30 minutes. After cooling, the reaction mixture was poured into a cold water-ice solution and the resulting solid was filtered off. The resulting crude product was purified by silica gel chromatography.

General Procedure IV:

A dry and argon-flushed flask, equipped with a magnetic stirrer and a septum, was charged with 20 ml of freshly distilled THF and diisopropylamine (3.1 mmol). The reaction mixture was cooled to −50° C., and a solution of n-BuLi (3.2 mmol, 1.5 M in hexane) was added dropwise, keeping the temperature below 0° C., and stirred for 30 min at 0° C. Then, the reaction mixture was cooled to -20° C., the corresponding N,N-dialkyl acetamide (1.3 mmol) was added dropwise and the mixture was stirred for an additional 30 min at 0° C. Electrophiles (1 mmol) in 5 ml of THF was added dropwise to the reaction at −50° C. The reaction mixture was stirred at −30° C. for 30 min and then, at 0° C. for 2 hrs. The reaction was quenched with 1 M HCl (30 ml) and extracted with diethyl ether. The combined organic layers were dried over $MgSO_4$ and the solvents were evaporated under reduced pressure. The resulting crude product was purified by silica gel chromatography.

General Procedure V:

A dry and argon-flushed flask, equipped with a magnetic stirrer and a septum, was charged with a solution of the aryl iodide (1 mmol) in dry THF (10 ml). i-PrMgCl—LiCl (1.5 M in THF, 1.2 mmol) was added slowly at −50° C., and the resulting mixture was stirred at this temperature for 1 hour to complete the iodine-magnesium exchange (checked by TLC). The desired electrophile (1.3 mmol) was added at −30° C. and the reaction mixture was gradually heated to 0° C. during 2 hours. The reaction was quenched with a saturated aqueous $NH_4Cl$ solution. The aqueous phase was extracted with dichloromethane, the combined organic phases were dried over $MgSO_4$ and the solvents were evaporated under reduced pressure. The resulting crude product was purified by silica gel chromatography.

General Procedure VI:

1-(2-Chloro-phenyl)-isoquinoline-3-carboxylic acid 23 (2.12 mmol) was suspended in dry $CH_2Cl_2$ (20 ml) and oxalyl chloride (4.24 mmol) was added followed by 2 drops of dimethyl formamide. The mixture was stirred at r.t. for 2 hrs. The solvent was removed under reduced pressure and traces of oxalyl chloride were removed by the addition and subsequent evaporation of toluene (2×3 ml). The residue was dissolved in dry THF (30 ml), cooled with an ice bath and pyridine (2.12 mmol) with the corresponding diamine (1.06 mmol) were added to the reaction mixture. The reaction mixture was stirred at r.t. for additional 3 hrs. Water (50 ml) was added to the reaction, followed by extraction of aqueous layer with ethyl acetate, the combined organic layers were dried over $MgSO_4$ and solvents were removed by reduced pressure. The resulting crude product was purified by alumina (neutral) chromatography.

3-Phenylquinoxalin-2-ol

Phenylglioxalic acid (26.6 mmol) was mixed with o-phenylenediamine (40 mmol) and stirred in 40 ml of ethanol for 30 min. The reaction mixture was filtered to give, after evaporation of solvent, the crude product. Recrystallization from ethanol gave pure yellow crystals in 95% yield.

$^1H$ NMR (300 MHz, DMSO-$d_6$) δ (ppm): 12.54 (s, 1H), 8.27-8.24 (m, 2H), 7.8 (d, J=8.1 Hz, 1H), 7.52-7.45 (m, 4H), 7.31-7.26 (m, 2H). $^{13}C$ NMR (75 MHz, DMSO-$d_6$) δ (ppm): 154.6, 135.6, 132.0, 130.3, 130.2, 129.2, 128.8, 127.8, 123.4, 115.1.

2-Phenyl-quinazolin-4-ol (8)

A mixture of o-aminobenzoate (7 mmol), benzaldehyde (7 mmol) and sodium hydrogen sulfite (10.5 mmol) in dimethylacetamide (10 ml) was heated with stirring at 150° C. overnight. Then, the reaction mixture was poured into water (300 ml). A precipitate was formed, collected and dried. Recristallization from benzene gave the desired product in 85% yield.

$^1H$ NMR (300 MHz, DMSO-$d_6$) δ (ppm): 8.29-8.25 (m, 3H), 7.94 (t, J=7 Hz, 1H), 7.85 (d, J=8 Hz, 1H), 7.71-7.61 (m, 4H). $^{13}C$ NMR (75 MHz, DMSO-$d_6$) δ (ppm): 164.6, 154.6, 150.9, 136.8, 135.0, 133.6, 130.9, 130.0, 129.7, 128.8, 128.1, 123.2.

2-Dimethylamino-isoindole-1,3-dione (16)

To the suspension of phthalic anhydride (62.5 mmol) in toluene (500 ml), N,N-dimethyl hydrazine dihydrochloride (50 mmol) and diethyl-phenyl-amine (90 mmol) were added. The reaction mixture was refluxed for 18 hours while removing the formed water via a Dean-Stark trap. Then, toluene was evaporated under reduced pressure and the resulting crude was purified on silica gel chromatography with (1:5) EtOAc: dichloromethane, to give the desired product in 85% yield.

¹H NMR (300 MHz, CDCl₃) δ (ppm): 8.30-8.25 (dd, J=6 Hz, J=3.3 Hz, 2H), 7.78-7.73 (dd, J=5.7 Hz, J=3.3 Hz, 2H), 3.94 (s, 6H). ¹³C NMR (75 MHz, CDCl₃) δ (ppm): 159.6, 135.1, 130.6, 129.3, 35.0.

2-Benzoyl-benzoic acid N',N'-dimethyl-hydrazide (17)

A solution of phenylmagnesium bromide in THF (11.6 mmol) was slowly added to a solution of phthalimide 16 (10.5 mmol) in THF (110 ml) at −78 °C. and stirred under argon for 15 minutes. The mixture was then progressively warmed to −30 °C. for 1 hour. The reaction was quenched with a saturated aqueous solution of NH₄Cl (15 ml) and the aqueous layer extracted with Et₂O. The combined organic layers were washed with brine (20 ml), dried over MgSO₄ and the solvent was evaporated under reduced pressure. The resulting crude product was purified by silica gel chromatography with (1:2) EtOAc:hexane, to give 80% yield of the desired product.

¹H NMR (300 MHz, CDCl₃) δ (ppm): 7.95 (d, J=7.8 Hz, 1H), 7.68-7.65 (m, 2H), 7.48 (t, J=6.9 Hz, 1H), 7.29-7.20 (m, 5H), 3.33 (s, OH), 2.95 (s, 3H), 2.55 (s, 3H). ¹³C NMR (75 MHz, CDCl₃) δ (ppm): 165.0, 145.7, 139.5, 134.2, 130.8, 130.4, 130.3, 129.2, 129.0, 128.1, 127.9, 90.4, 37.3, 35.3.

4-Phenyl-2H-phthalazin-1-one (18)

A mixture of 2-benzoyl-benzoic acid N',N'-dimethyl-hydrazide 17 (1 mmol) and H₂NNH₂.H₂O (18 mmol) was stirred for 2 hrs at 100° C. After the excess hydrazine was removed under reduced pressure, the crude product was purified by chromatography on silica gel ((1:2) EtOAc:hexane) to give the desired product in 95% yield.

¹H NMR (300 MHz, CDCl₃) δ (ppm): 11.10 (s, NH), 8.67 (d, J=3.9 Hz, 1H), 7.94-7.90 (m, 3H), 7.72-7.64 (m, 5H). ¹³C NMR (75 MHz, CDCl₃) δ (ppm): 162.2, 150.1, 136.8, 135.2, 133.4, 131.5, 131.2, 131.0, 130.4, 130.2, 129.3, 128.8, 128.7, 127.6.

2-Iodo-3-phenylquinoxaline

To the 2-chloro-3-phenylquinoxaline (4.15 mmol) in dry THF (10 ml) was added a solution of 2 M HCl in ether (4 ml). After 5 minutes the solvents were removed by vacuum. Dry sodium iodide (41.5 mmol) and acetonitrile (30 ml) were added to the hydrochloride salt and refluxed for 5 hrs. The reaction was quenched by the addition of an aqueous solution of 10% K₂CO₃ and 5% NaHSO₃ (15 ml). After extraction with dichloromethane, and drying the combined organic layers over MgSO₄ the solvents were evaporated under reduced pressure. The resulting crude product was purified by silica gel chromatography with (1:10) EtOAc:hexane, to give 95% yield of the desired product.

¹H NMR (300 MHz, CDCl₃) δ (ppm): 8.07-8.02 (m, 2H), 7.75-7.65 (m, 4H), 7.46 (t, J=7.2 Hz, 3H).

HRMS: m/z calcd for C₁₄H₉IN₂: 331.9811. Found: 331.9810.

4-Iodo-2-phenylquinazoline

To the 4-chloro-2-phenylquinazoline (4.15 mmol) in dry THF (10 ml) was added a solution of 2 M HCl in ether (4 ml). After 5 min the solvents were removed by vacuum. Dry sodium iodide (41.5 mmol) and acetonitrile (30 ml) were added to the hydrochloride salt and refluxed for 4 hrs. The reaction was quenched by the addition of an aqueous solution of 10% K₂CO₃ and 5% NaHSO₃ (15 ml). Extraction with dichloromethane and drying of the combined organic layers was followed by evaporation of solvents under reduced pressure. The resulting crude product was purified by alumina chromatography with (1:10) EtOAc:hexane, to give 95% yield of the desired product.

¹H NMR (300 MHz, CDCl₃) δ (ppm): 8.55-8.49 (m, 2H), 7.93-7.89 (m, 2H), 7.83 (t, J=5.6 Hz, 1H), 7.59 (t, J=8.1 Hz, 1H), 7.48-7.45 (m, 3H).

MS: m/z calcd for C₁₄H₉IN₂: 331.98. Found MH⁺: 333.

(2-Chloro-benzoylamino)-acetic acid (21)

To a stirred solution of glycine (100 mmol) and NaOH (100 mmol) in water (300 ml), at 5° C., o-chloro-benzoyl chloride (110 mmol) was added in small portions. The reaction mixture was stirred for 30 minutes at room temperature, then cooled again and acidified to pH=2 by addition of 6 M HCl. Extraction of the aqueous solution was performed with EtOAc. Then, the combined organic layers were dried over MgSO₄ and the solvent was removed by reduced pressure. The residue was triturated in boiling chloroform, and the product was collected by filtration in 80% yield.

¹H NMR (300 MHz, CDCl₃) δ (ppm): 12.64-12.56 (br, 1H), 8.68 (t, J=6 Hz, 1H), 7.42-7.35 (m, 3H), 3.84 (d, J=6 Hz, 2H). ¹³C NMR (75 MHz, CDCl₃) δ (ppm): 170.9, 166.6, 136.2, 131.0, 130.0, 129.7, 129.1, 127.1, 40.9.

4-Benzylidene-2-(2-chloro-phenyl)-4H-oxazol-5-one (22)

To the stirred mixture of (2-chloro-benzoylamino)-acetic acid 21 (23.41 mmol), anhydrous sodium acetate (70.23 mmol), acetic anhydride (7 ml), and benzaldehyde (25.75 mmol) were added dropwise at 30° C. This mixture was then heated to 60° C. for 1 hr. The reaction mixture was poured into an ice-water solution and the resulting solids were filtered, washed with ethanol and dried on vacuum. The desired compound was obtained with a 90% yield.

¹H NMR (300 MHz, CDCl₃) δ (ppm): 8.18-8.13 (m, 2H), 8.03 (d, J=7.5 Hz, 1H), 7.53 (d, J=8.1 Hz, 1H), 7.46-7.33 (m, 5H), 7.26 (s, 1H). ¹³C NMR (75 MHz, CDCl₃) δ (ppm): 168.9, 163.3, 143.6, 136.4, 135.1, 134.8, 134.6, 134.4, 133.9, 133.8, 133.7, 133.3, 130.8, 128.8, 126.0.

MS: m/z calcd for C₁₆H₁₀ClNO₂: 283.71. Found M⁺: 284.

1-(2-Chloro-phenyl)-isoquinoline-3-carboxylic acid (23)

A solution of 22 (12 mmol) in tetrachloroethane was added to the suspension of AlCl₃ (36 mmol) in tetrachloroethane (50 ml). The resulting mixture was heated to 60° C. for 1.5 hrs. The reaction mixture was quenched by addition of 1 M HCl (50 ml). Then, the mixture was basified by addition of NaOH (1M aqueous solution), the resulted layers were separated, and the aqueous layer was acidified by HCl (aqueous solution). This aqueous phase was extracted with CH₂Cl₂, dried over MgSO₄ and finally the solvents were removed under reduced pressure, to give 35% yield of the desired product.

¹H NMR(300 MHz, CDCl₃) δ (ppm): 8.71 (s, 1H), 8.11 (d, J=8.1 Hz, 1H), 7.83 (t, J=6.6 Hz, 1H), 7.77-7.64 (m, 2H), 7.59 (d, J=7.5 Hz, 1H), 7.53-7.44 (m, 3H). ¹³C NMR (75 MHz, CDCl₃) δ (ppm): 164.8, 157.9, 138.6, 136.7, 133.3, 131.7, 131.2, 130.6, 130.2, 130.0, 129.0, 128.8, 127.8, 126.9, 122.7.

MS: m/z calcd for C₁₆H₁₀ClNO₂: 283.71. Found M⁺: 284.

Dimethyl-carbamic acid 3-phenyl-quinoxalin-2-yl ester (1a)

The general procedure I was applied for the preparation of 1a in 55% yield. Purification was performed with (1:5) EtOAc:hexane.

¹H NMR (300 MHz, CDCl₃) δ (ppm): 8.18-8.14 (m, 1H), 8.04-7.99 (m, 1H), 7.93-7.89 (m, 2H), 7.77-7.70 (m, 2H), 7.53-7.46 (m, 3H), 3.11 (s, 3H), 2.95 (s, 3H).

MS: m/z calcd for $C_{17}H_{15}N_3O_2$: 293.32. Found MH⁺: 294.

Diisopropyl-carbamic acid 3-phenyl-quinoxalin-2-yl ester (1b)

The general procedure I was applied for the preparation of 1b in 50% yield. Purification was performed with (1:5) EtOAc:hexane.

¹H NMR (300 MHz, DMSO-d₆) δ (ppm): 8.17 (m, 1H), 8.04 (m, 1H), 7.91-7.82 (m, 4H), 7.55-7.53 (m, 3H), 4.25 (t, J=6.6 Hz, 1H), 3.68 (t, J=6.6 Hz, 1H), 3.33 (d, J=7.2 Hz, 4H), 1.21 (d, J=6.6 Hz, 6H), 1.08 (d, J=6.6 Hz, 6H). ¹³C NMR (75 MHz, DMSO-d₆) δ (ppm): 150.7, 150.5, 149.6, 140.5, 139.4, 135.6, 130.8, 129.9, 129.6, 128.8, 128.7, 128.3, 127.7, 47.3, 45.4, 20.6, 19.8.

MS: m/z calcd for $C_{21}H_{23}N_3O_2$: 349.43. Found MH⁺: 350.1.

Dimethyl-carbamic acid 2-phenyl-quinazolin-4-yl ester (9a)

The general procedure I was applied for the preparation of 9a in 60% yield. Purification was performed with (1:40) EtOAc:dichloromethane.

¹H NMR (300 MHz, CDCl₃) δ (ppm): 8.53-8.50 (m, 2H), 8.07 (d, J=7.8 Hz, 2H), 7.86 (t, J=6.9 Hz, 1H), 7.56 (t, J=7.8 Hz, 1H), 7.49-7.44 (m, 3H), 3.17 (s, 3H), 3.15 (s, 3H). ¹³C NMR (75 MHz, CDCl₃) δ (ppm): 165.9, 162.2, 155.1, 136.1, 132.5, 130.5, 130.3, 130.2, 129.0, 125.2, 117.9, 38.9.

MS: m/z calcd for $C_{17}H_{15}N_3O_2$: 293.32. Found MH⁺: 294.

2-Oxo-3-phenyl-2H-quinoxaline-1-carboxylic acid dimethylamide (2a)

The general procedure II was applied for the preparation of 2a in 80% yield. Purification was performed with (1:5) EtOAc:hexane.

¹H NMR (300 MHz, CDCl₃) δ (ppm): 8.36-8.32 (m, 2H), 7.96-7.93 (dd, J=8.1 Hz, 1.5 Hz, 1H), 7.53-7.37 (m, 5H), 7.11-7.08 (dd, J=8.1 Hz, 1.5 Hz, 1H), 3.29 (s, 3H). ³C NMR (75 MHz, CDCl₃) δ (ppm): 154.9, 152.1, 151.5, 135.1, 132.8, 130.8, 130.7, 130.3, 129.7, 129.5, 128.2, 124.8, 113.9, 37.6, 36.8.

MS: m/z calcd for $C_{17}H_{15}N_3O_2$: 293.32. Found MH⁺: 294.

2-Oxo-3-phenyl-2H-quinoxaline-1-carboxylic acid diisopropylamide (2b)

The general procedure II was applied for the preparation of 2b in 75% yield. Purification was performed with (1:5) EtOAc:hexane.

¹H NMR (300 MHz, CDCl₃) δ (ppm): 8.36-8.30 (m, 3H), 7.95-7.92 (dd, J=8.1 Hz, 1.5 Hz, 1H), 7.50-7.35 (m, 5H), 7.12-7.09 (dt, J=8.1 Hz, 1.5 Hz, 1H), 3.71-3.58 (m, 2H), 1.67-1.63 (m, 2H), 1.24 (d, J=6.6 Hz, 6H), 1.08 (d, J=6.6 Hz, 6H). ¹³C NMR (75 MHz, CDCl₃) δ (ppm): 154.7, 152.6, 149.0, 135.6, 133.1, 131.0, 130.8, 130.7, 130.5, 129.8, 128.5, 124.8, 113.9, 52.2, 47.6, 21.5, 20.9, 20.4, 19.9.

MS: m/z calcd for $C_{21}H_{23}N_3O_2$: 349.43. Found MH⁺: 350.

4-Oxo-2-phenyl-4H-quinazoline-3-carboxylic acid dimethylamide (10a)

The general procedure II was applied for the preparation of 10a in 75% yield. Purification was performed with (1:5) EtOAc:hexane.

¹H NMR (300 MHz, CDCl₃) δ (ppm): 8.31 (d, J=7.8 Hz, 1H), 7.77-7.67 (m, 4H), 7.48-7.41 (m, 4H), 2.94 (s, 3H), 2.85 (s, 3H). ¹³C NMR (75 MHz, CDCl₃) δ (ppm): 162.3, 154.0, 153.8, 149.4, 137.0, 135.8, 132.6, 130.4, 129.9, 129.7, 129.4, 128.7, 122.1, 39.7, 38.4.

MS: m/z calcd for $C_{17}H_{15}N_3O_2$: 293.32. Found MH⁺: 294.

4-Oxo-2-phenyl-4H-quinazoline-3-carboxylic acid diisopropylamide (10b)

The general procedure II was applied for the preparation of 10b in 70% yield. Purification was performed with (1:10) EtOAc:hexane.

¹H NMR (300 MHz, CDCl₃) δ (ppm): 8.28 (d, J=7.8 Hz, 1H), 7.83-7.67 (m, 4H), 7.50-7.40 (m, 4H), 3.57-3.48 (m, 1H), 3.34-3.25 (m, 1H), 1.6 (d, J=6.6 Hz, 3H), 1.12 (d, J=6.6 Hz, 3H), 1.05 (d, J=6.6 Hz, 3H), 0.64 (d, J=6.6 Hz, 3H). ¹³C NMR (75 MHz, CDCl₃) δ (ppm): 161.1, 152.6, 149.4, 147.9, 135.2, 134.0 131.0, 129.7,128.6, 128.1, 127.7, 127.2, 120.9, 51.9,47.2, 21.1, 19.94, 19.90, 19.3.

MS: m/z calcd for $C_{21}H_{23}N_3O_2$: 349.43. Found MH⁺: 350.1.

1-Oxo-4-phenyl-1H-phthalazine-2-carboxylic acid dimethylamide (19a)

The general procedure II was applied for the preparation of 19a in 85% yield. Purification was performed with (1:2) EtOAc:hexane.

¹H NMR (300 MHz, CDCl₃) δ (ppm): 8.54-8.47 (m, 1H), 7.79-7.72 (m, 3H), 7.59-7.42 (m, 5H), 3.18 (s, 3H), 2.98 (s, 3H). ¹³C NMR (75 MHz, CDCl₃) δ (ppm): 157.2, 153.5, 148.2, 133.9, 133.3, 131.5, 129.0, 128.9, 128.2, 127.7, 126.9, 37.4, 36.5.

MS: m/z calcd for $C_{17}H_{15}N_3O_2$: 293.32. Found MH⁺: 294.

1-Oxo-4-phenyl-1H-phthalazine-2-carboxylic acid diisopropylamide (19b)

The general procedure II was applied for the preparation of 19b in 80% yield. Purification was performed with (1:40) EtOAc:dichloromethane.

¹H NMR (300 MHz, CDCl₃) δ (ppm): 8.5 (m, 1H), 7.76-7.74 (m, 3H), 7.62-7.47 (m, 5H), 4.15-4.02 (m, 2H), 1.39-1.15 (m, 12H). ¹³C NMR (75 MHz, CDCl₃) δ (ppm): 1573, 151.1, 147.5, 134.2, 133.0, 131.3, 129.1, 128.8, 128.1, 127.9, 126.8, 126.7, 50.9, 46.3, 20.3, 19.4.

MS: m/z calcd for $C_{21}H_{23}N_3O_2$: 349.43. Found MH⁺: 350.

2-Chloro-3-phenylquinoxaline (3)

The general procedure III was applied for the preparation of 3 in 85% yield. Purification was performed with pure dichloromethane.

¹H NMR (300 MHz, CDCl₃) δ (ppm): 8.15-8.12 (m, 1H), 8.06-8.03 (m, 1H), 7.86-7.83 (m, 2H), 7.80-7.76 (m, 2H), 7.53-7.49 (m, 3H). ¹³C NMR (75 MHz, CDCl₃) δ (ppm): 153.3, 146.5, 141.3, 141.3, 137.1, 131.2, 130.8, 130.1, 129.9, 129.5, 128.6, 128.4.

4-Chloro-2-phenyl-quinazoline (11)

The general procedure III was applied for the preparation of 11 in 80% yield. Purification was performed with pure dichloromethane.

¹H NMR (300 MHz, CDCl₃) δ (ppm): 8.58-8.55 (m, 2H), 8.21 (d, J=8.1 Hz, 1H), 8.08 (d, J=8.4 Hz, 1H), 7.91 (t, J=7.2 Hz, 1H), 7.64 (t, J=6.9 Hz, 1H), 7.51-7.49 (m, 3H).

1-Chloro-4-phenyl-phthalazine

The general procedure III was applied for the preparation of 1-Chloro-4-phenyl-phthalazine in 85% yield. Purification was performed with pure dichloromethane.
¹H NMR (300 MHz, CDCl₃) δ (ppm): 8.52 (d, J=4.8 Hz, 1H), 8.19 (d, J=5.1 Hz, 1H), 8.13 (t, J=4.2 Hz, 1H), 8.05 (t, J=5.1 Hz, 1H), 7.85-7.81 (m, 2H), 7.72-7.68 (m, 3H).

N,N-Dimethyl-2-(3-phenyl-quinoxalin-2-yl)-acetamide (4a)

The general procedure IV was applied for the preparation of 4a in 80% yield. Purification was performed with (1:2) EtOAc:hexane.
¹H NMR (300 MHz, CDCl₃) δ (ppm): 8.10-8.05 (m, 2H), 7.72-7.69 (m, 2H), 7.65-7.62 (m, 2H), 7.50-7.46 (m, 3H), 4.06 (s, 2H), 2.93 (s, 6H). ¹³C NMR (75 MHz, CDCl₃) δ(ppm): 170.8, 155.6, 151.4, 141.3, 141.0, 138.6, 130.3, 129.3, 129.0, 128.5, 128.4, 41.2, 40.9, 36.9, 34.7.
MS: m/z calcd for $C_{18}H_{17}N_3O$: 291.35. Found MH⁺: 292.

N,N-Diethyl-2-(3-phenyl-quinoxalin-2-yl)-acetamide (4b)

The general procedure IV was applied for the preparation of 4b in 75% yield. Purification was performed with (1:2) EtOAc:hexane.
¹H NMR (200 MHz, CDCl₃) δ (ppm): 8.13-8.06 (m, 2H), 7.75-7.70 (m, 2H), 7.64-7.60 (m, 2H), 7.47-7.44 (m, 3H), 4.05 (s, 2H), 3.40-3.18 (m, 4H), 1.15-1.00 (q, 6H). ¹³C NMR (75 MHz, CDCl₃) δ (ppm): 168.6, 155.3, 150.7, 141.4, 141.2, 138.9, 129.6, 129.6, 129.2, 128.9, 128.9, 128.9, 128.9, 128.8, 128.5, 128.5, 128.5, 128.5, 42.3, 41.6, 40.4, 29.7, 14.0, 12.9.
MS: m/z calcd for $C_{20}H_{21}N_3O$: 319.4. Found MH⁺: 320.

N,N-Diisopropyl-2-(3-phenyl-quinoxalin-2-yl)-acetamide (4c)

The general procedure IV was applied for the preparation of 4c in 70% yield. Purification was performed with (1:5) EtOAc:hexane.
¹H NMR (300 MHz, CDCl₃) δ (ppm): 8.11-8.06 (m, 2H), 7.72-7.69 (m, 2H), 7.60-7.57 (m, 2H), 7.45-7.42 (m, 3H), 4.02 (s, 2H), 3.88-3.79 (m, 1H), 3.40-3.31 (m, 1H), 1.32 (d, J=6.9 Hz, 3H), 1.06 (d, J=6.9 Hz, 3H). ¹³C NMR (75 MHz, CDCl₃) δ (ppm): 168.3, 155.7, 151.3, 141.6, 141.5, 139.3, 129.9, 129.5, 129.2, 129.1, 128.8, 49.3, 46.3, 43.8, 20.9, 20.8.
MS: m/z calcd for $C_{22}H_{25}N_3O$: 347.45. Found MH⁺: 348.

N-sec-Butyl-N-methyl-2-(3-phenyl-quinoxalin-2-yl)-acetamide (4d)

The general procedure IV was applied for the preparation of 4d in 70% yield. Purification was performed with (1:2) EtOAc:hexane.
¹H NMR (300 MHz, CDCl₃) δ (ppm): 8.09-8.03 (m, 4H), 7.70-7.60 (m, 8H), 7.44-7.42 (m, 6H), 4.64-4.57 (m, 1H), 4.06 (s, 2H), 3.99 (s, 2H), 3.66-3.59 (m, 1H), 2.70 (s, 3H), 2.66 (s, 3H), 1.46-1.35 (m, 4H), 1.04 (d, J=7.5 Hz, 3H), 0.99 (d, J=7.5 Hz, 3H), 0.79 (t, J=7.5 Hz, 3H), 0.69 (t, J=7.5 Hz, 3H). ¹³C NMR (75 MHz, CDCl₃) δ (ppm): 170.0, 169.7, 155.5, 151.1, 141.7, 141.6, 141.5, 139.1, 130.0, 129.5, 129.3, 129.2, 129.1, 128.8, 54.6, 50.1, 42.9, 42.2, 28.8, 27.5, 26.9, 26.2, 18.9, 18.0, 11.3, 11.2. (The compound is presented in solution by two conformeric structures)
MS: m/z calcd for $C_{21}H_{23}N_3O$: 333.43. Found MH⁺: 334.

N,N-Diethyl-2-(3-phenyl-quinoxalin-2-yl)-isobutyramide (5)

The general procedure IV was applied for the preparation of 5 in 45% yield. Purification was performed with (1:5) EtOAc:hexane.
¹H NMR (300 MHz, CDCl₃) δ (ppm): 8.09-8.06 (m, 2H), 7.75-7.72 (m, 2H), 7.43-7.37 (m, 5H), 3.07-3.02 (q, J=7.2 Hz, 2H), 2.92-2.87 (q, J=7.2 Hz, 2H), 1.56 (s, 6H), 1.03 (t, J=7.2 Hz, 3H), 0.69 (t, J=7.2 Hz, 3H). ¹³C NMR (75 MHz, CDCl₃) δ (ppm): 173.4, 158.5, 154.9, 140.9, 140.2, 139.6, 130.3, 130.1, 129.3, 129.2, 128.3, 50.6, 42.5, 41.5, 28.2, 13.8, 13.0.
MS: m/z calcd for $C_{22}H_{25}N_3O$: 347.45. Found MH⁺: 348.

N,N-Dimethyl-2-(2-phenyl-quinazolin-4-yl)-acetamide (12a)

The general procedure IV was applied for the preparation of 12a in 85% yield. Purification was performed with (1:2) EtOAc:hexane.
¹H NMR (300 MHz, CDCl₃) δ (ppm): 14.66-14.65 (br, NH), 8.60-8.56 (m, 2H), 8.27 (d, J=6 Hz, 1H), 8.17-8.14 (m, 2H), 8.04 (d, J=7.5 Hz, 1H), 7.85 (t, J=7.5 Hz, 1H), 7.75 (d, J=7.4 Hz, 1H), 7.60-7.46 (m, 9H), 7.28 (t, J=8.1 Hz, 1H), 5.70 (s, 1H), 4.44 (s, 2H), 3.24 (s, 3H), 3.10-3.0 (s, 6H), 2.98 (s, 3H). ¹³C NMR (75 MHz, CDCl₃) δ (ppm): 172.7, 170.4, 166.9, 161.7, 152.9, 139.8, 135.6, 134.2, 133.1, 132.3, 131.0, 130.8, 130.3, 130.0, 129.2, 128.6, 127.9, 127.3, 124.9, 124.3, 43.7, 40.0, 37.6.

The compound is presented in solution by two isomeric structures (1:1 ratio):

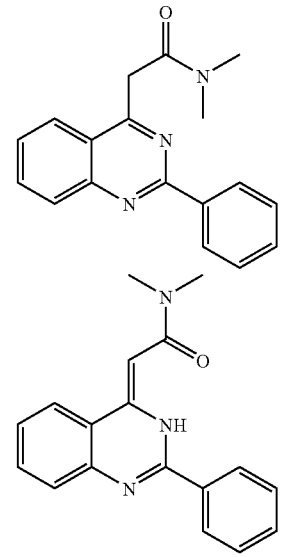

MS: m/z calcd for $C_{18}H_{17}N_3O$: 291.35. Found MH⁺: 292.

N,N-Diethyl-2-(2-phenyl-quinazolin-4-yl)-acetamide (12b)

The general procedure IV was applied for the preparation of 12b in 80% yield. Purification was performed with (1:2) EtOAc:hexane.
¹H NMR (300 MHz, CDCl₃) δ (ppm): 14.64 (br, NH), 8.60-8.56 (m, 2H), 8.27 (d, J=8.4 Hz, 1H), 8.16-8.13 (m, 2H), 8.04 (d, J=7.8 Hz, 1H), 7.83 (t, J=6 Hz, 1H), 7.70 (d, J=8.1 Hz, 1H), 7.60-7.47 (m, 9H), 7.27 (t, J=6.9 Hz, 1H), 5.66 (s, 1H), 4.42 (s, 2H), 3.61 (q, J=6 Hz, 4H), 3.42 (q, J=6 Hz, 4H), 1.23-1.12 (m, 12H). $^{13}$C NMR (75 MHz, CDCl$_3$) δ (ppm): 171.6, 169.5, 167.3, 161.7, 152.8, 152.3, 150.2, 139.8, 135.6, 135.2, 134.0, 133.0, 132.3, 131.0, 130.7, 130.3, 130.0, 129.1, 128.6, 127.9, 127.3, 124.9, 124.2, 121.6, 44.5, 43.6, 42.2, 16.2, 16.1, 14.8.

The compound is presented in solution by two isomeric structures (1:1 ratio):

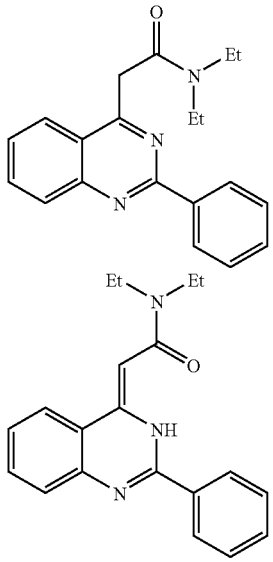

MS: m/z calcd for C$_{20}$H$_{21}$N$_3$O: 319.4. Found MH$^{30}$: 320.

N,N-Diisopropyl-2-(2-phenyl-quinazolin-4-yl)-acetamide (12c)

The general procedure IV was applied for the preparation of 12c in 75% yield. Purification was performed with (1:5) EtOAc:hexane.

$^1$H NMR (300 MHz, CDCl$_3$) δ (ppm): 14.72 (br, 1H), 8.63-8.58 (m, 2H), 8.30 (d, J=8.4 Hz, 1H), 8.2-8.13 (m, 2H), 8.04 (d, J=8.7 Hz, 1H), 7.83 (t, J=6.9 Hz, 1H), 7.5 (d, J=6 Hz, 1H), 7.59-7.47 (m, 9H), 7.27 (t, J=6.9 Hz, 1H), 5.69 (s, 1H), 4.61-4.41 (m, 1H), 4.39 (s, 2H), 4.33-4.04 (m, 2H), 3.45-3.36 (m, 1H), 1.40 (d, J=6.6 Hz, 6H), 1.37-1.34 (m, 12H), 1.06 (d, J=6.9 Hz, 6H). $^{13}$C NMR (75 MHz, CDCl$_3$) δ (ppm): 169.7, 166.8, 165.1, 159.4, 150.5, 150.2, 147.2, 137.5, 133.3, 131.6, 130.6, 130.0, 128.7, 128.0, 127.7, 126.8, 126.4, 125.6, 125.0, 122.5, 121.8, 119.5, 49.4, 45.7, 43.9, 31.1, 29.2, 22.2, 21.0, 20.3, 20.0, 13.7.

The compound is presented in solution by two isomeric structures (5:1 ratio):

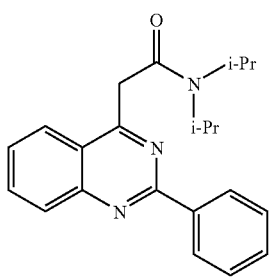

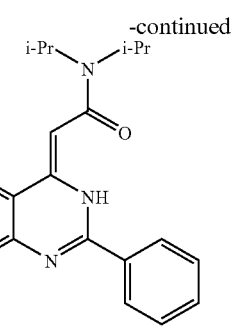

MS: m/z calcd for C$_{22}$H$_{25}$N$_3$O: 347.45. Found MH$^+$: 348.

N,N-Diethyl-2-(2-phenyl-quinazolin-4-yl)-isobutyramide (13)

The general procedure IV was applied for the preparation of 13 in 55% yield. Purification was performed with (1:5) EtOAc:hexane.

$^1$H NMR (300 MHz, CDCl$_3$) δ (ppm): 8.68 (d, J=5.1 Hz, 2H), 8.08 (t, J=9 Hz, 2H), 7.79 (t, J=6 Hz, 1H), 7.53-7.43 (m, 4H), 3.32 (q, J=6.9 Hz, 2H), 2.73(q, J=6.9 Hz, 2H), 1.82 (s, 6H), 1.08 (t, J=6.9 Hz, 3H), 0.23 (t, J=6.9 Hz, 3H). $^{13}$C NMR (75 MHz, CDCl$_3$) δ (ppm): 176.2, 174.8, 161.4, 153.3, 139.9, 135.2, 131.5, 130.4, 130.3, 128.5, 127.4, 52.4, 43.2, 42.4, 14.2, 14.1.

MS: m/z calcd for C$_{22}$H$_{25}$N$_3$O: 347.45. Found MH$^+$: 348.

N,N-Dimethyl-2-(4-phenyl-phthalazin-1-yl)-acetamide (20a)

The general procedure IV was applied for the preparation of 20a in 80% yield. Purification was performed with (2:1) EtOAc:hexane.

$^1$H NMR (300 MHz, CDCl$_3$) δ (ppm): 8.47 (d, J=7.5 Hz, 1H), 8.04 (d, J=7.5 Hz, 1H), 7.93 (t, J=6.9 Hz, 1H), 7.81 (t, J=6.9 Hz, 1H), 7.74-7.70 (m, 2H), 7.56-7.44 (m, 3H), 4.52 (s, 2H), 3.30 (s, 3H), 2.81 (s, 3H). $^{13}$C NMR (75 MHz, CDCl$_3$) δ (ppm): 170.7, 161.4, 156.7, 138.0, 134.1, 133.9, 131.9, 131.1, 130.3, 128.9, 128.4, 127.5, 41.9, 40.0, 37.6, 31.5.

MS: m/z calcd for C$_{18}$H$_{17}$N$_3$O: 291.35. Found MH$^+$: 292.

N,N-Diethyl-2-(4-phenyl-phthalazin-1-yl)-acetamide (20b)

The general procedure IV was applied for the preparation of 20b in 75% yield. Purification was performed with (1:1) EtOAc:hexane.

$^1$H NMR (300 MHz, CDCl$_3$) δ (ppm): 8.42 (d, J=8.1 Hz, 1H), 7.97 (d, J=8.4 Hz, 1H), 7.77 (t, J=8.1 Hz, 1H), 7.74 (t, J=8.1 Hz, 1H), 7.68-7.65 (m, 2H), 7.50-7.46 (m, 3H), 4.43 (s, 2H), 3.63 (q, J=6.9 Hz, 2H), 3.33 (q, J=6.9 Hz, 2H), 1.15 (t, J=6.9 Hz, 3H), 1.03 (t, J=6.9 Hz, 3H). $^{13}$C NMR (75 MHz, CDCl$_3$) δ (ppm): 168.4, 155.5, 132.5, 132.3, 130.4, 129.6, 128.8, 126.8, 126.2, 43.0, 40.9, 40.4, 14.7, 13.3.

MS: m/z calcd for C$_{20}$H$_{21}$N$_3$O: 319.4. Found MH$^+$: 320.

N,N-Diisopropyl-2-(4-phenyl-phthalazin-1-yl)-acetamide (20c)

The general procedure IV was applied for the preparation of 20c in 75% yield. Purification was performed with (1:1) EtOAc:hexane.

¹H NMR (300 MHz, CDCl₃) δ (ppm): 8.44 (d, J=7.8 Hz, 1H), 8.02 (d, J=8.1 Hz, 1H), 7.88 (t, J=7.2 Hz, 1H), 7.79 (t, J=7.2 Hz, 1H), 7.73-7.70 (m, 2H), 7.55-7.48 (m, 3H), 4.69-4.60 (m, 1H), 4.47 (s, 2H), 3.41-3.37 (m, 1H), 1.39 (d, J=6.6 Hz, 6H), 0.84 (d, J=6.6 Hz, 6H). ¹³C NMR (75 MHz, CDCl₃) δ (ppm): 169.5, 161.2, 157.0, 138.1, 133.9, 133.8, 131.9, 130.3, 128.9, 128.4, 127.4, 127.3, 51.3, 48.0, 44.6, 22.6, 223.

MS: m/z calcd for $C_{22}H_{25}N_3O$: 347.45. Found MH⁺: 348.08.

3-Phenyl-quinoxaline-2-carboxylic acid dimethylamide (6)

The general procedure V was applied for the preparation of 6 in 30% yield. Purification was performed with (1:5) EtOAc: hexane.

¹H NMR (300 MHz, CDCl₃) δ (ppm): 8.18-8.16 (m, 2H), 7.88-7.86 (m, 2H), 7.81-7.80 (m, 2H), 7.51-7.49 (m, 3H), 3.04 (s, 3H), 2.65 (s, 3H). ¹³C NMR (75 MHz, CDCl₃) δ (ppm): 160.2, 142.1, 132.8, 132.2, 131.7, 131.3, 131.0, 130.6, 39.5, 36.6, 32.1, 31.5.

MS: m/z calcd for $C_{17}H_{15}N_3O$: 277.32. Found MH⁺: 278.

Phenyl-(3-phenyl-quinoxalin-2-yl)-methanol (7)

The general procedure V was applied for the preparation of 7 in 60% yield. Purification was performed with (1:10) EtOAc:hexane.

¹H NMR (300 MHz, CDCl₃) δ (ppm): 8.17 (d, J=8.7 Hz, 1H), 8.09 (d, J=8.1 Hz, 1H), 7.79-7.74 (m, 2H), 7.39-7.31 (m, 3H), 7.21 (d, J=7.2 Hz, 3H), 7.05-6.99 (m, 2H), 6.72 (d, J=7.2 Hz, 2H), 6.07 (s, 1H). 13C NMR (75 MHz, CDCl₃) δ (ppm): 156.1, 143.4, 143.0, 141.3, 139.3, 132.2, 132.0, 131.1, 131.0, 130.5, 130.4, 130.3, 130.0, 129.6, 129.4, 74.7.

MS: m/z calcd for $C_{21}H_{16}N_2O$: 312.36. Found MH⁺: 313.

Phenyl-(2-phenyl-quinazolin-4-yl)-methanol (14)

The general procedure V was applied for the preparation of 14 in 65% yield. Purification was performed with (1:10) EtOAc:hexane.

¹H NMR (300 MHz, CDCl₃) δ (ppm): 8.65 (d, J=8.1 Hz, 2H), 8.06 (d, J=8.7 Hz, 1H), 7.84 (d, J=8.4 Hz, 1H), 7.77 (t, J=8.1 Hz, 1H), 7.55-7.50 (m, 3H), 7.41 (t, J=8.1 Hz, 1H), 7.37-7.34 (m, 2H), 7.29-7.19 (m,3H), 6.36 (s, 1H), 5.89 (br, OH). ¹³C NMR (75 MHz, CDCl₃) δ (ppm): 168.9, 159.0, 151.5, 142.2, 137.6, 134.3, 131.3, 129.7, 129.1, 128.9, 128.7, 128.0, 127.7, 124.8, 120.6, 72.8.

MS: m/z calcd for $C_{21}H_{16}N_2O$: 312.36. Found MH⁺: 313.

2-Phenyl-quinazoline-4-carboxylic acid dimethylamide (15)

The general procedure V was applied for the preparation of 15 in 35% yield. Purification was performed with (1:5) EtOAc:hexane.

¹H NMR (300 MHz, CDCl₃) δ (ppm): 8.57-8.54 (m, 2H), 8.07 (d, J=8.4 Hz, 1H), 7.93-7.83 (m, 2H), 7.57 (t, J=5.7 Hz, 1H), 7.50-7.45 (m, 3H), 3.25 (s, 3H), 2.90 (s, 3H).

MS: m/z calcd for $C_{17}H_{15}N_3O$: 277.32. Found MH⁺: 278.

Dimeric Compound—24a

The general procedure VI was applied for the preparation of 24a in 75% yield. Purification was performed with (1:2) EtOAc:dichloromethane.

¹H NMR (300 MHz, CDCl₃) δ (ppm): 8.55 (s, 2H), 8.48 (m, 1H), 7.96 (d, J=7.8 Hz, 2H), 7.71 (t, J=7.8 Hz, 3H), 7.69 (d, J=8.4 Hz, 2H), 7.60 (d, J=8.4 Hz, 2H), 7.53 (d, J=8.4 Hz, 2H), 7.47-7.44 (m, 2H), 7.40-7.29 (m, 4H), 3.77-3.66 (m, 4H).

MS: m/z calcd for $C_{34}H_{24}Cl_2N_4O_2$: 591.49. Found M⁺: 591.3.

Dimeric Compound—24b

The general procedure VI was applied for the preparation of 24b in 75% yield. Purification was performed with (1:2) EtOAc:dichloromethane.

¹H NMR (300 MHz, CDCl₃) δ (ppm): 8.58 (s, 2H), 8.22 (t, J=6.2 Hz, 2H), 7.95 (d, J=8.1 Hz, 2H), 7.68 (t, J=5.4 Hz, 2H), 7.59 (d, J=9.3 Hz, 2H), 7.54-7.47 (m, 4H), 7.40-7.37 (m, 6H), 3.50-3.46 (m, 4H). ¹³C NMR (75 MHz, CDCl₃) δ (ppm): 165.0, 157.7, 143.0, 138.0, 136.9, 133.7, 131.8, 131.1, 130.4, 130.1, 129.1, 128.9, 128.6, 127.6, 127.1, 120.6, 39.5, 30.0, 27.7.

HRMS: m/z calcd for $C_{36}H_{28}Cl_2N_4O_2$: 618.1668. Found MH⁺: 619.1690.

Dimeric Compound—24c

The general procedure VI was applied for the preparation of 24c in 80% yield. Purification was performed with (1:5) EtOAc:dichloromethane.

¹H NMR (300 MHz, CDCl₃) δ (ppm): 7.80 (d, J=9 Hz, 1H), 7.45 (d, J=8.9 Hz, 5H), 7.35-7.26 (m, 3H), 7.24-7.20 (m, 5H), 7.12-7.10 (t, J=6 Hz, 2H), 6.78 (s, 2H), 3.44-3.40 (m, 4H), 3.16-3.12 (m, 4H), 3.02 (s, 6H). ³C NMR (75 MHz, CDCl₃) δ (ppm): 163.5, 138.6, 136.0, 131.4, 130.2, 129.9, 129.0, 128.6, 127.5, 126.7, 126.0, 113.7, 49.0, 45.5, 41.7, 34.9.

MS: m/z calcd for $C_{36}H_{28}Cl_2N_4O_2$: 619.54. Found M⁺: 619.4.

Dimeric Compound—24d

The general procedure VI was applied for the preparation of 24d in 85% yield. Purification was performed with (1:5) EtOAc:dichloromethane.

¹H NMR (300 MHz, CDCl₃) δ (ppm): 8.09 (t, J=12 Hz, 2H), 7.88 (m, 3H), 7.65 (t, J=5.7 Hz, 3H), 7.51-7.42 (m, 4H), 7.38-7.31 (m, 6H), 3.58-3.52 (m, 2H), 3.34-3.22 (m, 2H), 3.12 (s, 6H), 2.23-2.09 (m, 2H). ¹³C NMR (75 MHz, CDCl₃) δ (ppm): 169.0, 157.7, 157.6, 157.4, 147.3, 136.9, 136.8, 131.6, 131.0, 130.4, 130.3, 130.1, 130.0, 128.9, 128.2, 128.0, 127.5, 127.4, 127.3, 127.2, 127.1, 122.2, 60.7, 49.6, 49.1, 37.6.

MS: m/z calcd for $C_{37}H_{30}Cl_2N_4O_2$: 633.57. Found M⁺: 633.2.

Dimeric Compound—24e

The general procedure VI was applied for the preparation of 24e in 80% yield. Purification was performed with (1:5) EtOAc:dichloromethane.

¹H NMR (300 MHz, CDCl₃) δ (ppm): 8.03 (m, 2H), 7.89 (d, J=7.8 Hz, 2H), 7.65 (t, J=4.5 Hz, 2H), 7.63-7.46 (m, 5H), 7.38-7.28 (m, 7H), 3.45-3.29 (m, 4H), 3.09 (s, 3H), 2.97 (s, 3H), 1.79-1.10 (m, 8H). ¹³C NMR (75 MHz, CDCl₃) δ (ppm): 171.1, 169.3, 169.2, 157.4, 147.7, 147.5, 137.8, 136.6, 131.1, 130.7, 130.0, 127.1, 126.8, 121.2, 61.9, 51.4, 48.2, 37.0, 33.8, 28.2, 21.0, 14.2.

HRMS: m/z calcd for $C_{40}H_{36}Cl_2N_4O_2$: 674.2294. Found MH⁺: 675.2297.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A compound represented by the structure of Formula II:

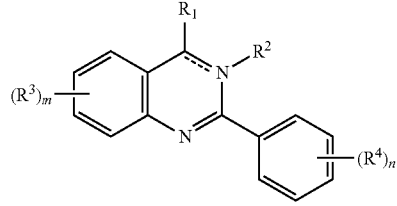

wherein
 $R^1$ is oxo, $R^2$ is a group of the formula A and === is a single bond; or $R^1$ is a group of the formula A, $R^2$ is absent and === is a double bond;
 A is represented by the structure:

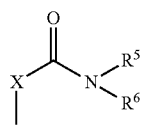

$R^3$ and $R^4$ are each independently selected from the group consisting of a linear or branched $C_1$-$C_6$ alkyl, a linear or branched $C_2$-$C_6$ alkenyl, a $C_3$-$C_8$ cycloalkyl, heterocyclyl, aryl, heteroaryl, halo, hydroxy, alkoxy, aryloxy, amino, cyano and nitro;
 $R^5$ and $R^6$ are each independently selected from the group consisting of hydrogen, a linear or branched $C_1$-$C_6$ alkyl, a linear or branched $C_2$-$C_6$ alkenyl, a $C_3$-$C_8$ cycloalkyl, heterocyclyl, aryl and heteroaryl;
 X is selected from the group consisting of a bond, —O—, —S—, and —$CR^8R^9$, wherein $R^8$ and $R^9$ are independently selected from the group consisting of hydrogen and a linear or branched $C_1$-$C_6$ alkyl;
 m is 0, 1, 2, 3 or 4; and
 n is 0, 1, 2, 3, 4 or 5;
including salts, optical isomers, geometrical isomers, enantiomers, diastereomers, and mixtures thereof.

2. The compound of claim 1, wherein:
 $R^5$ and $R^6$ are each independently selected from the group consisting of methyl, ethyl, propyl, isopropyl, n-butyl, sec-butyl, isobutyl and tert-butyl; or
 m and n are each 0; or
 X is $CH_2$, a bond or O; or
 combinations thereof.

3. The compound of claim 1, wherein the compound is represented by the structure of formula IIA or IIB

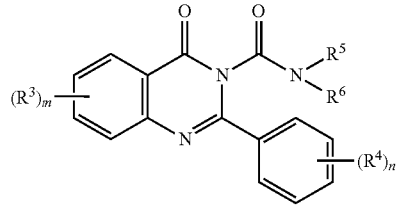

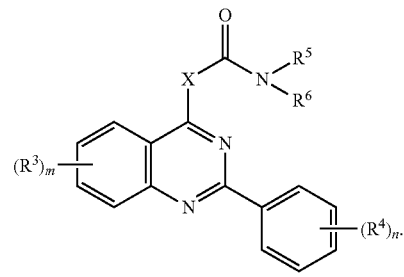

4. The compound of claim 3, wherein the compound is selected from the group consisting of:

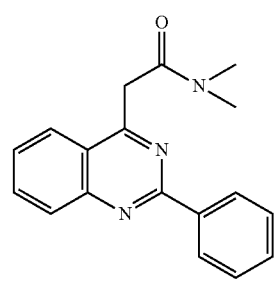

and

5. The compound of claim 3 wherein the compound is selected from the group consisting of:

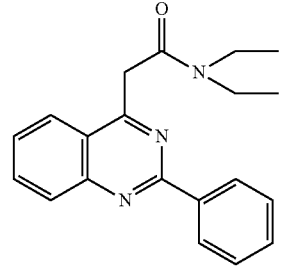

-continued

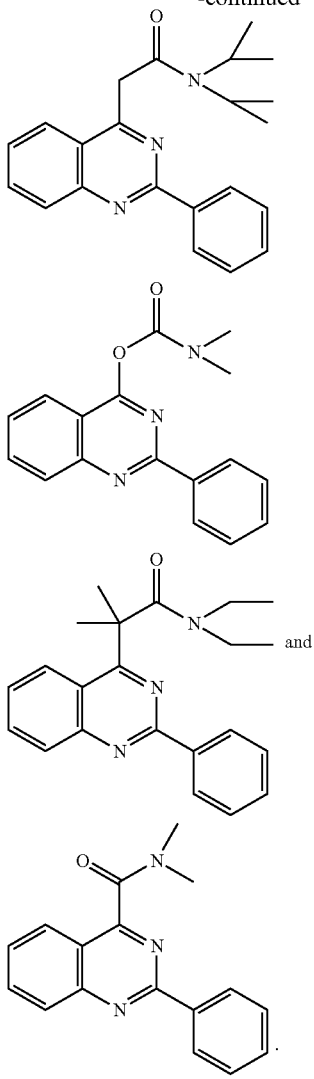
and

6. The compound of claim 3, represented by the structure of formula IIB wherein X is O.

7. The compound of claim 6, wherein $R^4$ is halo and n is 0, 1 or 2.

8. The compound of claim 6, wherein $R^5$ is and $R^6$ are each a $C_1$-$C_6$ alkyl.

9. The compound of claim 8, wherein $R^5$ is and $R^6$ are each selected from methyl, ethyl, propyl and isopropyl.

10. The compound of claim 5, which is represented by the structure:

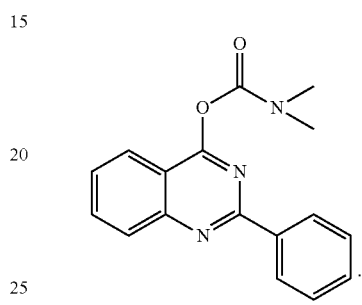

11. A pharmaceutical composition comprising a pharmaceutically acceptable carrier, and as an active ingredient a compound according to claim 1.

12. A method for preventing neurodegeneration by cell apoptosis in subject with a neurodegenerative disease, comprising the step of administering to a subject in need thereof an effective amount of a compound according to claim 1.

13. A method for treating or preventing progression of brain damage resulting from traumatic brain injury (TBI) or secondary brain damage resulting from TBI, comprising the step of administering to a subject in need thereof an effective amount of a compound according to claim 1.

* * * * *